(12) United States Patent
Berdis et al.

(10) Patent No.: US 8,981,078 B2
(45) Date of Patent: Mar. 17, 2015

(54) SELECTIVE INHIBITORS OF TRANSLESION DNA REPLICATION

(75) Inventors: Anthony J. Berdis, Cleveland, OH (US); Irene Lee, Cleveland, OH (US); Xuemei Zhang, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 357 days.

(21) Appl. No.: 13/343,381

(22) Filed: Jan. 4, 2012

(65) Prior Publication Data

US 2013/0004945 A1    Jan. 3, 2013

Related U.S. Application Data

(62) Division of application No. 11/908,306, filed as application No. PCT/US2006/009364 on Mar. 15, 2006, now Pat. No. 8,114,847.

(60) Provisional application No. 60/662,311, filed on Mar. 16, 2005.

(51) Int. Cl.
| | |
|---|---|
| *C07H 19/00* | (2006.01) |
| *C07H 21/02* | (2006.01) |
| *C07H 21/04* | (2006.01) |
| *C07H 21/00* | (2006.01) |
| *C07H 19/04* | (2006.01) |
| *C07H 19/20* | (2006.01) |
| *C07H 23/00* | (2006.01) |
| *C07H 19/052* | (2006.01) |
| *C12Q 1/68* | (2006.01) |
| *C12N 5/00* | (2006.01) |
| *C12N 5/07* | (2010.01) |
| *C12N 5/071* | (2010.01) |
| *C07H 19/22* | (2006.01) |

(52) U.S. Cl.
CPC .............. *C07H 19/00* (2013.01); *C07H 19/22* (2013.01); *C07H 21/00* (2013.01)
USPC ....... 536/26.1; 536/22.1; 536/23.1; 536/23.4; 536/24.5; 536/25.32; 536/26.2; 536/26.21; 536/26.26; 536/26.41; 536/26.9; 435/6.1; 435/6.13; 435/325; 435/363; 435/366

(58) Field of Classification Search
None
See application file for complete search history.

(56) References Cited

U.S. PATENT DOCUMENTS

| | | | |
|---|---|---|---|
| 5,401,724 A | 3/1995 | Beutler | |
| 5,446,139 A | 8/1995 | Seela et al. | |
| 5,478,852 A | 12/1995 | Olefsky et al. | |
| 5,705,490 A | 1/1998 | Townsend et al. | |
| 6,153,594 A | 11/2000 | Borretzen et al. | |
| 6,548,486 B1 | 4/2003 | Dalen | |
| 2005/0272676 A1 | 12/2005 | Bhat et al. | |
| 2006/0025375 A1 | 2/2006 | Gosselin et al. | |
| 2007/0259832 A1 | 11/2007 | Cook et al. | |
| 2009/0048202 A1 | 2/2009 | Berdis et al. | |

FOREIGN PATENT DOCUMENTS

WO    9839967    9/1998

OTHER PUBLICATIONS

Reineks et al., "Evaluating the Contribution of Base Stacking during Translesion DNA Replication", Biochemistry vol. 43 pp. 393-404, 2004, whole Document.
Cottam, et al., "Synthesis of 2'-Deoxyribofuranosyl Indole Nucleosides Related to the Antibiotics SF-2140 and Neosidomycin", Journal of Heterocyclic Chemistry, vol. 25, pp. 361-366, 1998, whole document, especially p. 363.
Costigan, Christine, et al., "A Synthetic Lethal Screen Identifies SLK1, a Novel Protein Kinase Homolog Implicated in Yeast Cell Morphogenesis and Cell Growth", Molecular and Cellular Biology, Mar. 1992, p. 1162-1178.
Devadoss, Babho, et al., "Is a Thymine Dimer Replicated via a Transient Abasic Site Intermediate? A Comparitivs Study Using Non-Natural Nucloetides", Biochemistry 2007, 46, 4486-4498.
Grieb, Pawel, et al., "5'Esters of 2'deoxyadenosine and 2-chloro-2'-deoxyadenosine with cell differentiation-provoking agents", Acta Biochimica Polonica, vol. 49, No. 1/2002, p. 129-137.
Zhang, Xuemei, et al., "Rational Attempts to Optimize Non-Natural Nucleotides for Selective Incorporation Opposite an Abasic Site", Biochemistry 2006, 45, 13293-13303.
Zhang, Xuemei, et al., "Hydrophobocity, Shape, and Π-Electron Contributions during Translesion DNA Synthesis", J. Am. Chem. Soc. 2006. 128, 143-149.
Zhang, Xuemei, et al., "A Potential Chemotherapeutic Strategy for the Selective Inhibition of Promutagenic DNA Synthesis by Non-natural Nucleotides", Biochemistry 2005, 44, 13111-13121.
Girgis, N.S., et al., "Synthesis of 2'deoxyribofuranosyl indole nucleosides related to the antibiotics SF-2140 and neosidomycin", Journal of Heterocyclic Chemistry, 2009, vol. 25, No. 2, pp. 361-366.
Motea, E.A., et al., "A non-natural nucleoside with combined therapeutic and diagnostic activities against leukemia", ACS Chemical Biology, Mar. 5, 2012, vol. 7, No. 6, pp. 988-998.

*Primary Examiner* — Jennifer Dunston
*Assistant Examiner* — Addison D Ault
(74) *Attorney, Agent, or Firm* — Tarolli, Sundheim, Covell & Tummino LLP

(57) ABSTRACT

An agent for inhibiting translesion DNA replication comprises a non-natural adenine ribose analog represented by those as set forth in FIG. 1.

4 Claims, 17 Drawing Sheets dATP    Ind-TP

5-NITP    5-AITP

5-FITP    5-PhITP

A

```
5' -TCGCAGCCGTCCA
3' -AGCGTCGGCAGGTXCCCAAA
```
X = A, C, G, T or abasic site

B

A

B

A

B

A

B

A

```
5'-TCGCAGCCGTCCA
3'-AGCGTCGGCAGGTXCCCAAA
```
                        X = T or abasic site

B

SELECTIVE INHIBITORS OF TRANSLESION DNA REPLICATION

RELATED APPLICATION

This application is a divisional application of U.S. Ser. No. 11/908,306, filed on Sep. 11, 2007, which is a National Phase filing of PCT/US06/09364, filed Mar. 15, 2006 and claims priority from U.S. Provisional Application Nos. 60/662,311, filed Mar. 16, 2005 which is herein incorporated by reference in its entirety.

GOVERNMENT FUNDING

The U.S. government may own rights in this invention pursuant NIH Grant No. R01 CA118408.

FIELD OF THE INVENTION

The present invention relates to selective inhibitors of translesion DNA replication and to methods of using such inhibitors for therapeutic and diagnostic applications.

BACKGROUND

Chemotherapeutic agents that compromise the integrity of nucleic acid are important components in modern medical efforts to combat hyperproliferative diseases, such as cancer and autoimmune dysfunctions as well as viral and microbial infections. Many compounds, such as BCNU, cyclophosphamide, and cisplatin are effective chemotherapeutic agents because they significantly modify nucleic acid and inhibit DNA synthesis and/or DNA repair to prevent cellular proliferation. However, the widespread use of these agents is limited by two major complications. First, they are non-selective DNA damaging agents. Second, these agents induce lesions that if inappropriately replicated can cause further mutagenic events to potentiate oncogenesis. Translesion DNA synthesis also represents a possible route for the initiation of drug resistance, genetic variations associated with solid tumors, and the development of secondary cancers.

These concerns have prompted the design of more selective drugs that target specific enzymes involved in nucleic acid metabolism. Arguably, the more successful of these agents are nucleotide analogs, such as AZT and acyclovir, that terminate DNA polymerization. The use of these agents is historically associated with the treatment of viruses, such as HIV and herpes simplex virus. However, they and other analogs, such as araC and fludarabine have also been used in the treatment of cancer. Unfortunately, the therapeutic utility of these nucleotide analogs is often limited by complications. The most prevalent of these complications is the excision of the enzymatically-inserted nucleotide from the primer-template to reverse chain termination which allows for the re-initiation of DNA synthesis. Although viral polymerases use pyrophosphorolysis to remove chain terminators from DNA, eukaryotes use exonuclease proofreading activity to effectively excise the inserted chain terminator. Either activity provides a mechanism for drug resistance. Another complication is that these inhibitors contain alterations in the ribose moiety while the nucleobase portion remains identical to that of a natural nucleoside. As a consequence, there is an intrinsic lack of selectivity for inhibiting one DNA polymerase versus another. Since these agents resemble their natural counterparts, they may be degraded by cellular enzymes that metabolize natural nucleotides. For example, this complication limits the use of fludarabine and may play a significant role in the development of drug resistance to other natural nucleoside analogs.

SUMMARY OF THE INVENTION

The present invention relates to agents that are selective inhibitors of translesion DNA replication. The agents comprise selective nucleoside analogs that have enhanced binding affinity and faster polymerization to abasic sites on mutagenic DNA than natural nucleosides. The agents in accordance with the present invention can target and inhibit pro-mutagenic DNA synthesis, a leading culprit in disease development as well as in the development of drug resistance.

The agents in accordance with the present invention can comprise a nucleoside analog that is selectively inserted opposite an abasic site of damaged or mutagenic DNA. The therapeutic agent behaves as a chain terminator once inserted and is poorly incorporated into unmodified (i.e., natural) DNA. In an aspect of the invention, the nucleoside analog can have the following formula (I):

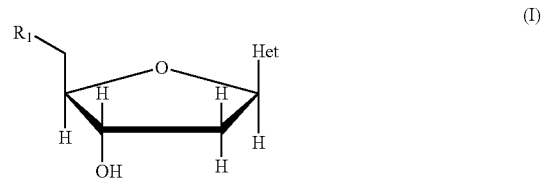

where Het is a heterocyclic azaindene analog (e.g., purine analogs or indole analog) selected from the group consisting of:

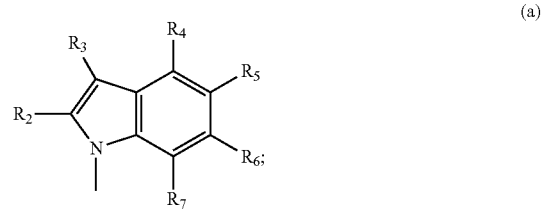

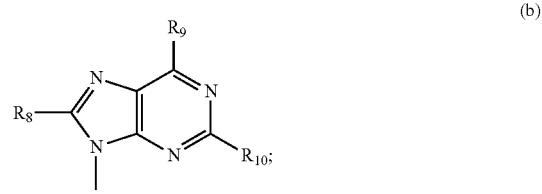

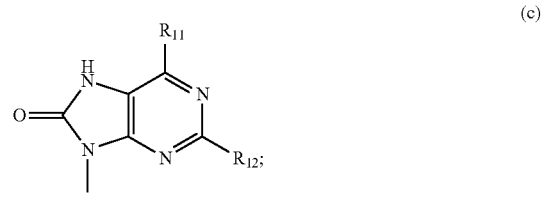

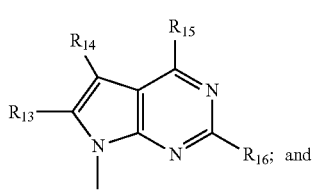

(d)

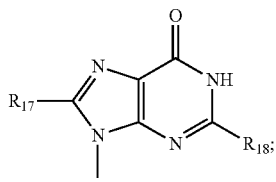

(e)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$, each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ is other than hydrogen and that where $R_9$ is amino $R_{10}$ is other than hydrogen; a pharmaceutically acceptable salt thereof, or a prodrug thereof.

In another aspect of the invention, the nucleoside analog can have the following formula (II):

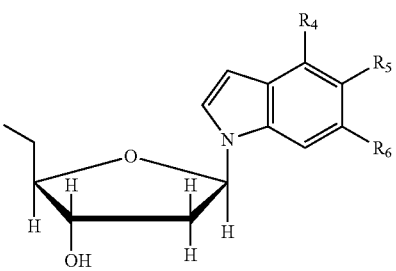

(II)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_4$, $R_5$, and $R_6$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, and $R_6$, is other than hydrogen; a pharmaceutically acceptable salt thereof, or a prodrug thereof.

In another aspect of the invention, at least one of $R_4$, $R_5$, and $R_6$ is a halo, (e.g., fluoro), amino, nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethenyl, cyclohexenyl), carboxyl, or nitro; a pharmaceutically acceptable salt thereof; or a prodrug thereof.

In yet another aspect of the invention, at least one of $R_4$, $R_5$, and $R_6$ is a substituent that has a π-electron surface area and density effective to facilitate base stacking interactions and enhance the efficiency of insertion of the nucleoside analog opposite a non-templating DNA lesion.

In a further aspect of the invention, the nucleoside analog can have the following formula (III):

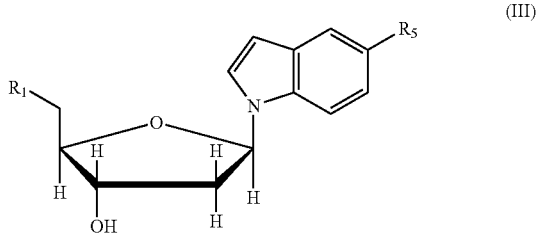

(III)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_5$ is a halo, (e.g., fluoro), amino, nitro, $C_3$-$C_{20}$ aryl (e.g., phenyl or napthyl), $C_1$-$C_{24}$ alkyl (e.g., ethenyl, cyclohexenyl), $C_2$-$C_{24}$ alkenyl (e.g., ethylene, cyclohexene), carboxyl, or nitro; a pharmaceutically acceptable salt thereof; or a prodrug thereof.

In a further aspect of the invention R5 is a substituent that has a π-electron surface area and density effective to facilitate base stacking interactions and enhance the efficiency of insertion of the nucleoside analog opposite a non-templating DNA lesion.

The agents in accordance with the present invention can be used as a therapeutic agent in methods for inhibiting translesion DNA synthesis in cells containing mutagenic DNA. In an aspect of the invention, the therapeutic agents in accordance with the invention can be used in a method of treating a proliferative disease (e.g., Leukemia), such as in a patient (e.g., a mammal, such as a human) in need of such treatment. The method can comprise the administration of the therapeutic agent alone or in conjunction with other therapeutic agents. The other therapeutic agents can comprise promutagenic and/or cytotoxic agents that can potentially compromise the integrity of nucleic acids associated with DNA replication and cellular proliferation (i.e., DNA damaging agents). The DNA damaging agents can comprise chemotherapeutic agents (e.g., alkylating agents), antimetabolites, antitumorgenic agents, antimitotic agents, antineoplastic agents. The therapeutic agents can potentiate the effects of at least some of these other therapeutic agents.

The present invention also relates to a method of monitoring DNA damage. In the method a sample containing cells from a patient is obtained. The sample is treated with a fluorescent agent that has the following formula (II):

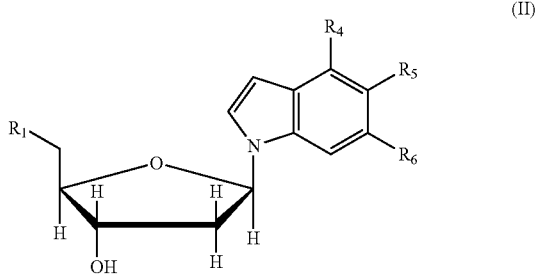

(II)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_4$, $R_5$, and $R_6$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, and $R_6$, is other than hydrogen; a pharmaceutically acceptable salt thereof;

The amount of fluorescent agent incorporated into the DNA of the cells is then determined. In a further aspect of the invention, the amount of fluorescent agent incorporated into the DNA is determined by flow cytometry. The fluorescent agent can comprise 5-phenyl-indolyl-2' deoxyriboside, a phosphate thereof, or a pharmaceutically acceptable salt thereof.

The reaction was then terminated at various times by the addition of 350 mM EDTA at the times demarcated on the graphs. Assays monitoring the insertion of 5-PhIMP opposite T were performed under identical conditions exception that the concentration of 5-PhITP was maintained at 100 μM.

Figure 4:
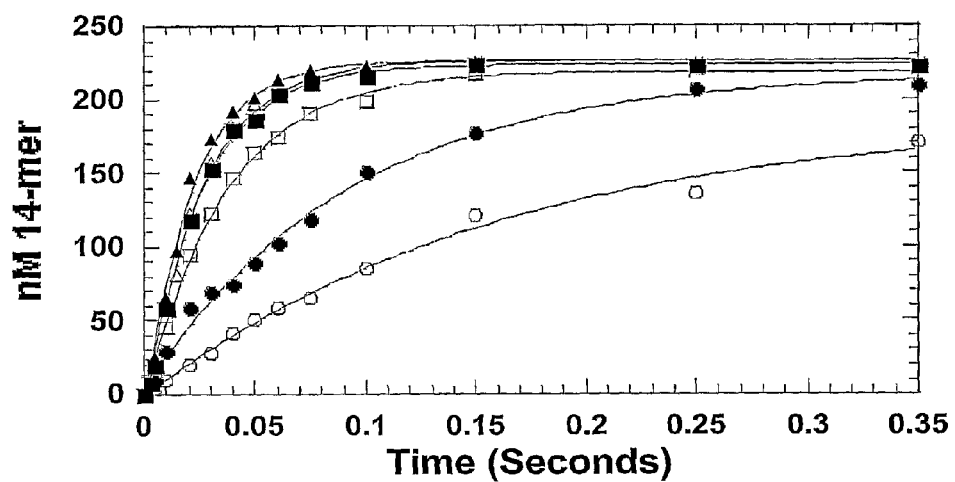
Figure 4:
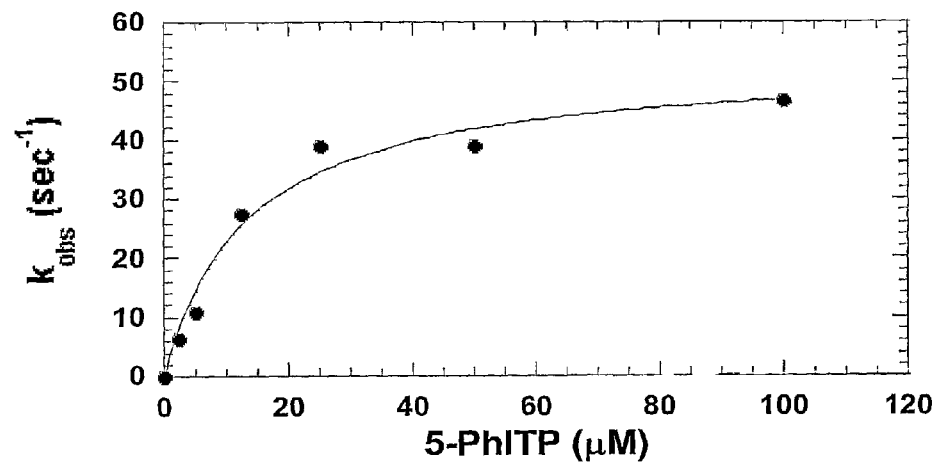

FIG. 4(A-B) are plots illustrating the dependency of 5-PhITP concentration on the observed rate constant in primer elongation as measured using single turnover conditions. (A) gp43exo⁻ (1 μM) and 5'-labeled 13/20SP-mer (250 nM) were preincubated, mixed with increasing concentrations of $Mg^{2+}$:5-PhITP to initiate the reaction, and quenched with 500 mM EDTA at variable times (0.005-0.25 sec). The incorporation of 5-PhITP was analyzed by denaturing gel electrophoresis. 5-PhITP concentrations were 2.5 μM (○), 5 μM ( ), 12.5 μM ( ), 25 μM (□), 50 μM (Δ) and 100 μM (▲). The solid lines represent the fit of the data to a single exponential. (B). The observed rate constants for 5-PhIMP insertion ( ) were plotted against 5-PhITP concentration and fit to the Michaelis-Menten equation to determine values corresponding to $K_d$ and $k_{pol}$.

Figure 5:
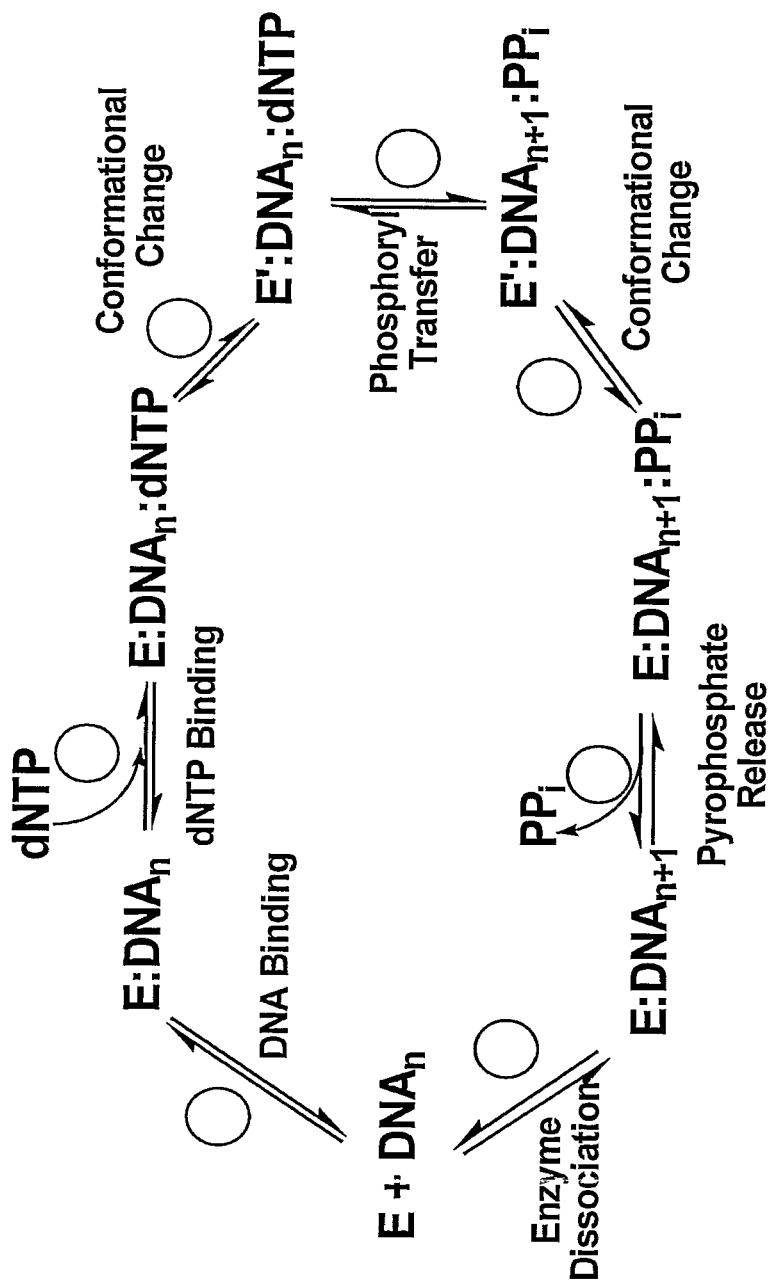

FIG. 5 is a schematic illustration of a kinetic mechanism of gp43exo–, the bacteriophage T4 DNA polymerase. Individual steps along the pathway for DNA polymerization are numbered and identified. Abbreviations: E=T4 DNA polymerase, DNAn=DNA substrate, E'=conformational change in DNA polymerase, $PP_i$=inorganic pyrophosphate, and DNAn+1=DNA product (DNA extended by one nucleobase).

Figure 6:
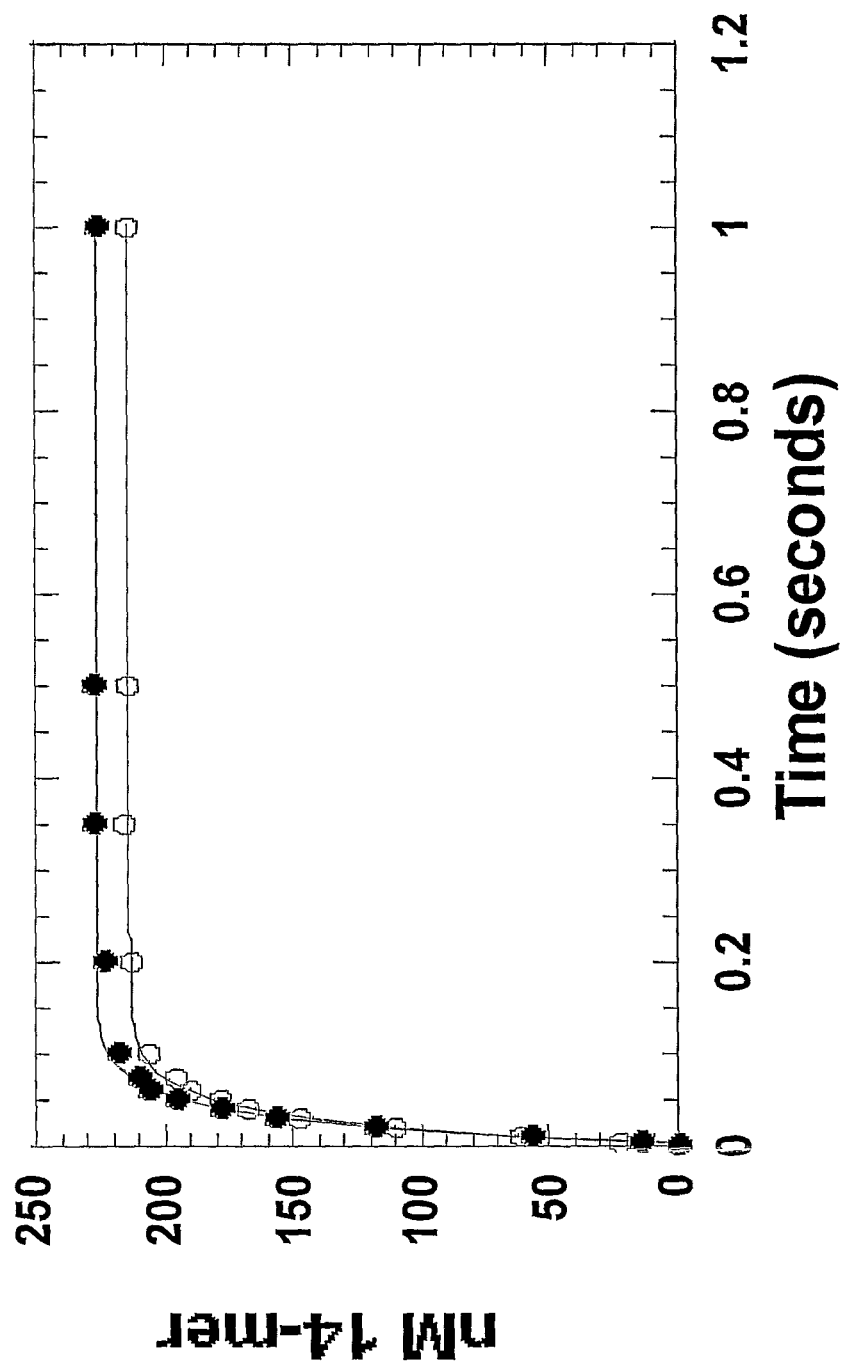

FIG. 6 is a plot illustrating rapid quench kinetic time courses for the incorporation of 5-PhITP opposite an abasic site using EDTA (●) or HCl (○) as the quenching reagent. The gp43 exo– (1 μM) and 5'-labeled 13/20SP-mer (250 nM) were preincubated, mixed with 10 mM $Mg^{2+}$ and 30 μM 5-PhITP to initiate the reaction, and quenched with either 500 mM EDTA or 1 M HCl at variable times (0.005-0.35 s). After quenching with HCl, 100 mL of phenol/chloroform/iso-amyl alcohol was added to extract the polymerase, and the pH of the aqueous phase was neutralized with the addition of 1 M Tris/3 M NaOH. Product formation was analyzed by denaturing gel electrophoresis followed by phosphorimaging analysis. A burst amplitude of 240±6 nM and a kobs of 38.4±2.1 s⁻1 were obtained using EDTA as the quench, while a burst amplitude of 220 (3 nM and a kobs of 37.4±1.4 s-1 were obtained using HCl as the quench.

Figure 7:
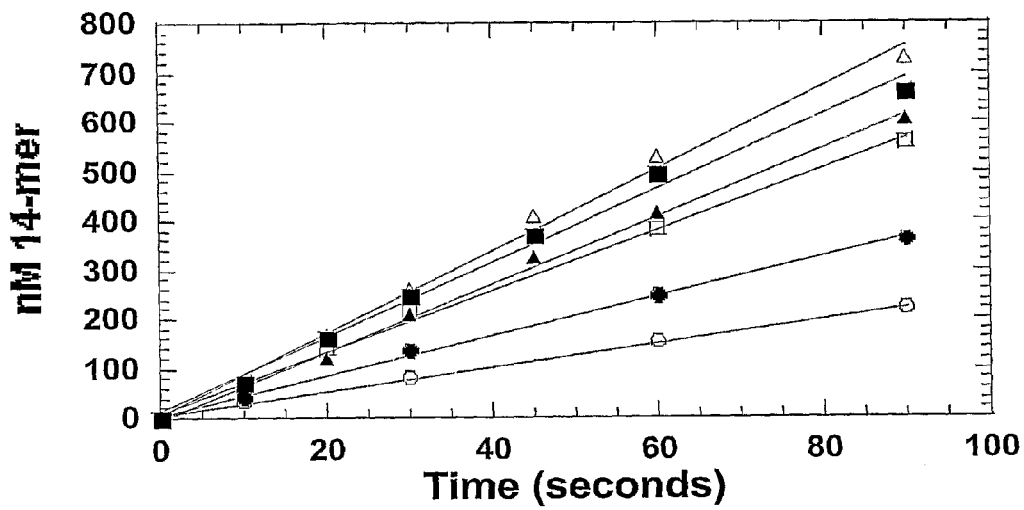
Figure 7:
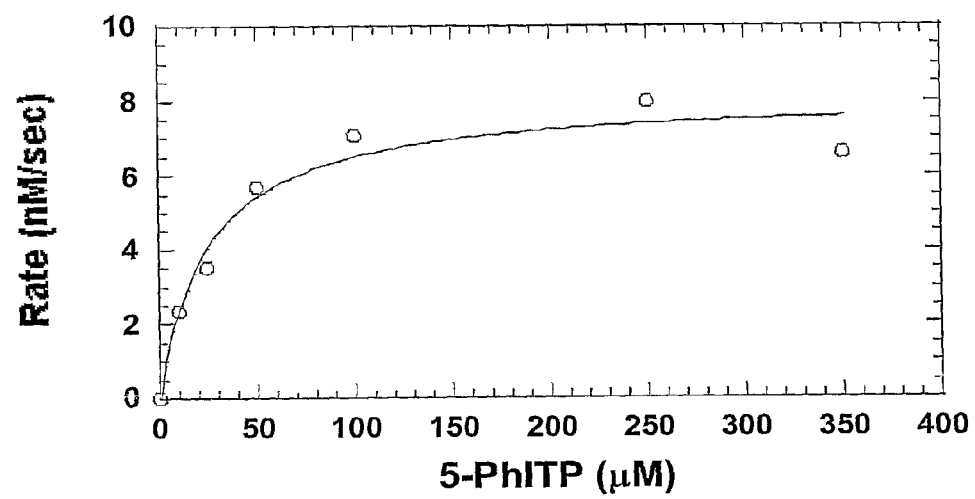

FIG. 7(A-B) are plots illustrating the dependency of 5-PhITP concentration on incorporation opposite T as measured under pseudo-first-order reaction conditions. (A) gp43 (50 nM) and 5'-labeled 13/20SP-mer (1 μM) were preincubated, mixed with increasing concentrations of $Mg^{2+}$/5-PhITP to initiate the reaction, and quenched with 200 mM EDTA at variable times (5-120 s). The insertion of 5-PhIMP was analyzed by denaturing gel electrophoresis. 5-PhITP concentrations were 10 (○), 25 (●), 50 (□), 100 (▲), 250 (■), and 350 M (Δ). The solid lines represent the fit of the data to a straight line. (B) The observed rates for 5-PhIMP insertion (○) were plotted against 5-PhITP concentration and fit to the Michaelis-Menten equation to determine values corresponding to $K_D$ and $k_{pol}$.

Figure 8:
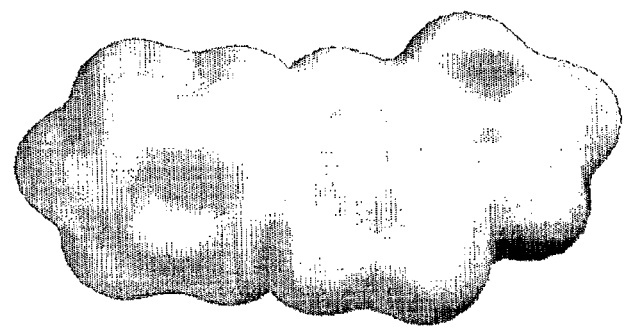
Figure 8:
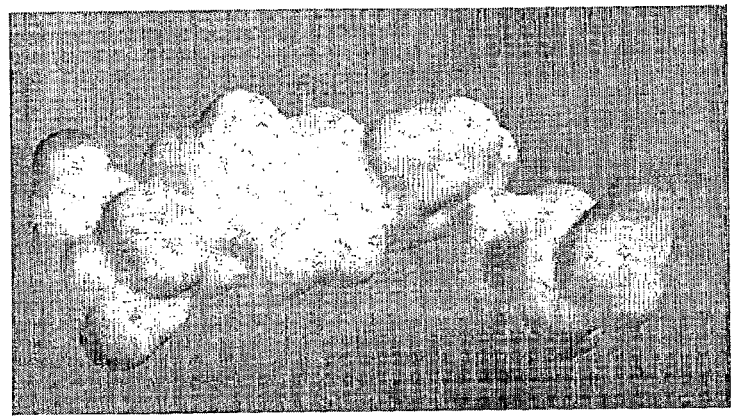
Figure 8:
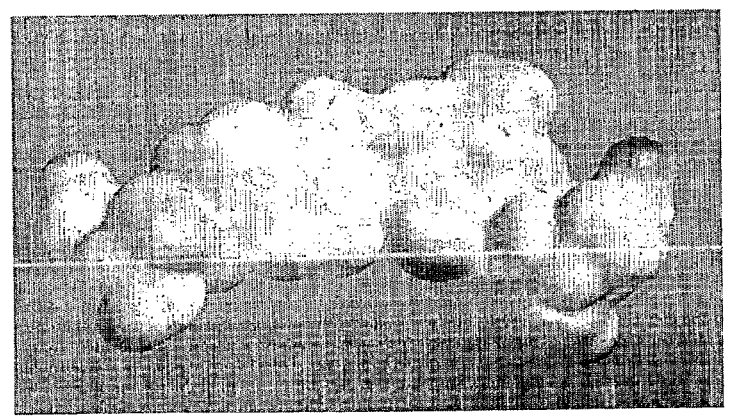

FIGS. 8(A-B) are: (A) Computer-generated model for 5-phenyl-indoledeoxyribose. Electrostatic surface potentials were generated using Spartan '04 software. Red indicates the highest electronegative regions, green is neutral, and blue indicates electropositive regions. The partial atomic charges were calculated using Hartree-Fock 3-21G(*) (displayed) or the AM1 model (data not shown). (B) Computer-generated model comparing the structures of base pairs corresponding to 5-phenyl-indole-deoxyribose monophosphate paired opposite an abasic site (top) with that for adenine deoxyribose monophosphate paired opposite thymine deoxyribose monophosphate (bottom). Electrostatic surface potentials were generated using Spartan '04 software as described above.

Figure 9:
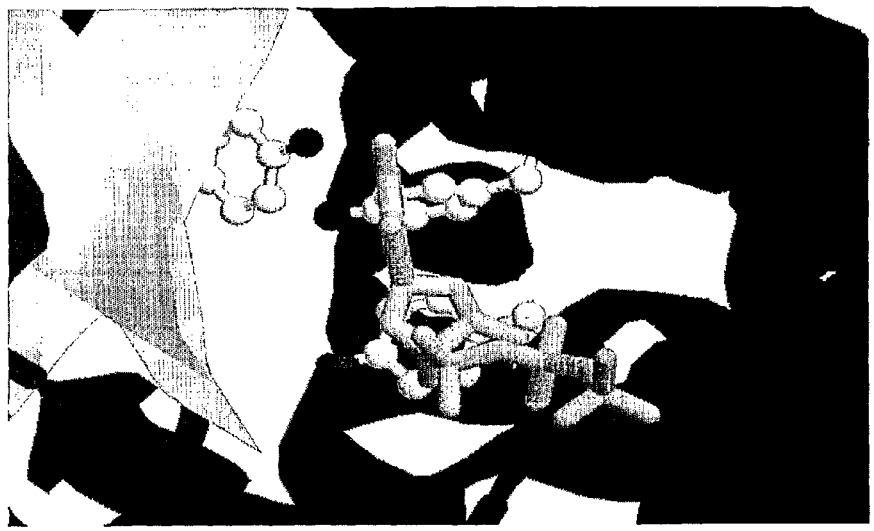

FIG. 9 is a computer generated model for proposed π-π stacking interactions of the incoming dNTP with aromatic amino acids in the active site of RB69 DNA polymerase. For clarity, the conserved aromatic amino acids of the DNA polymerase are colored in blue. The 3'-terminal of DNA duplex is colored yellow. The coming dTTP, colored in pink, is shown as a stick model.

Figure 10:
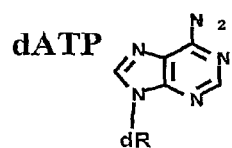
Figure 10:
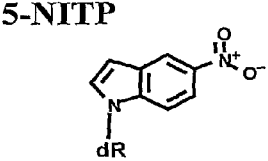
Figure 10:
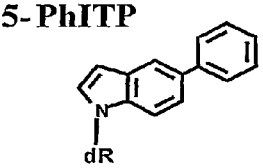

FIG. 10 illustrates (A) structures of 2'-deoxynucleoside triphosphates used in this study are dATP, 5-NITP, and 5-PhITP. For convenience, dR is used to represent the deoxyribose triphosphate portion of the nucleotide. (B) Defined DNA substrates used for kinetic analysis. "X" in the template strand denotes thymine or the presence of a tetrahydrofuran moiety that functionally mimics an abasic site.

Figure 11:
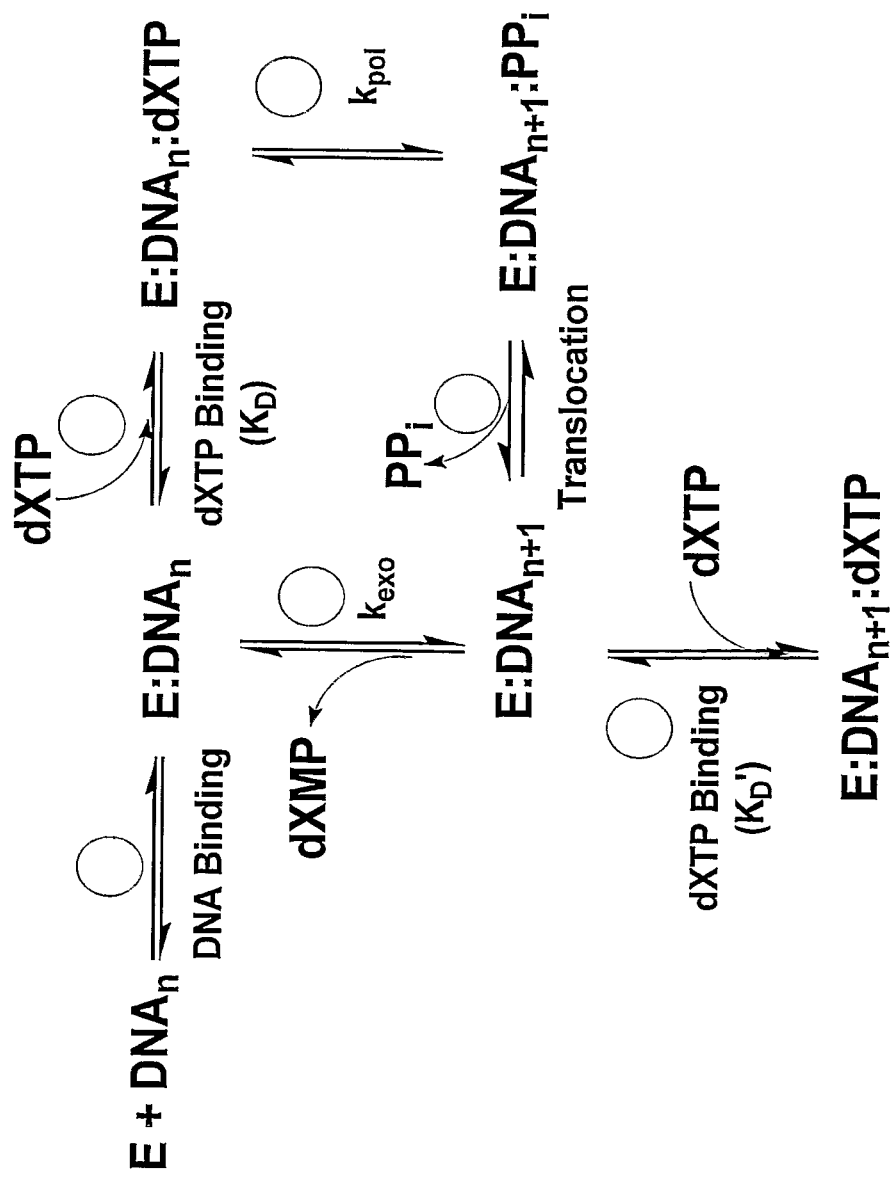

FIG. 11 is a schematic illustration of a mechanism of idle turnover of dXTP opposite an abasic site or thymine. Individual steps along the pathway are numbered and identified as follows: Step 1 represents the binding polymerase to DNA and is defined as the $K_D$ DNA, Step 2 represents the binding of dXTP to the polymerase: DNA complex and is defined as the $K_{D\ dXTP}$, Step 3 represents the rate constant in DNA polymerization as is denoted as $k_{pol}$, Step 4 represents translocation and pyrophosphate release, Step 5 represents the rate constant of exonucleolytic degradation of $DNA_{n+1}$ to yield $DNA_n$ and is defined as kexo, and Step 6 represents the binding of dXTP to the polymerase DNA complex at the next templating position and is denoted as $K_{D'}$. Abbreviations: E=gp43exo⁺, $DNA_n$=DNA substrate, $PP_i$=inorganic pyrophosphate, and $DNA_{n+1}$=DNA product (DNA extended by one nucleobase).

Figure 12:
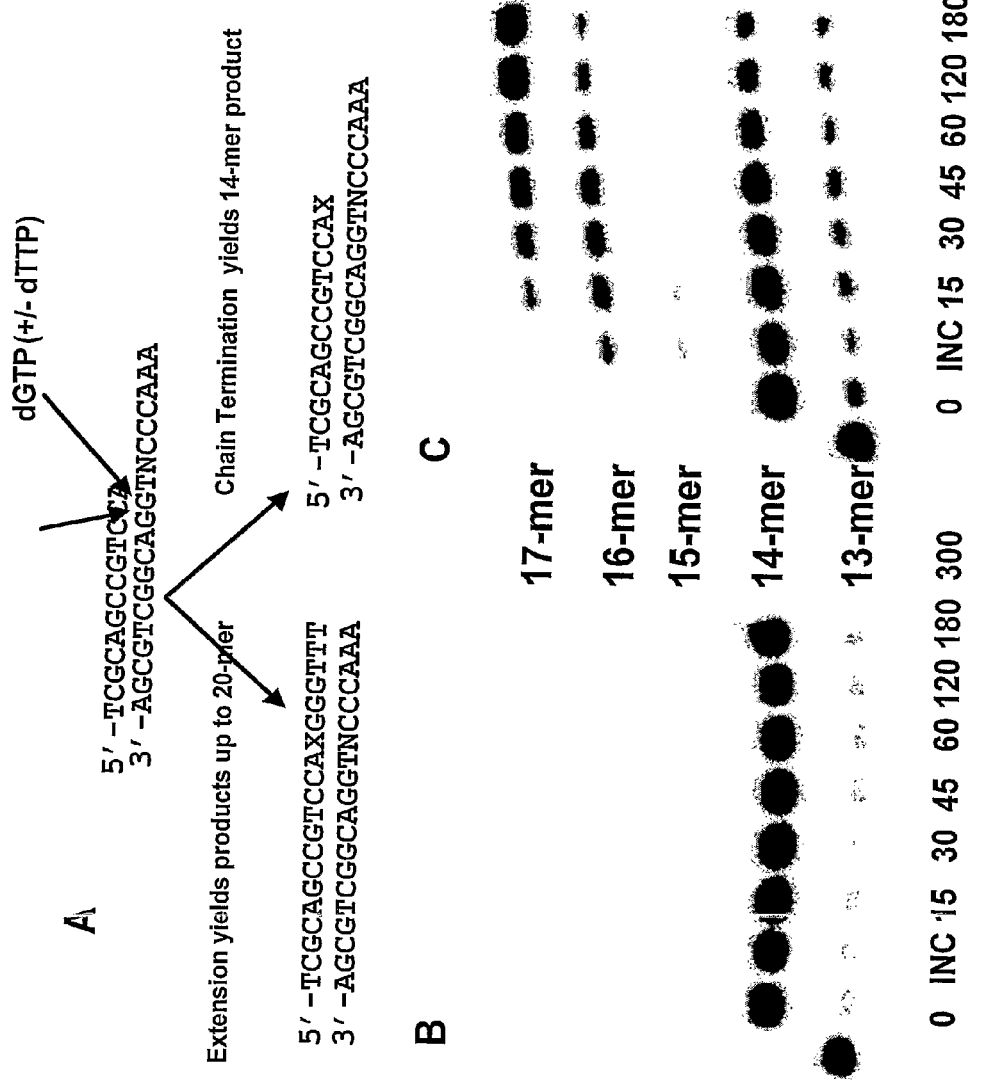

FIG. 12 illustrates 5-NITP is a chain terminator of translesion DNA synthesis. (A) Protocol used to measure the ability of gp43 exo– to extend beyond nonnatural mispairs. Assays monitoring translesion DNA synthesis were performed mixing a preincubated solution of 1 μM gp43 exo–, 500 nM 5'-labeled 13/20SP-mer, and 10 mM $Mg^{2+}$ with 50 μM 5-NITP for 30 s (B) or 500 μM dATP for 3 min (C). In both cases, 1000 μM dGTP was then added to allow for elongation beyond the formed mispair. The reaction was then terminated at various times by the addition of 200 mM EDTA at time intervals ranging from 5 to 300 s. Nucleotide incorporation was analyzed by denaturing gel electrophoresis.

Figure 13:
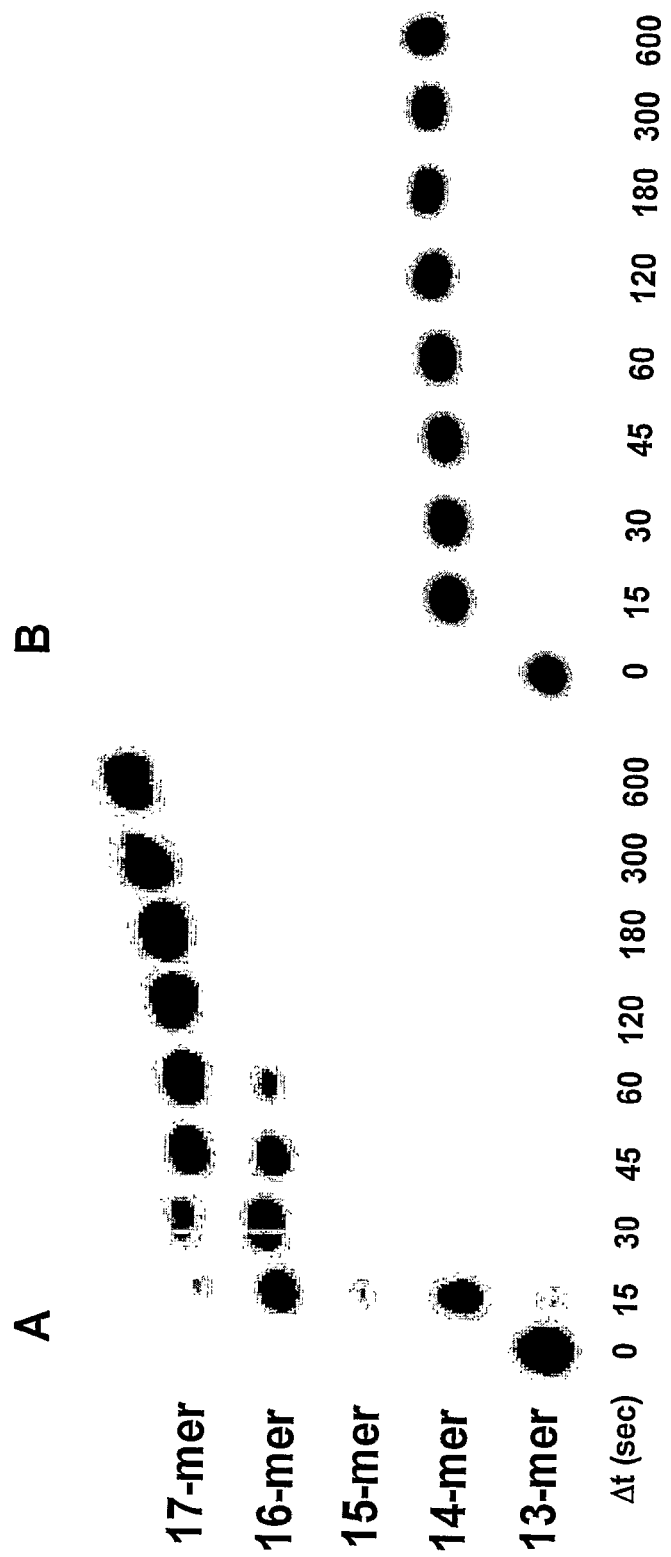

FIG. 13 illustrates 5-NITP competes with dATP for binding to the DNA polymerase during translesion DNA synthesis. gp43 exo⁻ (1 μM) and 5'-labeled 13/20SP-mer (250 nM) were preincubated in the presence of 10 mM Mg2+ and mixed with 500 μM dATP and 1000 μM dGTP in the absence (A) or presence of 20 μM 5-NITP (B). In both cases, the reactions were terminated at various times by the addition of 200 mM EDTA at time intervals ranging from 5-300 seconds. Nucleotide incorporation was analyzed by denaturing gel electrophoresis.

Figure 14:
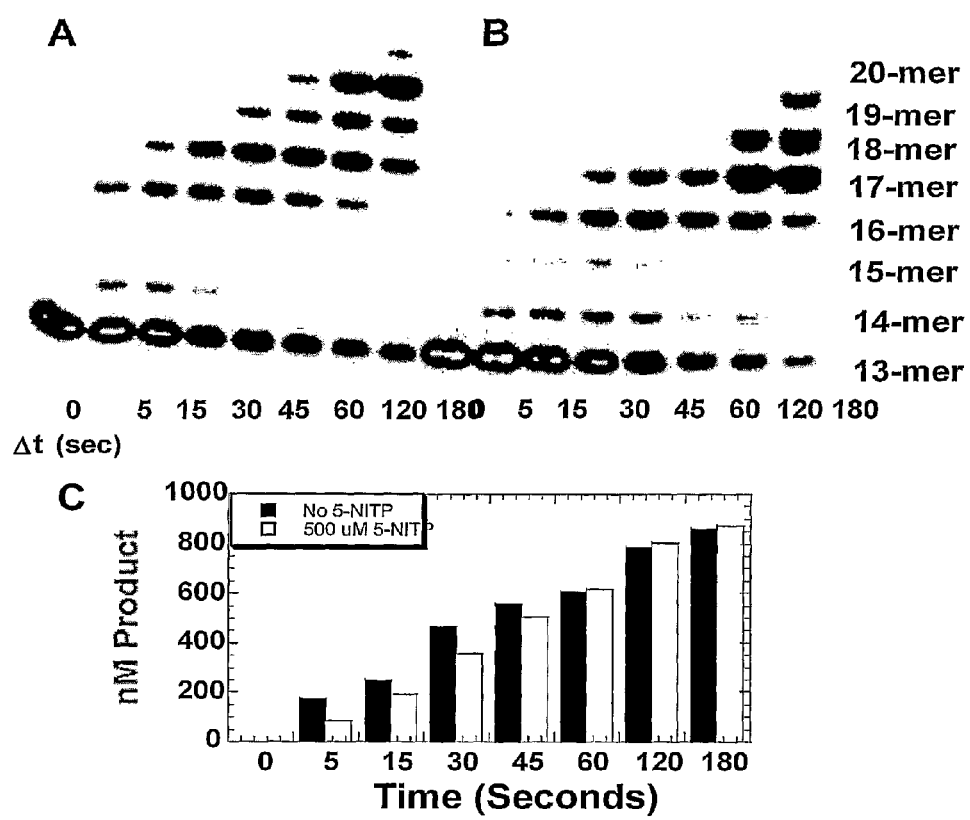

FIG. 14 illustrates 5-NITP does not inhibit DNA synthesis using undamaged DNA. 10 nM gp43 exo⁻ and 1000 nM 5'-labeled 13/20-mer were preincubated in the presence of 10 mM $Mg^{2+}$ and mixed with 10 μM dNTPs (dATP, dGTP, and dTTP) in the absence (A) or presence of 500 μM NITP (B). In both cases, the reactions were terminated at various times by the addition of 200 mM EDTA at time intervals ranging from 5-300 seconds. Nucleotide incorporation was analyzed by denaturing gel electrophoresis. Figure C reports the amount of product formed as a function of time.

Figure 15:
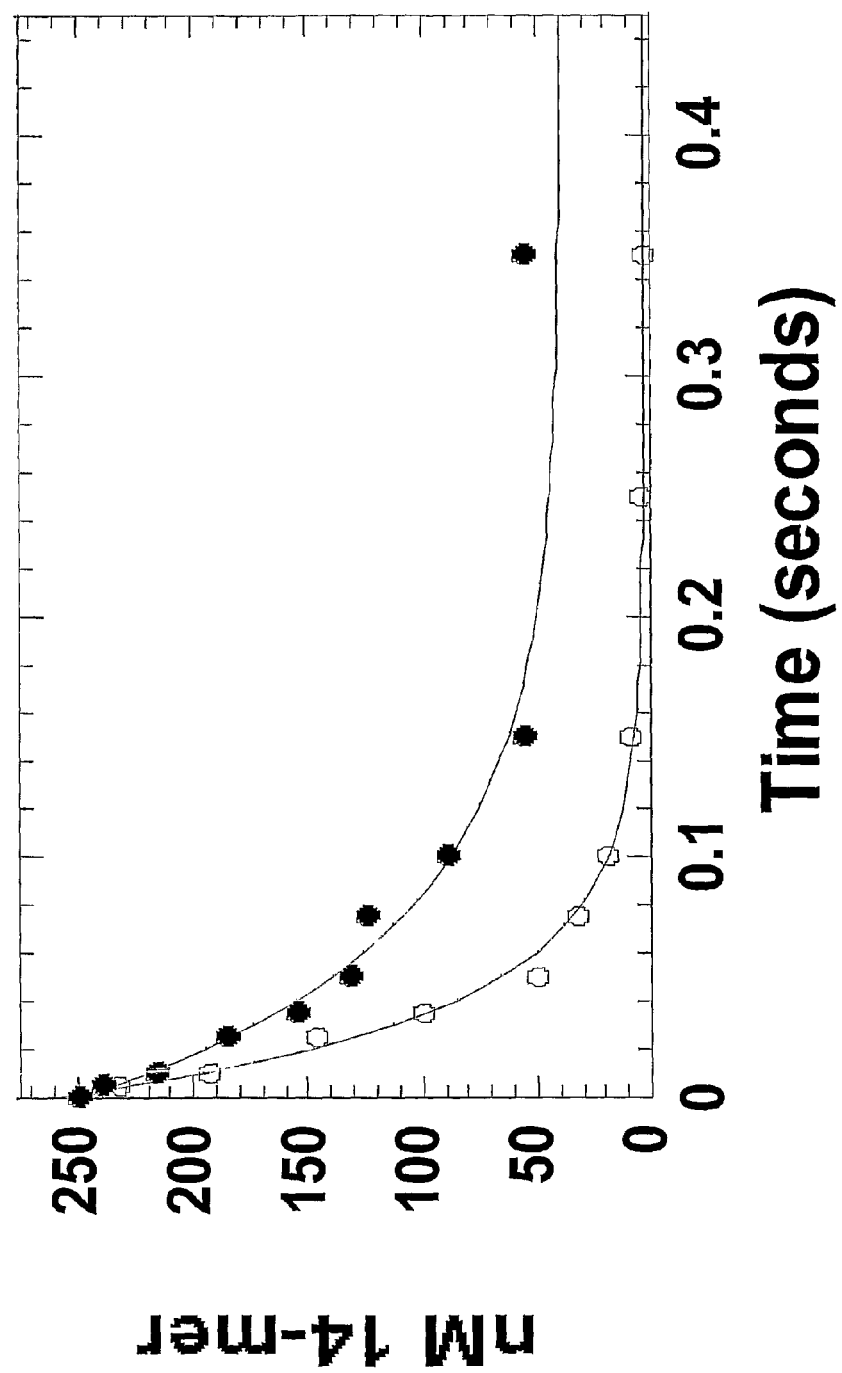

FIG. 15 illustrates 5-NIMP is excised slower than dAMP when placed opposite an abasic site. The time course in excision of dXMP opposite the lesion was performed mixing a preincubated solution of 1 μM gp43 exo+:10 mM Mg2+ versus 250 nM 5'-labeled DNA:10 mM Mg2+ (final concentrations) and terminating the reaction at various times by the addition of 350 mM EDTA. The time course in dAMP excision is represented by ( ) while that for 5-NIMP excision is represented by (O). Each time course represents an average of three independent determinations. Time courses were fit to the equation for single exponential decay, $y=Ae^{-kt}+C$, where A is the burst amplitude, k is the observed rate constant for product formation, and C is the end point of the reaction. The rate constant, $k_{exo}$, for excising dAMP is $28.5+/-1.1$ sec$^{-1}$ while for measured for 5-NIMP excision is $9.9+/-0.8$ sec$^{-1}$.

Figure 16:
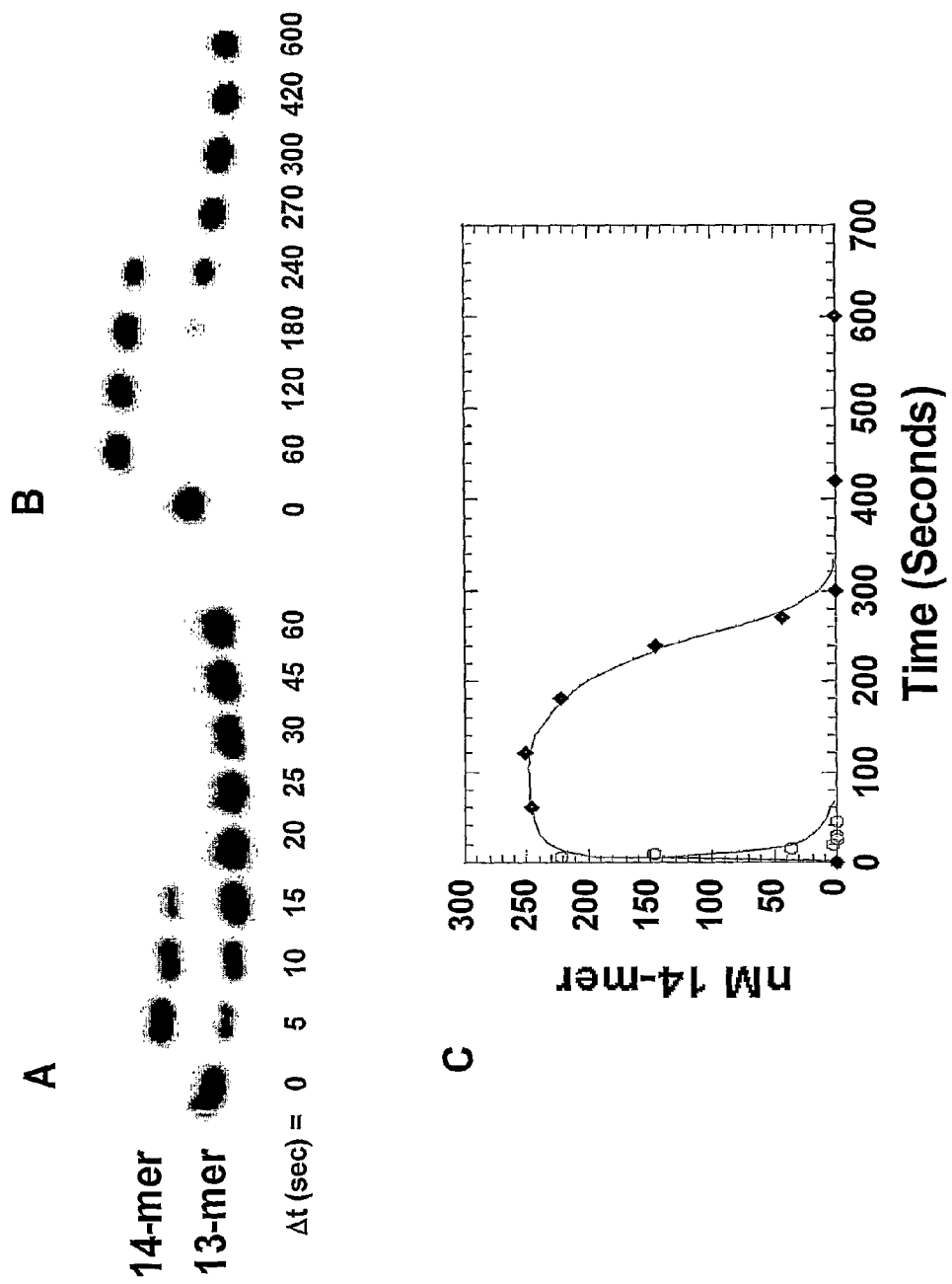

FIG. 16 illustrates representative gel electrophoresis data for the idle turnover of 5-NITP during insertion opposite an abasic site. 1 μM gp43 exo+ was added last to a solution containing 250 nM 5'-labeled 13/20SP-mer, 10 mM Mg2+ and 20 μM NITP (panel A) or 200 μM NITP (panel B). Reactions were terminated by the addition of 200 mM EDTA at time intervals ranging from 5-600 seconds. Nucleotide incorporation and excision were analyzed by denaturing gel electrophoresis. Panel C reports the amount of product formed as a function of time using 5-NITP concentrations of 20 μM (O) and 200 μM ( ), respectively.

Figure 17:
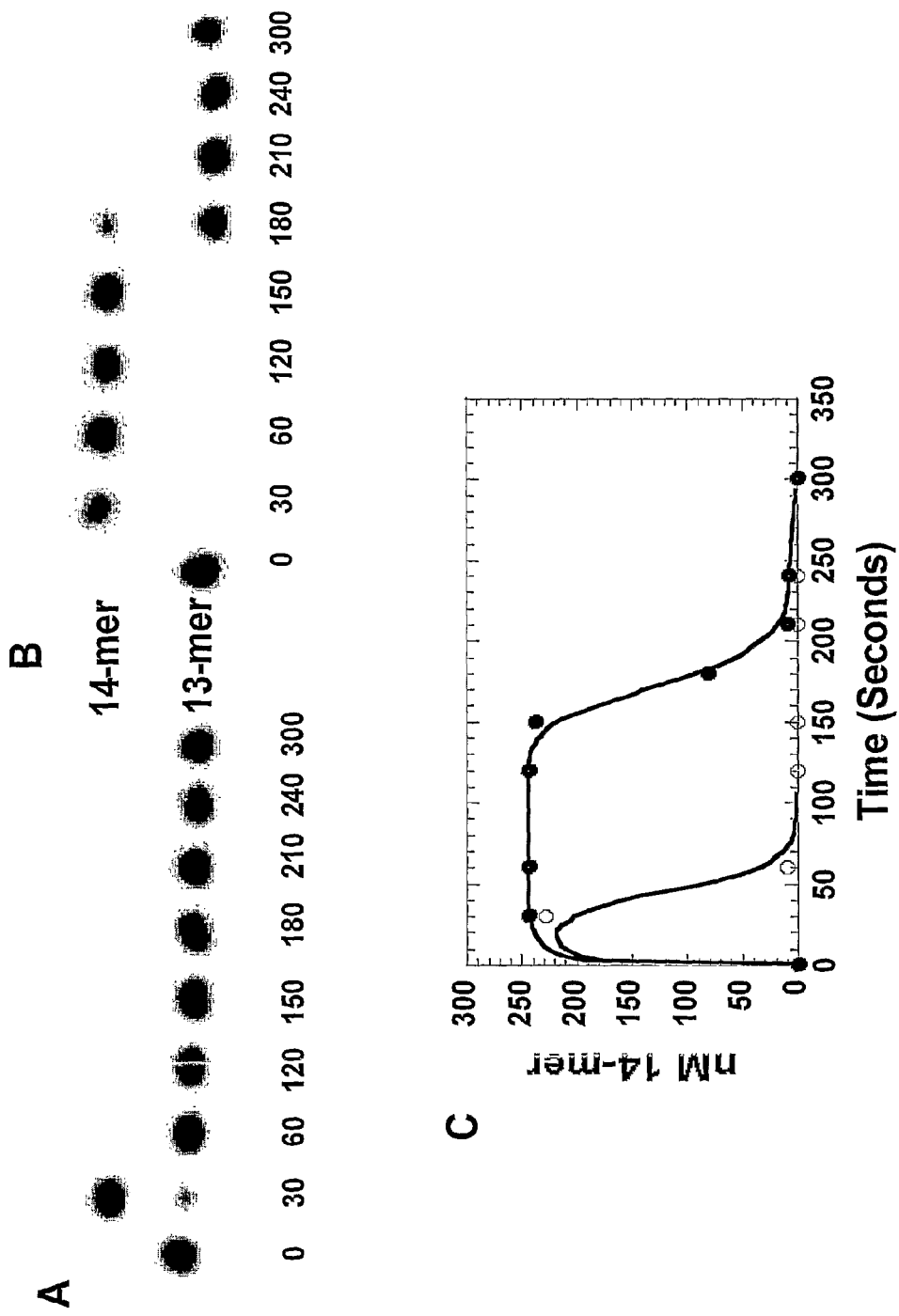

FIG. 17 illustrates a comparison of idle turnover kinetics for 5-NITP and 5-PhITP insertion opposite an abasic site. 1 μM gp43 exo+ was added last to a solution containing 250 nM 5'-labeled 13/20SP-mer, 10 mM Mg$^{2+}$ and 100 μM 5-NITP (panel A) or 100 μM 5-PhITP (panel B). Reactions were terminated by the addition of 200 mM EDTA at time intervals ranging from 30-300 seconds. Nucleotide incorporation and excision were analyzed by denaturing gel electrophoresis. Panel C reports the amount of product formed as a function of time using 100 μM 5-NITP (O) or 100 μM 5-PhITP ( ), respectively.

Figure 18:
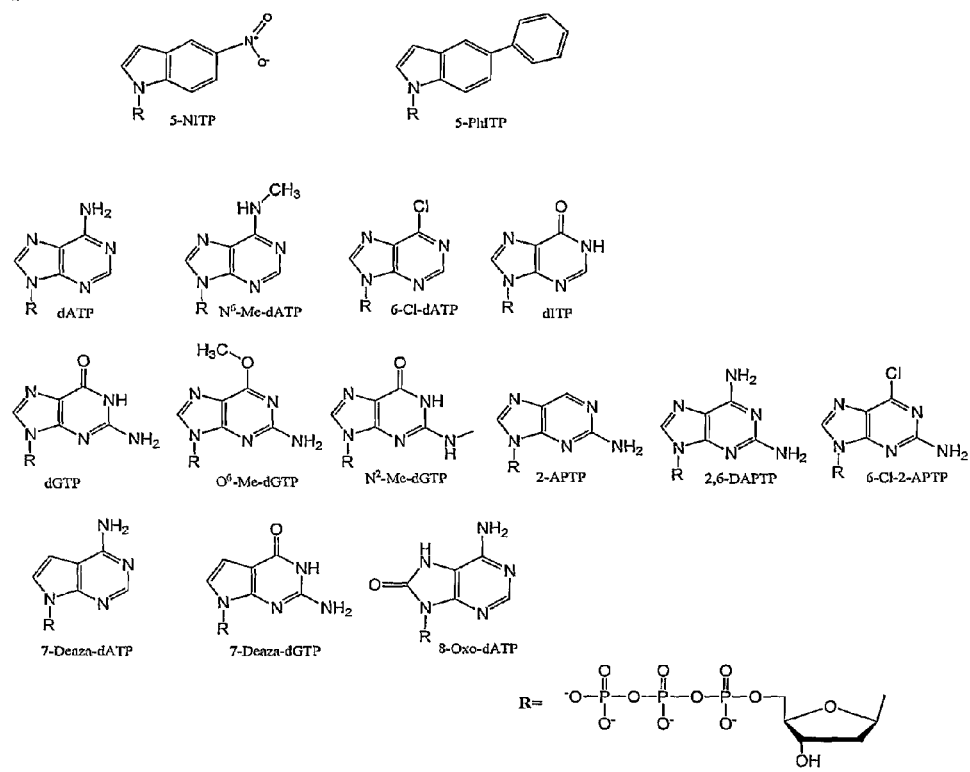

FIG. 18 illustrates (A) Structures of 2' deoxynucleoside triphosphates used or referred to in this study are 5-NITP, 5-PhITP, dATP, N6-methyl dATP, 6-Cl-dATP, dITP, dGTP, O6-methyl-dGTP, N2-methyl-dGTP, 2-APTP, 2,6-DAPTP, 6-Cl-2-APTP, 7-Deaza dATP, 7-Deaza-dGTP, 8-OxodATP. For convenience, R is used to represent the deoxyribose triphosphate portion of the nucleotides. (B) Defined DNA substrates used for kinetic analysis. "X" in the template strand denotes any of the four natural nucleobase or the presence of a tetrahydrofuran moiety.

Figure 19:
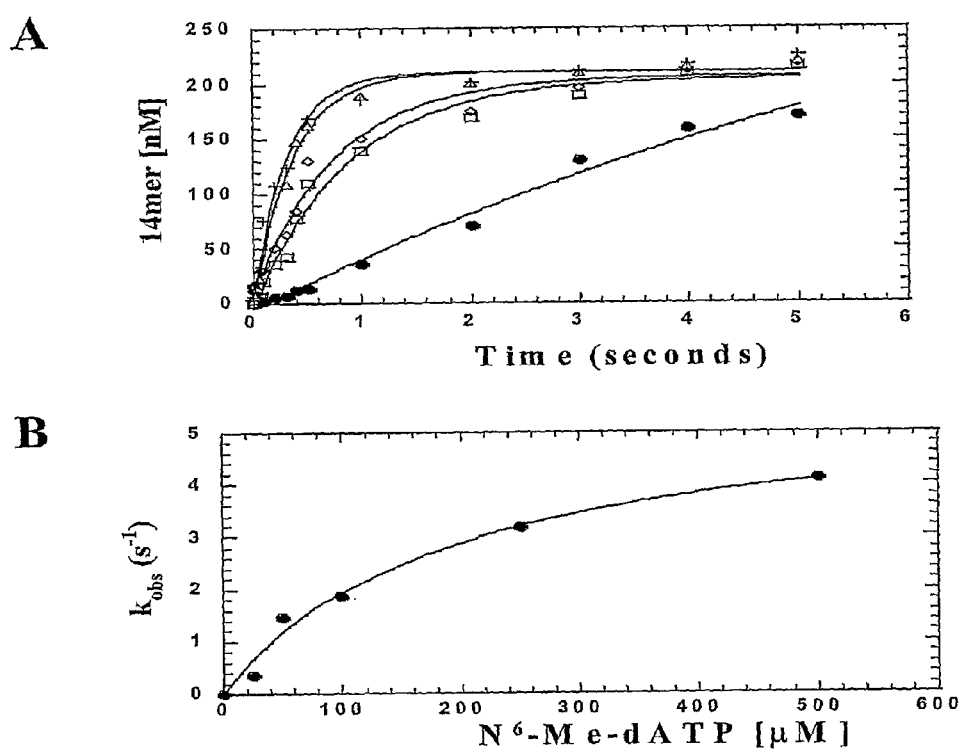

FIG. 19 are plots illustrating (A) Dependency of N$^6$-methyl dATP concentration on the observed rate constant in primer elongation as measured using single turnover conditions. The following concentrations of N$^6$-methyl dATP were used: 25 μM (●), 50 μM (□), 100 μM (◇), 250 μM (+), and 500 μM (Δ). The solid lines represent the fit of each set of data to a single exponential process. (B) The observed rate constants for N$^6$-methyl dATP insertion (●) were plotted against N$^6$-methyl dATP concentration and fit to the Michaelis-Menten equation to determine values corresponding to $K_D$ and $k_{pol}$.

DETAILED DESCRIPTION

The present invention is directed to agents that are potent chain terminators of translesion DNA replication. By acting as chain terminators, these agents are designed to selectively inhibit the propagation of genomic errors caused by translesion DNA synthesis beyond a mispair. The agents can comprise selective non-natural nucleosides that have enhanced binding affinity and faster polymerization to abasic sites on mutagenic DNA than natural nucleosides. The analogs in accordance with the present invention can target and inhibit pro-mutagenic DNA synthesis, a leading culprit in disease development as well as in the development of drug resistance.

The agent in accordance with the present invention can comprise an adenine deoxyribose analog that is selectively inserted opposite an abasic site of damaged or mutagenic DNA, behaves as chain terminators once inserted, and is poorly incorporated into unmodified (i.e., natural) DNA. In an aspect of the invention, the adenine deoxyriboside analog can have the following formula (I):

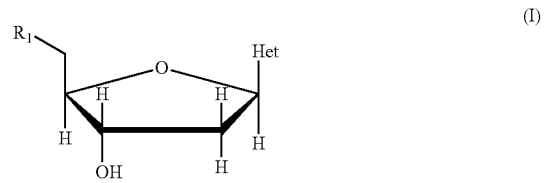

(I)

where Het is a heterocyclic azaindene analog (e.g., purine analogs or indole analogs) selected from the group consisting of:

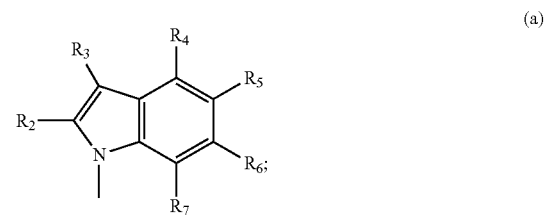

(a)

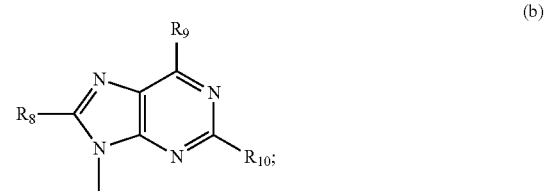

(b)

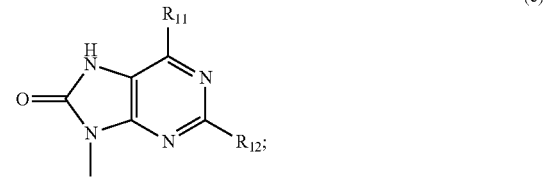

(c)

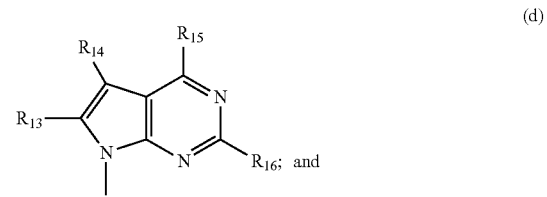

(d)

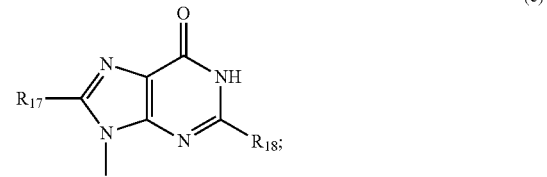

(e)

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$, each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$=$C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), phosphino (—$PH_2$), and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ is other than hydrogen and that where $R_9$ is amino $R_{10}$ is other than hydrogen; a pharmaceutically acceptable salt thereof; or a prodrug thereof.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

The term "prodrug", as used herein, refers to a compound that is converted into the nucleoside on administration in vivo. Nonlimiting examples are pharmaceutically acceptable salts (alternatively referred to as "physiologically acceptable salts"), the 5'-acylated or alkylated derivatives of the active compound, and the 5'-phospholipid and 5'-ether lipid derivatives of the active compound.

Modifications of the active compounds, specifically at the 5'-O positions, can affect the bioavailability and rate of metabolism of the active species, thus providing control over the delivery of the active species. An example of such a modification is a 5'-aminoacid ester, including the L-valinyl ester.

In one subclass of therapeutic agents, the adenine deoxyribose analog can comprise an indolyl deoxyribose analog that is substituted at the 4-position, the 5-position, and/or the 6-position of the indole analog, such as shown in the following formula (II):

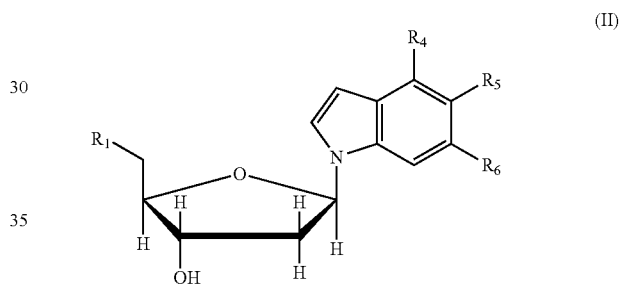

where $R_1$ is OH, monophosphate ($H_2O_3PO—$ or ($O_3PO—)^{2-}$), diphosphate ($H_3(O_3PO)_2—$ or $((O_3PO)_2—)^{3-}$), triphosphate ($H_4(O_3PO)_3—$, $((O_3PO)_3—)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_4$, $R_5$, and $R_6$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho)

substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, and $R_6$, is other than hydrogen; a pharmaceutically acceptable salt thereof; or a prodrug thereof.

Examples of indolyl deoxyribose analogs can have the following formula (III):

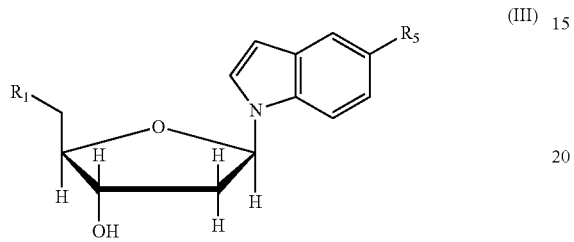

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_5$ is a halo, (e.g., fluoro), amino, nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethenyl, cyclohexenyl), substituted aryl, substituted alkenyl, carboxyl, or nitro; a pharmaceutically acceptable salt thereof; or a prodrug thereof.

In a further aspect of invention, $R_5$ can be a substituent that has a π-electron surface area and density effective to facilitate base stacking interactions and enhance the efficiency for insertion of the agent opposite a non-templating DNA lesion. Examples of such substituents include nitro, ethenyl, cyclohexenyl, phenyl, biphenyl, and napthyl.

The indolyl deoxyribose analogs can be prepared by various synthetic methods. By way of example, 5-$R_5$-indolyl-2' deoxyriboside can be prepared by reacting a riboside with 5-$R_5$-indole as shown in the following reaction scheme:

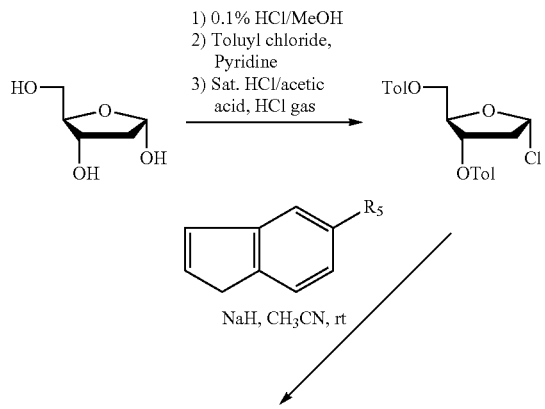

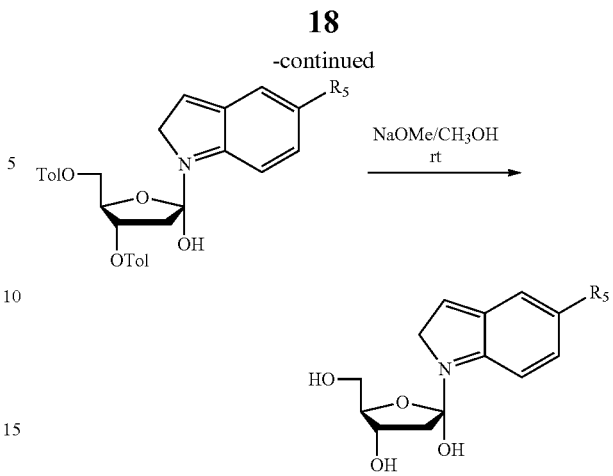

In this example, the riboside can be initially mixed and reacted in a first reaction with (1) HCl/MeOH, (2) toluoyl chloride, pyridine (3) saturated HCl/acetic acid and HCl gas to form 1-chloro-3,5-di-O-toluoyl-2-deoxyriboside. The 1-chloro-3,5-di-O-toluoyl-2-deoxyriboside can then be reacted with 5-$R_5$-indole (e.g., 5-nitro-indole) and NaOMe/Methanol, at room temperature to form 5-$R_5$-indolyl-2' deoxyriboside.

In another subclass of therapeutic agents, the adenine deoxyribose analog can comprise a purine deoxyribose analog that is substituted at the 2 and 6 position of the purine, such as shown in the following formula (IV):

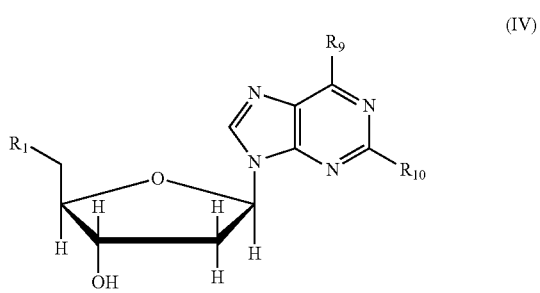

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_9$ and $R_{10}$ each independently represent substituents selected from the group consisting of hydrogen, a halo, (e.g., fluoro), an amine, a substituted amine (HN—CH$_3$), nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro, and where $R_9$ is amino $R_{10}$ is other than hydrogen; a pharmaceutically acceptable salt thereof; or a prodrug thereof.

In a further subclass of therapeutic agents, the adenine deoxyribose analog can comprise a purine deoxyribose analog that is substituted at the 6 position of the purine analog, such as shown in the following formula (V):

(V)

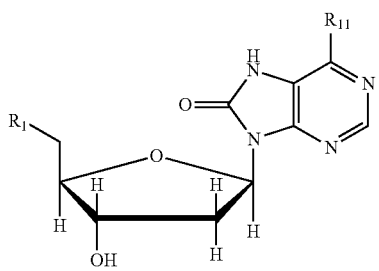

where $R_1$ is OH, monophosphate ($H_2O_3PO—$ or $(O_3PO—)^{2-}$), diphosphate ($H_3(O_3PO)_2—$ or $((O_3PO)_2—)^{3-}$), triphosphate ($H_4(O_3PO)_3—$, $((O_3PO)_3—)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_{11}$ is hydrogen, a halo, (e.g., fluoro), an amine, a substituted amine (HN—CH$_3$), nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro; a pharmaceutically acceptable salt thereof; or a prodrug thereof.

In yet another subclass of therapeutic agents, the adenine deoxyribose analog can comprise a purine deoxyribose analog that is substituted at the 6 position of the purine, such as shown in the following formula (VI):

(VI)

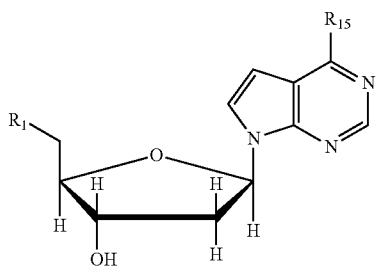

where $R_1$ is OH, monophosphate ($H_2O_3PO—$ or $(O_3PO—)^{2-}$), diphosphate ($H_3(O_3PO)_2—$ or $((O_3PO)_2—)^{3-}$), triphosphate ($H_4(O_3PO)_3—$, $((O_3PO)_3—)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_{15}$ is selected from the group consisting of hydrogen, a halo, (e.g., fluoro), an amine, a substituted amine (HN—CH$_3$), nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro; a pharmaceutically acceptable salt thereof; or a prodrug thereof.

In yet another subclass of therapeutic agents, the adenine deoxyribose analog can comprise a purine deoxyribose analog that is substituted at the 6 position of the purine analog, such as shown in the following formula (VII):

(VII)

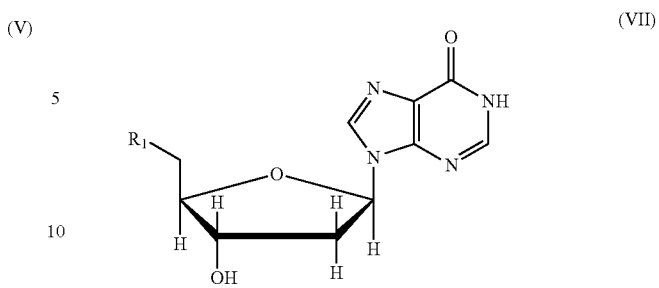

where $R_1$ is OH, monophosphate ($H_2O_3PO—$ or $(O_3PO—)^{2-}$), diphosphate ($H_3(O_3PO)_2—$ or $((O_3PO)_2—)^{3-}$), triphosphate ($H_4(O_3PO)_3—$, $((O_3PO)_3—)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and The adenine deoxyriboside analogs of formula (I-VII) can be used as therapeutic agents for the treatment of a disorder. When used as therapeutic agents, the adenine deoxyriboside analogs of formula (I-VII) can be conveniently formulated into pharmaceutical formulations composed of one or more of the compounds (i.e., adenine deoxyriboside analogs of formula (I-VII)) in association with a pharmaceutically acceptable carrier. (See Remington: The Science and Practice of Pharmacy, 19.sup.th Ed. (Easton, Pa.: Mack Publishing Co., 1995), which discloses typical carriers and conventional methods of preparing pharmaceutical formulations.)

The term "treatment" refers to reduction in severity and/or frequency of symptoms, elimination of symptoms and/or underlying cause, prevention of the occurrence of symptoms and/or their underlying cause, and improvement or remediation of damage. For example, treatment of a patient by administration of a therapeutic agent of the invention encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient by inhibiting or causing regression of a disorder or disease.

The adenine deoxyriboside analogs of formula (I-VII) can also be administered as a stabilized nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed nucleosides to achieve a desired effect.

In one aspect of the invention, the adenine deoxyriboside analogs of formula (I-VII) can be provided as a 5'-hydroxyl lipophilic prodrug. Nonlimiting examples of U.S. patents that disclose suitable lipophilic substituents that can be covalently incorporated into the nucleoside, at the 5'-OH position of the nucleoside or lipophilic preparations, include U.S. Pat. No. 5,149,794; U.S. Pat. No. 5,194,654, U.S. Pat. No. 5,223,263; U.S. Pat. No. 5,256,641; U.S. Pat. No. 5,411,947; U.S. Pat. No. 5,463,092; U.S. Pat. No. 5,543,389; U.S. Pat. No. 5,543, 390; U.S. Pat. No. 5,543,391; and U.S. Pat. No. 5,554,728, all of which are incorporated herein by reference.

The adenine deoxyribose analogs of formula (I-VII) may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the adenine deoxyriboside analogs of formula (I-VII) administered can, of course, be a therapeutically effective amount and can be dependent on the particular active agent, the condition or disorder being treated, the severity of the condition or disorder, the subject's weight, the mode of administration and other pertinent factors known to the prescribing physician. Generally, however, dosage can be in the range of approximately 0.001 µg/mL/day to 100 µg/mL/day, more preferably in the range of about 0.1 µg/mL/day to 10 µg/ml/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets can generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compounds can generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

The adenine deoxyribose analogs of formula (I-VII) are of value in a number of methods. In accordance with the present invention, methods of, and uses in, are provided for significantly inhibiting translesion DNA synthesis without substantially inhibiting normal DNA synthesis. The methods in accordance with the present invention can comprise contacting a population of cells or tissues that include mutagenic DNA with a composition comprising a biologically effective amount of at least one adenine deoxyribose analog of formula (I-VII) under conditions effective to promote chain termination of the damaged DNA without substantially inhibiting normal DNA synthesis.

Further aspects of the invention include the use of the adenine deoxyribose analogs of the formula (I-VII) as an antiviral agent. The adenine deoxyribose analogs of the present invention can be administered to a population cells or tissue infected with a virus and inhibit or interfere with viral nucleic acid replication. The adenine deoxyribose analogs can be administered by contacting the infected cells with a composition comprising a biologically effective amount of at least one adenine deoxyribose analog of formula (I-VII) under conditions effective to inhibit viral replication.

Still further methods and uses of the invention are in analyzing the biological roles of the adenine deoxyribose analogs of formula (I-VII). In the method, a biological composition or tissue that comprises a population of cells that include mutagenic DNA are contacted with a composition comprising a biologically effective amount of at least of at least one of the therapeutic agents. The effect of the therapeutic agent on translesion DNA synthesis is then determined The foregoing methods and uses can be performed in vitro and in vivo. In the latter case, where the tissues or cells are located within an animal, at least one of the adenine deoxyribose analogs of formula (I-VII) can be administered to the animal as a form of therapy. Where populations of cells with potentially mutagenic DNA are maintained ex vivo, the present invention has utility in drug discovery programs.

"Biologically effective amounts", in terms of each of the foregoing inhibitory methods are therefore amounts of the at least one of adenine deoxyribose analog of formula (I-VII) effective to inhibit translesion DNA synthesis, without substantially inhibiting normal DNA synthesis; and without being cytotoxic to the cells.

In a further aspect of the invention, the adenine deoxyribose analogs of formula (I-VII) can be used in combination and adjunctive therapies for treating mammalian diseases, such as in therapies in which potentially promutagenic therapeutic agents are administered to treat the disease.

The phrase "combination therapy" embraces the administration of the adenine deoxyribose analogs of formula (I-VII), and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In an aspect of the invention, the therapeutic agent administered in combination therapy with the adenine deoxyribose analogs of formula (I-VII) can comprise cytoxic agents that can potentially compromise the integrity of nucleic acids associated with DNA replication and cellular proliferation (i.e., DNA damaging agents). The adenine deoxyribose analogs of formula (I-VII) in accordance with the present invention are selective for damaged DNA and can potentiate the cytotoxic effects of the DNA damaging agents. Additionally, since the adenine deoxyribose analogs of formula (I-VII) in accordance with the present invention behave as chain terminators, they can prevent propagation of genomic errors caused by the DNA damaging agents and would thus limit the development of resistance caused by replication of the mutated DNA. Moreover, the use of these therapeutic agents should not affect enzymatic phosphorylation, in contrast to other chain-terminators that have ribose modifications.

In another aspect of the invention, the therapeutic agents administered in combination therapy with the adenine deoxyribose analogs of formula (I-VII) can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the adenine deoxyribose analog of formula (I-VII) consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the analogs of the present invention consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the analogs of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the analogs of the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the analogs of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the anaologs of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The foregoing treatment methods and uses can generally involve the administration of a pharmaceutically effective composition of the adenine deoxyribose analogs of formula (I-VII) to the animal or patient systemically, such as by transdermal, intramuscular, intravenous injection and the like. However, any route of administration that allows the therapeutic agent to localize to the site or sites of the cells, which are being treated by the DNA damaging agent can be acceptable. Therefore, other suitable routes of delivery include oral, rectal, nasal, topical, and vaginal. U.S. Pat. No. 5,712,291, is incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the adenine deoxyribose analogs of formula (I) therapeutic agents in an amount(s) and for a period of time(s) effective to inhibit translesion DNA synthesis.

The "therapeutically effective amounts" for use in the invention are amounts adenine deoxyribose analogs of formula (I-VII) effective to inhibit translesion DNA synthesis and to potentiate the cytotoxic effects of the DNA damaging agent. Such effects are achieved without substantially inhibiting normal DNA synthesis in normal, healthy cells or tissues; and exerting negligible or manageable adverse side effects on normal, healthy cell or tissues of the animal or patient.

The adenine deoxyribose analogs of formula (I-VII) in accordance with the present invention can allow the combination therapeutic agents and therapies of the present invention to be administered at a low dose, that is, at a dose lower than has been conventionally used in clinical situations.

A benefit of lowering the dose of the combination therapeutic agents and therapies of the present invention administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the therapeutic agents can be formulated as separate compositions which are given at the same time or different times, or the therapeutic agents can be given as a single composition.

In a still a further aspect of the invention, the adenine deoxyribose analogs of formula (I-VII) can be used as diagnostic agents to monitor the formation of DNA damage by anti-neoplastic agents and/or chemotherapeutic agents. By way of example, adenine deoxyribose analogs having fluorescent properties, such as 5-PHITP, can be used as a noninvasive probe in flow cytometry techniques to monitor the formation of DNA damage caused by chemotherapeutic agents.

Flow cytometry provides a way to measure the biochemical properties of thousands of individual cells in a liquid suspension. The speed at which a flow cytometer can do this is unparalleled, counting as many as 15,000 cells/sec while still looking at each cell individually. Histograms can also be used to display data from flow cytometry experiments. In these plots the X-axis shows the intensity of the detected signal and the Y-axis measures the number of events (cells) counted. Histograms often display the output of two (or more) samples using a single fluorochrome. In an experiment determining the presence or absence of a particular cell marker or a relative increase or decrease of a marker after experimental treatment, a histogram shows the shift in the fluorescence intensity of the sampled cells.

In a diagnostic method using an adenine deoxyribose analog having fluorescent properties, such as 5-PHITP, a patient receives a fixed dose of anti-neoplastic or chemotherapeutic agent(s). After a fixed period of time, an aliquot of blood is removed. This sample is treated with the adenine deoxyribose analog having fluorescent properties, such as 5-PHITP, and analyzed by flow cytometry techniques to determine the amount of the adenine deoxyribose analog that has been incorporated into the DNA of all cells. The amount of nucleotide incorporation is directly correlated with the amount of DNA damaged caused by the initial treatment of chemotherapeutic agent. Based upon results of this assay, the clinician will be able to rationally modify the dose based upon empirical evidence of DNA damage. The speed of this assay will allow the clinician to rapidly modify the dose to improve the likelihood of a good patient response.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

The Use of Nonnatural Nucleotides to Probe the Contributions of Shape Complementarity and π-Electron Surface Area During DNA Polymerization Hydrogen-bonding, base-stacking, and solvation/desolvation contributions play significant roles in maintaining the stability of nucleic acid. Perhaps the most elusive question in nucleic acid metabolism is the extent to which each of these molecular forces is efficiently utilized by DNA polymerases during replication. The individual contributions of these forces during the polymerization process have been difficult to dissect due to the paradoxical nature of the nucleobases that compose DNA. Specifically, in addition to base-stacking capabilities, each nucleobase contains functional groups capable of hydrogen-bond interactions with water as well as with other acceptor-donor groups on other nucleobases.

Several laboratories have attempted to deconvolute this paradox by monitoring the kinetics of insertion of nonnatural nucleosides devoid of classical hydrogen bonding groups. The collective results of these studies indicate that the presence of hydrogen-bonding groups is not an absolute requirement for the stable incorporation of a nonnatural nucleobase into DNA. In most instances, a nonnatural nucleoside is preferentially inserted opposite the complementarity partner of its isosteric progenitor. This kinetic phenomenon was originally interpreted to reflect the contributions of geometrical constraints of the formed base pair. However, other molecular forces such as base stacking and desolvation cannot be eliminated since they also play significant roles during DNA polymerization.

To evaluate the contributions of these parameters, we have examined the dynamics of nucleoside insertion opposite an abasic site, a nontemplating DNA lesion devoid of classical hydrogen-bonding potential as well as normal size/shape constraints. Many DNA polymerases such as the eukaryotic polymerases pol α and pol δ, the Klenow fragment from *E. coli*, HIV reverse transcriptase, and gp43 from bacteriophage T4 preferentially insert dAMP (and dGMP to a lesser extent) opposite an abasic site. An attractive mechanism to explain this kinetic phenomenon is that polymerization efficiency is influenced more by the basestacking capabilities of the incoming dNTP rather than its size or shape. The validity of this hypothesis has been strengthened by the favorable enzymatic insertion of 5-NIMP opposite an abasic site. Although 5-nitro-1-indolyl-2'-deoxyribose-5'-triphosphate (5-NITP) does not possess "classical" hydrogen-bonding acceptor/donor groups, it has enhanced base-stacking capabilities compared to natural dNTPs. Remarkably, the catalytic efficiency for 5-NIMP insertion opposite the lesion is 1000-fold greater than that measured for the insertion of dAMP. The nitro moiety appears to play an important role since replacement with —H reduces the catalytic efficiency for nucleoside insertion by ~2300-fold. Although binding affinity is perturbed slightly, the major effect of this substitution is the 450-fold reduction in the rate of the conformational change step that corresponds to a change in relative free energy ($\Delta\Delta G$) of 3.62 kcal/mol. This energetic difference was proposed to arise through base-stacking interactions mediated between the overlapping π-electron densities of the conjugated indole nucleoside with the polymerase and DNA. However, other forces such as desolvation as well as size and shape complementarity cannot be unambiguously refuted based solely upon these data.

Figure 1:
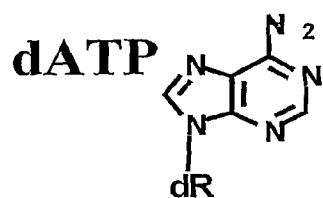
FIG. 1 illustrates (A) Structures of 2'-deoxynucleoside triphosphates used or referred to are dATP, 5-NITP, Ind-TP, 5-PhITP, 5-FITP, and 5-AITP. For convenience, dR is used to represent the deoxyribose triphosphate portion of the nucleotides. (B) Defined DNA substrates used for kinetic analysis. "X" in the template strand denotes any of the four natural nucleobase or the presence of a tetrahydrofuran moiety designed to mimic an abasic site.
Figure 1:
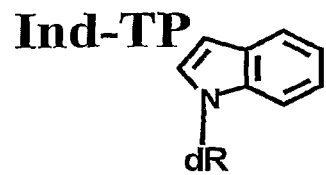
Figure 1:
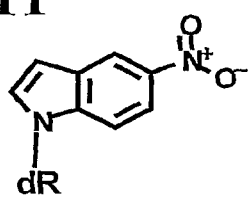
Figure 1:
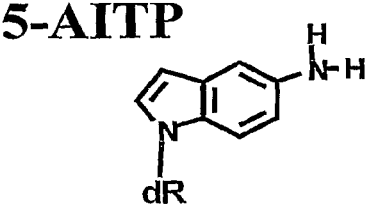
Figure 1:
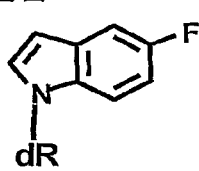
Figure 1:
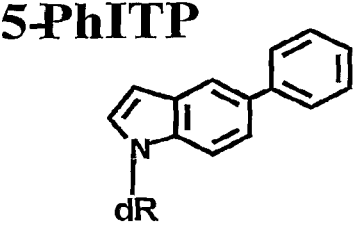

We have further evaluated the contribution of base stacking, desolvation, shape, and dipole moment toward translesion DNA synthesis by measuring the insertion of various 5-substituted indolyl-2'-deoxyribose triphosphates displayed in FIG. 1A. Of the analogues examined, 5-phenyl-indolyl-2'-deoxyribose triphosphate displays the highest catalytic efficiency for insertion opposite the abasic site. The generated structure-activity relationships provide evidence that π-electron surface area rather than size, shape, or desolvation capabilities is the most important factor for insertion opposite an abasic lesion. When tested for insertion opposite templating nucleobases, the expected correlation between insertion efficiency and shape complementarity of the formed base pair is not observed. Collectively, these results suggest that steric fit plays a minimal role during polymerization catalyzed by the bacteriophage T4 DNA polymerase.

Methods and Materials

Materials

[γ-$^{32}$P]ATP was purchased from M. P. Biomedical (Irvine, Calif.). Unlabeled dNTPs (ultrapure) were obtained from Pharmacia. Magnesium acetate and Trizma base were from Sigma. Urea, acrylamide, and bisacrylamide were from Aldrich. Oligonucleotides, including those containing a tetrahydrofuran moiety mimicking an abasic site, were synthesized by Operon Technologies (Alameda, Calif.). Single-stranded and duplex DNA were purified and quantified. All other materials were obtained from commercial sources and were of the highest available quality. The exonuclease-deficient mutant of gp43 (Asp-219 to Ala mutation) was purified and quantified.

Tributylammonium pyrophosphate was purchased from Sigma. 5-Fluoro-indole, 1-chloro-2-deoxy-3,5-di-O-p-toluoyl-α-D-erythro-pentofuranose, ethyl acetate, hexane, methanol, dichloromethane, phosphoryl oxychloride, dimethyl formamide, and tributylamine were purchased from ACROS. Trimethyl phosphate and tributylamine were dried over 4 Å molecular sieves. DMF was distilled from ninhydrin and stored in 4 Å molecular sieves.

All NMR spectra were record in a Gemini-300 FT NMR spectrometer. Proton chemical shifts are reported in ppm downfield from tetramethylsilane. Coupling constants (J) are reported in hertz (Hz). $^{31}$P NMR spectra were taken in $D_2O$ in the presence of 50 mM Tris (pH 7.5) and 2 mM EDTA. Phosphoric acid (85%) was used as external standard. Ultraviolet quantification of triphosphate was performed on Beckman DU-70. High-resolution electrospray mass spectrometry (negative) was performed on Ionspec HiRES ESI-FTICRMS at the University of Cincinnati.

Synthesis of 5-Fluoro-indole-2'-deoxyribofuranoside 5'-Triphosphate (5-FITP)

The 5-fluoro-indole-2'-deoxynucleoside was converted to the triphosphate form first by reaction with phosphoryl oxychloride in the presence of proton sponge and trimethyl phosphate. After 2 h, the reaction was simultaneously treated with a 0.5 M solution of tributylammonium pyrophosphate and tributylamine in dimethyl formamide. The desired compound was purified by semipreparative reverse-phase HPLC (300 pore size C-18 column from Vydac, 10 mm×250 mm) with mobile phase buffer A=0.1 M TEAB and buffer B=35% ACN in 0.1 M TEAB, using a linear gradient from 45% to 80% B within 18 min at a flow rate of 2.3 mL/min. The desired triphosphate was eluted at 73% B (14 min retention time). After concentration and evaporation, the final product was dissolved and stored in 10 mM TrisHCl, pH 7.5, and 1 mM EDTA. The concentration was determined using an extinction coefficient of 6142 $M^{-1}$ $cm^{-1}$ for the free nucleoside. The yield of phosphorylation was 20%. 1-(3,5-Di-O-p-toluoyl-2-deoxy-β-D-erythro-pentafuranosyl)-5-fluoro-indole: H NMR (DMSO) 2.37 (3H, s, $CH_3$), 2.40 (3H, s, $CH_3$), 2.69 (1H, m, 2'-H), 2.96 (1H, m, 2'-H), 4.45-4.65 (3H, m, 5'-H, 4'-H), 5.60-5.70 (1H, m, 3'-H), 6.51 (1H, d, J) 3.3 Hz, 3-H), 6.59 (1H, t, J) 6.0 Hz, 1'-H), 6.87-6.94 (1H, m, Ar), 7.30-7.38 (5H, m, Ar), 7.66-7.70 (2H, m, Ar), 7.88 (2H, d, J) 8 Hz, Ar), 7.99 (2H, d, J) 8 Hz, Ar). 1-(2-Deoxy-β-D-erythro-pentafuranosyl)-5-fluoro-indole: H NMR (DMSO) 2.25 (1H, m, 2'-H), 2.55 (1H, m, 2'-H), 3.45-3.55 (2H, m, 5'-H), 3.83-3.88 (1H, m, 4'-H), 4.32-4.34 (1H, m, 3'-H), 4.90 (1H, m, 5'-OH), 5.30 (1H, m, 3'-OH), 6.34 (1H, t, J) 6.9 Hz, 1'-H), 6.45 (1H, d, J) 3.4 Hz, 3-H), 6.90 (1H, m, Ar), 7.32 (1H, m, Ar), 7.57-7.66 (2H, m, Ar). 1-(2-Deoxy-β-D-erythropentafuranosyl)-5-fluoro-indole triphosphate (5-FITP): $^{31}$P NMR (ppm) ($D_2O$/Tris/EDTA) γ-P −5.75 (d); α-P −10.22 (d); β-P −21.50 (t). HiRes ESI-MS (−): Calculated mass spec (formula $C_{13}H_{16}FNO_{12}P_3$ for M-H)=489.9869. Experimental mass spec=490.0164.

Synthesis of 5-Phenyl-indole-2'-Deoxyribofuranoside 5'-Triphosphate (5-PhITP)

5-Phenyl-indole was synthesized using established protocols. 1-(2-Deoxy-β-D-erythropentafuranosyl)-5-phenyl-indole was prepared by the method described for deprotection of fluoro-indole nucleoside. The overall yield of the reaction was 70%. 1-(2-Deoxy-β-Derythro-pentafuranosyl)-5-phenyl-indole triphosphate (PhITP) was prepared starting with 5-phenyl-indole-2'-deoxynucleoside. The residue was purified by preparative reverse phase HPLC (300 pore size C-18 column from Vydac, 22 mm, 250 mm) with mobile phase buffer A=0.1 M TEAB and buffer B=35% ACN in 0.1 M TEAB. The reaction mixture was purified using 80% B without gradient. The product was eluted at 24 min retention time with a flow rate of 4.5 mL/min. The final product was dissolved and stored in 10 mM TrisHCl, pH 7.5. The concentration of nucleotide was determined using the extinction coefficient of 35 379 $M^{-1}$ $cm^{-1}$ determined for the free nucleoside. 1-(3,5-Di-O-ptoluoyl-2-deoxy-β-D-erythro-pentafuranosyl)-5-phenyl-indole: H NMR ($CDCl_3$) 2.41, (3H, s, $CH_3$), 2.45 (3H, s, $CH_3$), 2.70 (1H, m, 2'-H), 2.78 (1H, m, 2'-H), 4.5-4.65 (3H, m, 5'-H, 4'-H), 5.72 (1H, m, 3'-H), 6.58 (1H, d, J) 3.3 Hz, 3-H), 6.62 (1H, t, J) 7.2 Hz, 1'-H), 7.31-7.50 (8H, m, Ar), 7.60-8.06 (9H, m, Ar). 1-(2-Deoxy-β-D-erythro-pentafuranosyl)-5-phenyl-indole: H NMR (DMSO) 2.25 (1H, m, 2'-H), 2.55 (1H, m, 2'-H), 3.52-3.62 (2H, m, 5'-H), 3.83-3.88 (1H, m, 4'-H), 4.34-4.41 (1H, m, 3'-H), 4.90 (1H, t, J) 5 Hz, 5"-OH), 5.30 (1H, d, J) 4 Hz, 3'-OH), 6.40 (1H, t, J) 6.2 Hz, 1'-H), 6.56 (1H, d, J) 3.3 Hz, 3-H), 7.30-7.33 (1H, m, Ar), 7.41-7.45 (3H, m, Ar), 7.61-7.67 (4H, m, Ar), 7.81 (1H, d, J) 2 Hz, Ar). 1-(2-Deoxy-β-D-erythro-pentafuranosyl)-5-phenyl-indole triphosphate (PhITP) $^{31}$P NMR (ppm) ($D_2$O/Tris/EDTA) γ-P −5.65 (d); α-P −10.35 (d); β-P −21.46 (t). HiRes ESI-MS (−): Calculated mass spec (formula $C_{19}H_{21}N_1O_{12}P_3$ for M-H)=548.0277. Experimental mass spec=548.0242.

Synthesis of 5-Amino-Indole-2'-Deoxyribofuranoside 5"-Triphosphate (5-AITP)

Amino-indole triphosphate was prepared from 5-nitro-indole triphosphate by hydrogenation reaction. The extinction coefficient for 5-amino-indole is 5830 $M^{-1}$ $cm^{-1}$ at 270 nm.

Enzyme Assays

The assay buffer used in all kinetic studies consisted of 25 mM Tris-OAc (pH 7.5), 150 mM KOAc, and 10 mM 2-mercaptoethanol. All assays were performed at 25° C. Polymerization reactions were monitored by analysis of the products on 20% sequencing gels. Gel images were obtained with a Packard PhosphorImager using the OptiQuant software supplied by the manufacturer. Product formation was quantified by measuring the ratio of $^{32}$P-labeled extended and nonextended primer. The ratios of product formation are corrected for substrate in the absence of polymerase (zero point). Corrected ratios are then multiplied by the concentration of primer/template used in each assay to yield total product. All concentrations are listed as final solution concentrations.

The kinetic parameters, $k_{cat}$, $K_m$, and $k_{cat}/K_m$, for each nonnatural nucleotide were obtained by monitoring the rate of product formation using a fixed amount of gp43 (50 nM) and DNA substrate (1000 nM) at varying concentrations of nucleotide triphosphate (0.01-1 mM). Aliquots of the reaction were quenched into 0.5 M EDTA, pH 7.4, at times ranging from 5 to 600 s. Samples were diluted 1:1 with sequencing gel loading buffer and products were analyzed for product formation by denaturing gel electrophoresis. In all cases, steady-state rates were obtained from the linear portion of the time course. Data obtained for steady-state rates in DNA polymerization measured under pseudo-first-order reaction conditions were fit to eq 1:

$$y = mt + b \quad (1)$$

where m is the slope of the line, b is the y-intercept, and t is time. The slope of the line is equivalent to the rate of the reaction, v, and has units of nM/s. Data for the dependency of v as a function of dXTP concentration were fit to the Michaelis-Menten equation:

$$v = V_{max}[dXTP]/K_m + [dXTP] \quad (2)$$

where v is the rate of the reaction, $V_{max}$ is the maximal velocity, $K_m$ is the Michaelis constant for dXTP, and [dXTP] is the concentration of nonnatural nucleotide substrate. $k_{cat}$ is defined as $V_{max}/[gp43]$.

Pre-Steady-State Nucleotide Incorporation Assays

A rapid quench instrument (KinTek Corporation, Clarence, Pa.) was used to monitor the time course in 5-PhIMP insertion using 13/20SP-mer or 13/20T-mer as the DNA substrate. A preincubated solution of 75 nM gp43 exo⁻ polymerase and 2000 nM 5'-labeled DNA (final concentrations) was mixed with an equal volume of a solution containing 10 mM magnesium acetate and 10 μM 5-PhITP (final concentrations) in the same reaction buffer. The reaction was then terminated at various times by the addition of 350 mM EDTA. Polymerization products were analyzed as described above. Data for each time course were fit to eq 3 defining a burst in product formation followed by a steady-state rate.

$$y = Ae^{-kt} + Bt + C \quad (3)$$

where A is the burst amplitude, k is the observed rate constant for initial product formation, B is the steady-state rate, t is time, and C is a defined constant.

In some instances, experiments were performed using single turnover reaction conditions. One thousand nanomolar gp43 exo⁻ was incubated with 250 nM DNA in assay buffer containing EDTA (100 μM) and mixed with variable concentrations of nucleotide analogue (5-500 μM) and 10 mM magnesium acetate. The reactions were quenched with 500 mM EDTA at variable times (0.005-10 s) and analyzed as described above. Data obtained for single turnover DNA polymerization assays were fit to eq 4.

$$y = Ae^{-kt} + C \quad (4)$$

where A is the burst amplitude, k is the observed rate constant for initial product formation, t is time, and C is a defined constant. Data for the dependency of $k_{obs}$ as a function of dNTP concentration was fit to the Michaelis-Menten equation (eq 2) to provide values corresponding to $k_{pol}$ and $K_D$.

TABLE 1

Summary of Kinetic Rate and Equilibrium Constants Measured for the Insertion of 5-Substituted Indolyl-2'-deoxyriboside Triphosphates Opposite an Abasic Site

| analogue | $k_{pol}$ ($s^{-1}$) | $K_D$ (μM) | $k_{pol}/K_D$ ($M^{-1}$ $s^{-1}$) |
|---|---|---|---|
| 5-PhITP[a] | 53 ± 4 | 14 ± 3 | 3.8 × 10⁶ |
| 5-FITP[b] | 0.30 ± 0.03 | 152 ± 41 | 2.0 × 10³ |
| 5-AITP[b] | 0.17 ± 0.01 | 255 ± 43 | 0.7 × 10³ |

TABLE 1-continued

Summary of Kinetic Rate and Equilibrium Constants Measured
for the Insertion of 5-Substituted Indolyl-2'-deoxyriboside
Triphosphates Opposite an Abasic Site

| analogue | $k_{pol}$ (s$^{-1}$) | $K_D$ (µM) | $k_{pol}/K_D$ (M$^{-1}$ s$^{-1}$) |
|---|---|---|---|
| 5-NITP[c] | 126 ± 6 | 18 ± 3 | 7.0 × 10$^6$ |
| IndTP[d] | 0.28 ± 0.07 | 145 ± 10 | 1.9 × 10$^3$ |

[a]The kinetic parameters, $k_{pol}$, $K_D$, and $k_{pol}/K_D$, were obtained under single turnover conditions using 1 µM gp43exo−, 250 nM 13/20SPmer, and 10 mM Mg$^{2+}$ at varying concentrations of nonnatural nucleotide triphosphate (0.0025-0.100 mM).
[b]The kinetic parameters were obtained under pseudo-first-order reaction conditions using 50 nM gp43exo−, 1 µM 13/20SP-mer, and 10 mM Mg$^{2+}$ at varying concentrations of nonnatural nucleotide triphosphate (0.01-1 mM).

Results

Steady-State Kinetic Parameters for Insertion Opposite an Abasic Site

Figure 2:
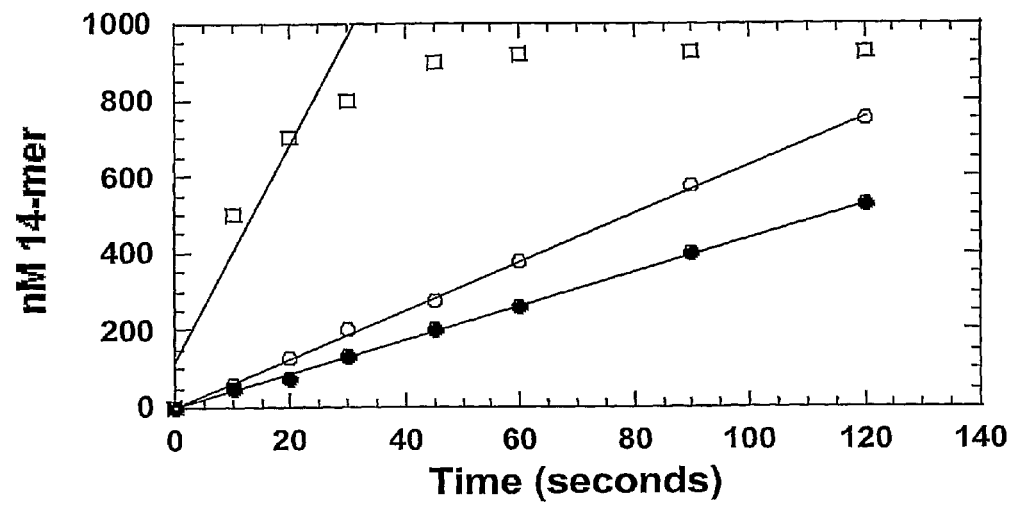
FIG. 2 is a plot illustrating time courses in the incorporation of 250 μM 5-AITP (●), 150 μM 5-FITP (○), and 15 μM 5-PhITP (□) opposite an abasic site. All reactions were performed using pseudo-first-order reaction conditions (50 nM gp43 exo−/1000 nM 13/20SP-mer). Extrapolation of the time course back to time zero does not reveal a burst in product formation using 5-AITP or 5-FITP. In contrast, an apparent burst in primer elongation is observed using a significantly lower concentration of 5-PhITP.

The kinetic parameters, $k_{pol}$, $K_D$, and $k_{pol}/K_D$ for each substituted indole triphosphate during incorporation opposite an abasic site were obtained by monitoring the rate of product formation at varying nucleotide concentrations (0.01-1 mM). Using 5-FITP and 5-AITP, we obtained linear rates in product formation at all concentrations tested. Extrapolation of the time course back to time zero does not reveal a burst in primer elongation under pseudo-first-order reaction conditions (FIG. 2). Furthermore, burst kinetics were not observed using a higher concentration of gp43 (100 or 200 nM (data not shown)). The lack of an observed "burst" in product formation under pseudo-first-order reaction conditions suggests that phosphoryl transfer or a kinetic step prior to phosphoryl transfer is rate-limiting for enzyme turnover. Regardless, the measured rates of nucleotide incorporation were plotted as a function of dXTP concentration and displayed saturation kinetics (data not shown). Values of $k_{pol}$, $K_D$, and $k_{pol}/K_D$ were obtained from the fit of the data to the Michaelis-Menten equation and are summarized in Table 1.

Linear rates in product formation were also observed with 5-PhITP as the nonnatural analogue. However, an apparent burst in primer elongation was observed when 5-PhIMP is inserted opposite the nontemplating lesion (FIG. 2). Both the burst in primer elongation and the steady-state rate in product formation were independent of 5-PhITP concentration (data not shown). Collectively, these data are consistent with a mechanism in which a kinetic step after phosphoryl transfer is rate-limiting for enzyme turnover.

Transient Kinetic Analysis of 5-PhITP Incorporation Opposite an Abasic Site

Figure 3:
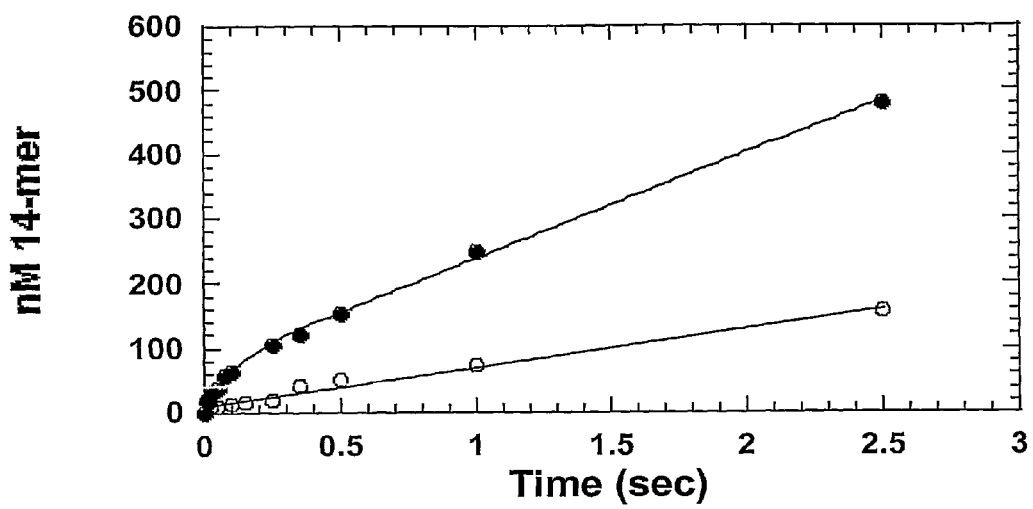
FIG. 3 is a plot illustrating pre-steady-state time courses for the insertion 5-PhIMP opposite an abasic site ( ) or opposite T (○). Assays monitoring translesion DNA synthesis were performed mixing a pre-incubated solution of 75 nM gp43 exo− and 2 μM 5'-labeled 13/20SP-mer with an equal volume of a pre-incubated solution of 10 mM MgAcetate and 10 μM 5-PhITP in the same reaction buffer (final concentrations).

The results of the manual quenching experiments suggest that the incorporation of 5-PhITP opposite the abasic site is extremely rapid. Therefore, experiments were performed using a rapid-quench instrument to unequivocally detect the presence of a "burst" in primer elongation. As illustrated in FIG. 3, the time course for 5-PhITP incorporation opposite an abasic site is biphasic as characterized by a rapid initial burst in 14-mer formation followed by a second, slower phase in primer elongation. The second, linear phase of the time course represents release of gp43 from extended DNA and subsequent turnover of remaining 13/20SP-mer. When 5 µM 5-PhITP is used, the observed rate constant of the burst phase is 9.1±2.1 s$^{-1}$ while the $k_{cat}$ value is 2.2 (0.5 s$^{-1}$. The amplitude of the burst phase is equal to the amount of gp43 used in the reaction (75 nM). The detection of a stoichiometric burst even at low concentrations of 5-PhITP suggests that the nonnatural nucleotide binds very tightly to the polymerase/DNA complex such that the gp43/DNA/5-PhITP complex partitions to product (gp43+DNA$_{n+1}$+PP$_i$) rather than collapsing back to gp43/DNA+5-PhITP. Alternatively, the stoichiometric burst amplitude can be explained if the phosphoryl transfer step is favorable such that nucleotide binding and incorporation are driven to completion. To evaluate these potential mechanisms, the kinetic dissociation constant, $K_D$, as well the maximal polymerization rate, $k_{pol}$, for the insertion of 5-PhIMP were measured.

Measurements of $k_{pol}$ and $K_D$ for 5-PhITP Incorporation Opposite an Abasic Site Single turnover conditions were then employed to accurately measure the $K_D$ and $k_{pol}$ values for the insertion of 5-PhIMP opposite the abasic site. Since the concentration of polymerase is maintained in excess versus DNA substrate, these experiments alleviate complications arising from any kinetic step after phosphoryl transfer. This allows for the measurement of the kinetic steps reflecting initial ground state binding of 5-PhITP, the conformational change prior to phosphoryl transfer, and phosphoryl transfer itself. All time courses were generated using a rapid quench instrument.

Representative data for the concentration dependency of 5-PhITP on the rate constant in primer elongation are presented in FIG. 4A. All time courses were fit to the equation for a single-exponential process to define $k_{obs}$, the rate constant in product formation. The plot of $k_{obs}$ versus 5-PhITP concentration is hyperbolic (FIG. 4B) from which values of $k_{pol}$=53±4 s$^{-1}$ and $K_{D\,5\text{-}PhITP}$=14±3 µM were obtained. It was observed earlier that when 5 µM 5-PhITP was used, a burst rate ($k_{obs}$) of 9 s$^{-1}$ was measured for incorporation opposite the abasic site under pseudo-first-order reaction conditions. This value is significantly less than the reported $k_{pol}$ value of 53 s$^{-1}$ measured using single turnover reaction conditions. The lower value of 9 s$^{-1}$ reflects the fact that the concentration of 5 µM 5-PhITP is below the $K_D$ value of 5-PhITP. To validate this conclusion as well as to demonstrate consistency between experiments performed using pseudo-first-order versus single turnover conditions, we applied these rate and dissociation constants to the Michealis-Menten equation ($k_{obs}=k_{pol}$[5-PhITP]/($K_D$+[5-PHITP])). Using a $k_{pol}$ value of 53 s$^{-1}$ and a $K_D$ of 14 µM, we calculate that the $k_{obs}$ value using 5 µM 5-PhITP is 14 s$^{-1}$ and is in good accord with the measured value of 9 s$^{-1}$ measured independently under pseudo-first-order reaction conditions. Values are summarized in Table 1.

The Effects of Acid Versus EDTA Quenching on the Kinetics of 5-PhITP Incorporation Opposite an Abasic Site We argue that the increase in the $k_{pol}$ value represents an enhancement in the conformational change step prior to phosphoryl transfer. However, it is also possible that the phosphoryl transfer step is rate-limiting for the incorporation of the nonnatural nucleotide opposite the abasic site. To evaluate this possibility further, time courses in 5-PhITP incorporation were generated under single turnover conditions using either a nondenaturing quench (EDTA) or a denaturing agent (hydrochloric acid). Differences in the amount of product formation can be observed using these quenching agents since EDTA stops the reaction only after a full catalytic cycle while hydrochloric acid kills all enzyme forms that accumulate along the reaction pathway. According to FIG. 5, these enzyme forms include E:DNA, E:DNA:dXTP, and E':DNA:dXTP that can accumulate before the chemical step. Therefore, a reduced burst amplitude in product formation should be observed using the denaturing quench if the phosphoryl transfer step is rate-limiting for incorporation. As shown in FIG. 6, time courses generated for the incorporation of 30 µM 5-PhITP opposite the abasic site are nearly identical with either quenching agent. In both cases, the rate constants for incorporation are essentially identical (37.4 (1 s$^{-1}$ with EDTA versus 38.4 (2.1 s$^{-1}$ with HCl). However, there is an 8.3% difference in burst amplitudes that is dependent upon the nature of the quenching agent. When EDTA is used, the burst amplitude is 240±6 nM while that when HCl is used is 220±3 nM. The potential significance of this slight difference on identification of the rate-limiting step in nucleotide incorporation is discussed later.

Kinetic Parameters for Insertion Opposite Templating Nucleobases

Values for $k_{pol}$, $K_D$, and $k_{pol}/K_D$ were also measured for the incorporation of 5-PhITP, 5-FITP, and 5-AITP opposite any natural templating nucleobase. For each nonnatural nucleotide tested, linear rates in product formation are observed at all concentrations tested regardless of templating base composition, that is, insertion opposite A, C, G, or T. Representative data for the insertion of 5-PhIMP opposite T provided in FIG. 7 reveals that defined "bursts" in primer elongation are not observed for 5-PhIMP insertion opposite T or any other natural templating nucleobase (data not shown). The lack of a burst phase precludes definition of an accurate $k_{obs}$ value for insertion. Regardless, the lack of a defined burst again suggests that phosphoryl transfer or a kinetic step prior to phosphoryl transfer is ratelimiting for their insertion. Values for $k_{pol}$, $K_D$, and $k_{pol}/K_D$ were obtained as described above and are summarized in Table 2.

TABLE 2

Summary of Kinetic Rate and Equilibrium Constants for the Insertion of 5-Phenyl-indolyl-2'-deoxyriboside Triphosphate, 5-Fluoro-indolyl-2'-deoxyriboside Triphosphate, and 5-Amino-indolyl-2'-deoxyriboside Triphosphate Opposite Templating Bases a

| dXTP | Template | $K_{pol}$ (s$^{-1}$) | $K_D$ (µM) | $K_{pol}/K_D$ (M$^{-1}$s$^{-1}$) |
|---|---|---|---|---|
| 5-PhITP | A | 0.12 ± 0.01 | 30 ± 10 | 4.0 × 10$^3$ |
| 5-PhITP | C | 0.19 ± 0.02 | 28 ± 7 | 6.8 × 10$^3$ |
| 5-PhITP | G | 0.26 ± 0.02 | 12 ± 4 | 21.7 × 10$^3$ |
| 5-PhITP | T | 0.16 ± 0.01 | 25 ± 7 | 6.4 × 10$^3$ |
| 5-FITP | A | 0.11 ± 0.06 | 170-28 | 0.6 × 10$^3$ |
| 5-FITP | C | b | b | b |
| 5-FITP | G | b | b | b |
| 5-FITP | T | 0.040 ± 0.003 | 141 ± 32 | 0.29 × 10$^3$ |
| 5-AITP | A | 0.21 ± 0.01 | 263 ± 102 | 0.46 × 10$^3$ |
| 5-AITP | C | b | b | b |
| 5-AITP | G | b | b | b |
| 5-AITP | T | 0.071 ± 0.003 | 132 ± 21 | 0.53 × 10$^3$ | aThe kinetic parameters $k_{pol}$, $K_D$, and $k_{pol}/K_D$ for each nonnatural nucleotide were obtained under pseudo-first-order reaction conditions using 50 nM gp43exo–, 1M 13/20SP-mer, and 10 mM Mg$^{2+}$ at varying concentrations of nonnatural nucleotide triphosphate (0.01-1 mM).
b Not determined since incorporation was not observed at 1 mM nucleotide, the highest concentration tested.

Discussion

Several models have been proposed to account for the preferential insertion of purines opposite an abasic site. Among these include the involvement of hydrophobic effects and entropic compensation as well as steric constraints and shape complementarity. However, an alternative model is the involvement of base-stacking contributions of the incoming nucleobase. We have demonstrated that the incorporation of 5-NITP, a novel nucleobase possessing enhanced base-stacking abilities, is 1000-fold more efficient compared to that for natural nucleobases such as dAMP and dGMP. Furthermore, replacement of the nitro moiety with —H reduces the rate of insertion by 3 orders of magnitude and suggests that the π-electron density of the nitro group plays a major role toward enhancing incorporation opposite an abasic site. In this report, we have further evaluated the contributions of π-electron stabilization through a structure-activity relationship study using various 5-substituted indole triphosphates.

π-Electron Contributions During Catalysis

Our analysis begins by revisiting the established kinetic mechanism of gp43 exo$^-$ (FIG. 5). In this multistep reaction pathway, there are two microscopic steps that are the most significant contributors toward catalysis and fidelity. These include the binding of dNTP to the polymerase/nucleic acid complex and the subsequent conformational change preceding phosphoryl transfer. Proper dNTP binding has historically been attributed to the formation of Watson-Crick base pairs between the incoming dNTP and template nucleobase (FIG. 5, step 2). The formation of correctly paired partners is energetically favorable and typically exemplified by $K_{D\ dNTP}$ values in the low micromolar range. Upon binding the correct dNTP, the polymerase/DNA complex then undergoes a conformational change (FIG. 5, step 3) to further align the incoming dNTP into the correct geometrical arrangement for subsequent phosphoryl transfer (FIG. 5, step 4). During correct DNA synthesis, the rate constant for this conformational change has been experimentally measured at ~100 s$^{-1}$ and is at least 10-fold slower than the rate constant for phosphoryl transfer. Thus, the conformational change step is rate-limiting for the first round of enzyme turnover during normal DNA replication.

During translesion synthesis, however, both ground-state binding of dNTP and the subsequent conformational change are highly disfavored. Although the $K_D$ for natural dNTPs is elevated severalfold, the predominant parameter that kinetically hinders misinsertion is the large reduction in the $k_{pol}$ values. For example, $k_{pol}$ values of ~0.02-0.1 s$^{-1}$ have been reported for the misincorporation of natural dNTPs opposite the abasic site and represent a 103-104-fold reduction compared to those values measured for the formation of natural Watson-Crick base pairs. The reduction in rate constant could reflect the lack of hydrogen-bonding interactions or shape complementarity associated with the lack of coding information present at an abasic site. However, the fast $k_{pol}$ value of ~50 s$^{-1}$ measured here for the incorporation of 5-PhITP and that of ~120 s$^{-1}$ reported for the incorporation of 5-NITP opposite an abasic site suggest that the rate constant for polymerization can be accelerated if the incoming nucleobase contains an extended π-electron surface area. We argue that the increase in the $k_{pol}$ value represents an enhancement in the conformational change step prior to phosphoryl transfer. However, there is still debate as to whether the phosphoryl transfer step is at least partially rate-limiting for the incorporation of the nonnatural nucleotides opposite the abasic site. This issue was evaluated by measuring the time courses in 5-PhITP incorporation using EDTA (a nondenaturing quench) versus HCl (a denaturing agent). As outlined before, a lower burst amplitude should be obtained using HCl if phosphoryl transfer is rate-limiting since any enzyme forms that accumulate before the chemistry step will be effectively quenched by this denaturant while EDTA will quench the reaction only after the first turnover of the polymerase. The time courses presented in FIG. 6 are nearly identical. In both cases, the rate constants in incorporation are identical at ~38 s$^{-1}$. In contrast, the maximal amount of product formed using EDTA is slightly higher (~8%) than that using HCl as the quenching agent. We argue that this difference is minimal and suggests that phosphoryl transfer is not rate limiting for the incorporation of 5-PhITP opposite an abasic site. An argument can, however, be made that this difference may be significant. If correct, then the difference of 8% can be used to calculate the internal equilibrium constant of ~9 for the chemical step. The importance of this value is that it still suggests that phosphoryl transfer may be, at most, partially rate-limiting for the incorporation of 5-PhITP opposite the abasic site. We note that further experiments such as pulse-chase will be required to completely validate that phosphoryl transfer does not completely limit nucleotide incorporation.

These data provide evidence that the conformational change step may be completely rate-limiting for 5-PhITP incorporation opposite an abasic site. We argue that this conformational change step reflects the enzymatic motions required to reposition the incoming nucleobase from an extrahelical position into an interhelical position. This mechanism is intuitive at the molecular level if one considers that an incoming nucleobase containing extensive π-electrons would be thermodynamically favored to exist in the interior of duplex DNA due to offset base-stacking contributions. Indeed, computer models for the structure of the 5-phenylindole deoxyriboside provided in FIG. 8A show that the molecule has an extended π-electron cloud that is not localized to any significant extent. It is noteworthy that the most energetically favorable conformation is that in which the phenyl substituent is tilted 26.8° out-of-plane with respect to the indole moiety. Molecular modeling of the nonnatural nucleoside placed opposite the abasic site reveals that this subtle distortion has a minimal effect on the overall shape of the pair in comparison to a natural A:T base pair (FIG. 8B). Thus, the overall shape and stacking contributions of 5-phenyl-indole opposite an abasic site are predicted to be in an optimal arrangement for stable incorporation. Although the shape and size of 5-phenyl-indole opposite an abasic site appear important for the rate enhancement for incorporation, we argue that it is not the predominant driving force. Specifically, both 5-PhITP and 5-NITP are rapidly incorporated opposite an abasic site despite having significant differences in shape and size (compare 223.2 Å$^2$ for 5-PhITP versus 171.4 Å$^2$ for 5-NITP). If shape complementarity were the sole driving force, then 5-PhITP should be incorporated more efficiently than 5-NITP since it more adequately fills the void of an abasic site. We argue that π-electron surface area, the most notable common feature between the two analogues, plays the most significant role for their facile incorporation opposite an abasic site.

Further evidence of the importance of π-electron surface area comes from evaluation of the insertion of other 5-substituted indoles such as 5-FITP and 5-AITP opposite an abasic site. Although fluorine possesses electronwithdrawing potential similar to that of a nitro group, it does not possess significant π-electron density. In fact, this deficiency can explain the poor kinetics for 5-FIMP insertion opposite the abasic site. A similar line of reasoning can be applied to the amino derivative, 5-AITP. In this case, the amino group is similar in size to a nitro group and also possesses a hydrogen-bond donor group. However, 5-AITP lacks an extended π-electron surface area and is inserted poorly opposite an abasic site. As summarized in Table 1, the catalytic efficiency for 5-FITP and 5-AITP insertion opposite the abasic site is low. Both nonnatural nucleotides display low $k_{pol}$ values of ~0.3 s$^{-1}$ that are remarkably similar to those values reported for the incorporation of dATP and IndTP, respectively. These results collectively suggest that π-electron contributions rather than electronegativity, size constraints, or hydrogen-bonding interactions gives rise to enhanced selectivity for insertion opposite the nontemplating lesion.

π-Electron Interactions are Required for Optimal Ground-State Binding

We envision that the conformational change step outlined in FIG. 5 reflects the ability of the polymerase to "stack" the nucleobases into the interior of the DNA helix. However, the question still remains as to whether (and how) the presence of π-electrons affects ground-state binding of the incoming nucleotide. It was previously demonstrated that the low $K_D$ value of ~20 μM for 5-NITP was independent of templating nucleobase. This result was interpreted to reflect the existence of a "nonselective" dNTP-binding site in gp43 composed of highly conserved aromatic amino acids that could stabilize the binding of the incoming nucleobase through π-π stacking interactions. The kinetic data presented in this manuscript provide additional support for this mechanism. Specifically, the $K_D$ value for 5-PhITP incorporation opposite an abasic site is 14 μM and is essentially identical to that measured for 5-NITP. The identity in binding affinities coincides strongly with the high degree of electron conjugation associated with each molecule. As illustrated in FIG. 9, the active site of the DNA polymerase from bacteriophage RB693 is lined with several aromatic amino acids that are within 10 Å of the primer-template junction. The extended π-electron density of 5-phenylindole could interact favorably with the aromatic amino acids lining the active site of the DNA polymerase. We propose that these previously unrecognized interactions may play an important role in catalysis during translesion DNA synthesis. Indeed, mutagenesis of Y416 to serine dramatically reduces the catalytic efficiency for the incorporation of 5-NITP and 5-PhITP opposite the abasic site lesion while it has little effect on the correct incorporation of dATP opposite T. The reduced efficiency during translesion DNA synthesis is consistent with the loss of base-stacking interactions in the enzyme's active site.

The measured $K_D$ values for 5-FITP and 5-AITP insertion opposite the abasic site provide additional insight into the dynamics of nucleotide binding. Replacement of π-electrons with either an electron-withdrawing group (5-fluoro derivative) or a group capable of providing hydrogen-bonding interactions (5-amino derivative) reduces binding affinity by at least 10-fold (Table 3). This reduction corresponds to a change in relative free energy of ~1.4 kcal/mol that potentially represents the energy associated with π-π stacking. Removal of π-electron density at the 5-position of indole could easily reduce the strength between the interactions of the incoming nucleobase with these active site residues to adversely affect binding affinity.

Alternative Models for Translesion DNA Synthesis

Alternative mechanisms invoking the involvement of desolvation, dipole moment, or both could also account for the preferential insertion of 5-NIMP and 5-PhIMP opposite the abasic site. If desolvation were the most critical parameter, then the efficiency of insertion should correlate well with the hydrophobicity (log P) of the nucleobase. This model predicts that 5-PhIMP should be inserted opposite an abasic site with a higher overall efficiency compared to 5-NIMP due to the large value of 3.3 of the former nucleobase compared to the lower log P of ~1.7 of the latter. As summarized in Table 3, the catalytic efficiency for 5-PhIMP insertion is 2-fold lower than 5-NIMP despite the fact that the log P value of 5-phenyl-indole is significantly higher. Further evaluation of other modified indole triphosphates yields identical interpretations. For example, indole deoxyriboside and the 5-fluoro derivative have nearly identical log P values compared to 5-NIMP yet are inserted 1000-fold less efficiently. While desolvation undoubtedly plays a significant role during DNA replication by stabilizing duplex DNA (reviewed in ref 1), it appears to play a minimal role in directly influencing nucleotide insertion during translesion DNA synthesis. Other relevant biophysical parameters such as dipole moment and surface area (Table 3) appear to play minimal roles on an individual basis since a reasonable correlation between the measured catalytic efficiency with either of these parameters is not observed.

TABLE 3

Comparison of Selective Biophysical Parameters of Various 5-Substituted Indole Derivatives

| nucleobase | Catalytic efficiency[a] | log P[b] | dipole moment[c] | surface area (Å$^2$)[d] | volume (Å$^3$)[e] | π-electrons[f] |
|---|---|---|---|---|---|---|
| adenine | $1.5 \times 10^3$ | −1.45 | 2.38 | 143.0 | 121.7 | no |
| indole | $1.9 \times 10^3$ | 1.64 | 2.02 | 146.2 | 131.1 | no |
| 5-nitro-indole | $7.0 \times 10^6$ | 1.67 | 7.81 | 171.4 | 152.4 | yes |
| 5-phenyl-indole | $3.8 \times 10^6$ | 3.31 | 2.24 | 223.2 | 213.4 | yes |
| 5-fluoro-indole | $2.0 \times 10^3$ | 1.79 | 4.22 | 152.0 | 135.7 | no |
| 5-amino-indole | $0.5 \times 10^3$ | 0.83 | 1.00 | 159.7 | 141.3 | no |

[a]Catalytic efficiency is defined as $k_{pol}/K_D$ (M$^{-1}$ s$^{-1}$) and represents the apparent second-order rate constant of the enzyme catalyzed reaction. These values are taken from Table 1 and references cited within.
[b]The log P values, the oil-to-water partition coefficients, were calculated using Spartan '02 software and are used as an indicator of relative hydrophobicity.
[c]Dipole moments (D) were calculated using Spartan '02 software and are used as an indicator of relative electronegativity.
[d]Surface areas were calculated using Spartan '02 software.
[e]Volumes were calculated using Spartan '02 software and are used as an indicator of relative size of the nucleobase.
[f]The term π-electrons refers to the presence of a conjugated substituent group at the 5 position of indole.

The Role of Shape Complementarity During DNA Polymerization

5-Substituted indoles such as 5-FITP and 5-AITP were expected to be efficiently inserted opposite the pyrimidines, C and T, since they were predicted to form base pairs that resemble Watson-Crick base pairs due to the favorable contributions of steric fit and potential hydrogenbonding interactions. The data summarized in Table 3 shows a poor correlation between the efficiency of nucleotide insertion and the shape of the formed base pair. This unexpected result is best highlighted by examination of the unfavorable kinetic parameters associated with the insertion of 5-AITP opposite pyrimidines. Despite having a hydrogen bond donor that could potentially interact with the C4 keto group of thymine, the insertion of 5-AIMP opposite T was very ineffective as manifested in a low $k_{pol}$ (~0.07 s$^{-1}$) coupled with a high $K_D$ value (~130 µM). Likewise, insertion of 5-AIMP opposite C was not detected. This observation is not unique to 5-AIMP insertion since identical trends are also observed for the insertion of 5-FIMP (Table 2).

The most intriguing results are again observed for the insertion of 5-PhIMP opposite any of the templating bases. Although the catalytic efficiency for 5-PhIMP insertion does vary depending upon the composition of templating nucleobase, the measured $k_{pol}/K_D$ values are in most cases 10-fold greater than those measured for 5-FITP and 5-AITP. Surprisingly, the most influential parameter is binding affinity (low $K_D$ values) rather than an enhancement in the rate of the conformational change (low $k_{pol}$ values). The $K_D$ for 5-PhITP is ~25 µM and remarkably similar to the $K_D$ values measured for the incorporation of 5-NITP. We again propose that the higher binding affinities for nucleotides containing enhanced π-electron contributions is evidence for a "nonspecific" binding site for an incoming dNTP that takes advantage of π-π stacking interactions between the aromatic rings of the incoming dNTP and amino acids. The low $k_{pol}$ values could reflect the impact of shear bulk present on the phenyl ring that most likely precludes stable pairing opposite a template base. This could reflect the contribution of steric fitting/shape complementarity or negative selection.

Conclusion

This report highlights the significant role of π-electron surface area during DNA polymerization, especially during incorporation opposite an abasic site. Perhaps the most intriguing aspect is how the bacteriophage T4 DNA polymerase utilizes the formation of noncovalent bonds between π-π stacking systems to facilitate nucleotide binding and the conformational change step preceding phosphoryl transfer. Preliminary data using the Klenow fragment of *E. coli* DNA polymerase I reveal that this polymerase inserts 5-PhIMP at least 10-fold more efficiently opposite an abasic site than 5-NIMP. This result appears to contrast data obtained using the bacteriophage T4 enzyme and leads to the provocative suggestion that DNA polymerases utilize different catalytic strategies during DNA polymerization.

Example 2

Potential Chemotherapeutic Strategy for the Selective Inhibition of Promutagenic DNA Synthesis by Nonnatural Nucleotides Current chain terminators containing natural nucleobases theoretically lack the intrinsic selectivity to inhibit one DNA polymerase versus another. Since these agents resemble their natural counterparts, they may be degraded by cellular enzymes that metabolize natural nucleotides. For example, enzymatic deamination of purine analogues such as dideoxyadenosine limits its use and may play a significant role in the development of drug resistance to natural nucleoside analogues.

To combat these complications, we attempted to exploit several of the unique features of the previously described nonnatural nucleotides that are displayed in FIG. 10. Specifically, we demonstrate that two of these nonnatural nucleotides are selectively inserted opposite damaged DNA that can be induced by chemotherapeutic agents. More importantly, these molecules act as potent and selective chain terminators of replication beyond an abasic site. This activity will inhibit the propagation of genomic errors caused by extending beyond a natural mispair. In general, the ability to selectively inhibit promutagenic DNA synthesis would be beneficial in preventing a leading culprit in disease development and drug resistance.

Materials and Methods

Materials

[γ-$^{32}$P]ATP was purchased from M. P. Bio-Medicals. Ultrapure, unlabeled dNTPs were obtained from Pharmacia. Magnesium acetate and Trizma base were from Sigma. Urea, acrylamide, and bisacrylamide were from Aldrich. Oligonucleotides, including those containing a tetrahydrofuran moiety mimicking an abasic site, were synthesized by Operon Technologies (Alameda, Calif.). Singlestranded and duplex DNA were purified and quantified as described. All other materials were obtained from commercial sources and were of the highest available quality. The wild-type gp43 and the exonuclease-deficient mutant of gp43 (Asp-219 to Ala mutation) were purified and quantified as previously described. The nonnatural nucleotides used in this study were synthesized and purified as described.

Enzyme Assays

The assay buffer used in all kinetic studies consisted of 25 mM Tris-OAc (pH 7.5), 150 mM KOAc, and 10 mM 2-mercaptoethanol. All assays were performed at 25° C. Polymerization reactions were monitored by analysis of the products on 20% sequencing gels. Gel images were obtained with a Packard PhosphorImager using the OptiQuant software supplied by the manufacturer. Product formation was quantified by measuring the ratio of $^{32}$P-labeled extended and nonextended primer. The ratios of product formation are corrected for substrate in the absence of polymerase (zero point). Corrected ratios are then multiplied by the concentration of primer/template used in each assay to yield total product. All concentrations are listed as final solution concentrations.

Competition Experiments

Ten nanomolar gp43 exo$^-$ was preincubated with 1000 nM 13/20-mer. To accurately visualize elongation, the 13-mer primer strand was labeled with [γ-$^{32}$P]ATP using T4 polynucleotide kinase (New England Biolabs) and annealed with a stoichiometric amount of unlabeled 20-mer. The polymerization reaction was initiated by the addition of 10 μM dNTPs (dATP, dGTP, dTTP) in the absence or presence of 500 μM 5-NITP. Five microliter aliquots of the reaction were quenched into tubes containing 5 μL of 200 mM EDTA at times ranging from 5 to 180 s. The quenched samples were processed as described above and product formation was analyzed using established protocols.

Competition assays during translesion DNA synthesis were performed with several slight modifications to the aforementioned protocol. First, single turnover conditions were employed in which 1000 nM gp43 exo$^-$ was preincubated with 250 nM 13/20SP-mer. As above, the 13-mer primer strand was labeled with [γ-$^{32}$P]ATP using T4 polynucleotide kinase and annealed with a stoichiometric quantity of unlabeled 20SP-mer. Second, the polymerization reaction was initiated by the addition of 500 μM dNTPs (dATP, dGTP, dTTP) in the absence and presence of 20 μM 5-NITP. Aliquots of the reaction were quenched into 200 mM EDTA at times ranging from 5 to 300 s and processed as described above.

Pre-Steady-State Exonuclease Assays

A rapid quench instrument was used to monitor the time course in hydrolysis of DNA containing a variety of mispaired primer-templates. In these experiments, a preincubated solution of 2 μM gp43 exo+/10 mM Mg$^{2+}$ was mixed with 500 nM 5'-labeled DNA (final concentrations). The reaction was then terminated at various times by the addition of 350 mM EDTA, and the reaction products were analyzed as described above. In all cases, the data were plotted as initial substrate (typically 14-mer) remaining as a function of time. Data for each time course were fit to the following equation defining a first-order decay in initial substrate concentration.

$$y = Ae^{-kt} + C$$

where A is the burst amplitude, k is the observed rate constant for product formation, and C is the end point of the reaction.

Idle-Turnover Measurements

DNA (13/20SP-mer or 13/20T-mer; 250 nM) was first preincubated with variable concentrations of 5-NITP (20-200 μM) or 5-PhITP (10-200 μM) in the presence of 30 μM dATP. Due to the nature of the DNA substrate (FIG. 1B), the insertion of dAMP opposite T at position 13 in the template maintains a usable primer template for the insertion of the nonnatural nucleotide opposite the abasic lesion (position 14). In all cases, the reaction was initiated through the addition of 1000 nM DNA gp43 exo$^+$. Five microliter aliquots of the reaction were quenched into tubes containing 5 μL of 200 mM EDTA at times ranging from 5 to 600 s. The quenched samples were processed as described above and product formation was analyzed using established protocols.

Simulations modeling the observed kinetic time courses for nucleotide insertion and excision were performed by mathematical analyses using KINSIM. A simplified mechanism depicted in FIG. 11 was employed that accounts for the kinetic parameters of interest. These minimally include $K_D$ values for each nucleotide, $k_{pol}$ values for their insertion, and $k_{exo}$, which represents the hydrolytic rate constant. Both the starting reactant concentrations and rate constants were supplied for each step of the mechanism. In all cases, the rate constants were based upon either experimentally determined rate constants or published literature values. The simulated curves were then compared to those experimentally derived to judge how accurately each set of rate constants fit the experimental data. Adjustments to the rate constants were then made until the simulated time courses were nearly identical to the experimental time courses.

Results and Discussion

5-NITP and 5-PhITP are Chain Terminators of DNA Synthesis

It was previously demonstrated that gp43 exo$^-$ can extend beyond an abasic site only when dAMP or dGMP are placed opposite the lesion. The ability to extend beyond these mispairs was proposed to reflect the positioning of these nucleobases in an interhelical position when paired opposite an abasic site. Since 5-NITP and 5-PhITP (preceding manuscript) are more efficiently inserted opposite an abasic site, it was predicted that gp43 exo$^-$ would easily extend beyond these nonnatural analogues since they should exist in an interhelical conformation when paired opposite this lesion. This hypothesis was directly tested by measuring the ability of gp43 exo$^-$ to extend beyond either mispair using the experimental protocol outlined in FIG. 12A. Briefly, the preincubated gp43 exo$^-$:13/20SP-mer complex was incubated with 50 μM dXTP for 30 s. This time frame allows all of the primer to be elongated by only one base, that is, conversion of 13-mer to 14-mer (FIG. 12B, lane 2). After this time frame, 1000 μM dGTP was added to allow extension beyond the enzymatically formed 5-NIMP:abasic site mispair. Surprisingly, the polymerase cannot elongate beyond the 14-mer product even when supplied with high concentrations of the next correct dNTP. Increasing the reaction time, the concentration of dGTP, or both has no effect on extension (data not shown). The phenomenon is not limited to 5-NITP since identical results are obtained using 5-PhITP as the nucleotide substrate (data not shown).

FIG. 12C displays the results from the positive control experiment monitoring incorporation and elongation beyond the DNA lesion when only natural dNTPs are used. As expected, gp43 exo$^-$ incorporates dATP opposite the abasic site. Extension beyond the formed dAMP:abasic site occurs when dGTP is added to the reaction mixture since a variety of polymerization products ranging from 15- to 17-mers accumulate. Thus, replication beyond an abasic site does occur, albeit with low efficiency.

The inability to extend beyond nonnatural nucleosides indicates that both 5-NITP and 5-PhITP are chain terminators of DNA synthesis. At face value, these results appear contradictory to our original hypothesis stating that the kinetics of elongation should be dependent upon the interhelical conformation of the nucleobase. However, alternative mechanisms distinct from perturbations in interversus extrahelical conformation could also account for the lack of extension. One possibility could reflect improper size or geometrical constraints imposed by the nonnatural mispair. For example, distortion of the newly formed mispair could cause the polymerase to stall or prevent translocation to the next templating position. Another potential mechanism invokes the contributions of various heterocyclic nitrogens during the polymerization cycle. In this regard, several groups have demonstrated that purine analogues devoid of either the N7 or N3 nitrogens are effectively inserted into DNA but are refractory to elongation. These results again demonstrate that typical hydrogenbonding functional groups are not necessary for incorporation. However, their presence appears obligatory for efficient elongation. In fact, these functional groups are proposed to be required for minor groove contacts between the nucleic acid and DNA polymerase. It is easy to envision that the removal of these contacts could prevent translocation of the polymerase, disturb the orientation of the primer/template, or both to inhibit elongation.

Potency and Selectivity for Inhibiting Replication Beyond an Abasic Site

The previous data indicate that replication beyond an abasic site could be selectively inhibited by 5-NITP and 5-PhITP. The next goal was to determine whether these nonnatural nucleotides could effectively compete with natural dNTPs for insertion opposite an abasic site under in vivo relevant conditions. This was accomplished using an adaptation of the protocol illustrated in FIG. 12A using unmodified DNA or DNA containing an abasic site (FIG. 10B). This experimental paradigm has two distinct advantages. The first is that it directly measures the ability of 5-NITP (or 5-PhITP) to compete with natural dNTPs for insertion opposite damaged or unmodified DNA (potency and selectivity). Second, it measures the ability of these nonnatural analogues to prevent elongation beyond potential mispairs and evaluates the potential efficacy of these compounds.

As a positive control, the ability of gp43 exo⁻ to insert and elongate beyond the abasic site was measured in the absence of either 5-NITP or 5-PhITP. Since replication beyond this form of DNA damage is typically disfavored, high concentrations of natural dNTPs (500 μM each) were used to enhance insertion and extension beyond this form of DNA damage. In the absence of any nonnatural nucleotide, gp43 exo⁻ inserts and extends beyond the abasic site fairly efficiently (FIG. 13A).

FIG. 13B, however, shows the results of a competition experiment performed in the presence of 20 μM 5-NITP and 500 μM dNTPs. Denaturing gel electrophoresis shows that there is a rapid production of 14-mer that reflects the exclusive incorporation of 5-NITP opposite the abasic site. A more important observation, however, is that the level of 14-mer product remains invariant during the time course of the reaction. Identical results are obtained when the experiment is performed substituting 5-PhITP for 5-NITP (data not shown). The inability of gp43 exo⁻ to extend beyond the generated mispairs provides a clear indication of the chain termination abilities of 5-NITP and 5-PhITP. Furthermore, this inhibition is not observed when the reaction is performed using IndTP, 5-FITP, or 5-AITP at a fixed concentration of 20 μM (data not shown). Increasing the concentration of these analogues to 350 μM has no effect on the kinetics of elongation (data not shown). The inability of these analogues to inhibit replication beyond an abasic site likely arises from the fact that all three analogues have high $K_D$ and low $k_{pol}$ values for insertion opposite the abasic site.

The potency of 5-NITP toward inhibiting replication beyond an abasic site was further quantified by measuring the dose dependence of 5-NITP toward inhibiting primer elongation. Experiments were performed as described above with the exception that the concentration of 5-NITP was varied at 0, 5, 10, and 20 μM. As expected, extension beyond the abasic site occurs in the absence of nonnatural nucleotide. However, the amount of extension decreases as the concentration of 5-NITP is increased. The IC50 value for 5-NITP is 10 μM since this concentration inhibits 50% of primer extension. Similar analyses for 5-PhITP yield an $IC_{50}$ value of 10 μM (data not shown). Collectively, these data indicate that 5-NITP and 5-PhITP can effectively compete with natural dNTPs for the binding to the polymerase and can inhibit translesion DNA synthesis.

Chain Termination Capabilities Using Unmodified DNA

The ability of these nonnatural nucleotides to function as generic chain terminators was also evaluated using an unmodified DNA substrate. In these experiments, pseudofirst-order conditions were used since normal DNA synthesis is more efficient than translesion DNA synthesis. Specifically, a limiting concentration of gp43 exo⁻ (10 nM) was preincubated with 1000 nM 13/20-mer prior to the addition of 10 μM dNTPs in the absence (FIG. 14A) or in the presence of 500 μM 5-NITP (FIG. 14B). In the absence of 5-NITP, a ladder of products ranging from 14-mers to 20-mers is observed, a result that demonstrates the ability of the polymerase to easily elongate unmodified DNA. The wide distribution of elongation products reflects the low processivity of the polymerase under pseudo-first-order conditions. Visual inspection of the data provided in FIG. 14B reveals that the addition of 500 μM 5-NITP has little effect on the ability of gp43 exo⁻ to perform normal DNA synthesis. Further quantification of the reaction products indicates that the addition of 500 μM 5-NITP reduces the overall rate in primer elongation by less than 10% (FIG. 14C). The slight degree of inhibition on the rate and extent of primer elongation indicates that 5-NITP has low potency for terminating synthesis on undamaged DNA. Nearly identical results are obtained when 5-PhITP is substituted for 5-NITP (data not shown). The ability of other nonnatural nucleotides to inhibit normal DNA synthesis was also evaluated. High concentrations (500 μM) of other nonnatural nucleosides, such as IndTP, 5-FITP, or 5-AITP do not inhibit normal DNA synthesis (data not shown). As before, the inability to inhibit normal DNA synthesis likely reflects their poor kinetic parameters for insertion opposite natural templating bases, that is, high $K_D$ and low $k_{pol}$ values.

Stability of 5-NITP Incorporation Opposite Natural or Damaged DNA

The associated exonuclease activity of the DNA polymerase can effectively remove most chain terminators from DNA after being incorporated. In the case of our nonnatural nucleotides, this activity would render the analogue therapeutically useless. To address this concern, we evaluated the ability of gp43 exo⁺ to excise 5-NIMP from DNA when it is placed opposite the nontemplating lesion or opposite T. The advantage of the bacteriophage T4 enzyme is that it possesses a vigorous exonuclease activity that plays a significant role in the maintenance of fidelity. Excision reactions were performed employing single turnover conditions in a rapid quench instrument. The first set of experiments compare the excision of 5-NIMP and dAMP when paired opposite an abasic site (FIG. 15). Time courses in excision are best defined as a single-exponential curve. An observed rate constant of excision ($k_{exo}$) of 9.9±0.8 s⁻¹ is measured for excising 5-NIMP, while the $k_{exo}$ value for excising dAMP is 28.5±1.1 s⁻¹.

TABLE 4

Summary of Exonuclease Rate Constants Measured for the Excision of dAMP or 5-NIMP Paired Opposite an Abasic Site or Thymine

| primer nucleoside | template nucleoside | $k_{exo}$ (s$^{-1}$) |
|---|---|---|
| dAMP | thymine | 0.8 ± 0.1 |
| dAMP | abasic site | 28.5 ± 1.1 |
| 5-NITP | thymine | 13.0 ± 1.4 |
| 5-NITP | abasic site | 9.9 ± 0.8 |

[a]The kinetic rate constant, $k_{exo}$, was measured under single turnover reaction conditions using 1 M gp43 exo+, 250 nM DNA (14A/20T-mer, 14A/20SP-mer, 14NI/20T-mer, or 14NI/20SP-mer), and 10 mM Mg$^{2+}$.

Surprisingly, the kinetics of 5-NIMP excision placed opposite T are nearly identical to that measured for excision opposite the abasic site as reflected in the $k_{exo}$ value of 13.0±1.4 s$^{-1}$, which is nearly identical to that measured for excision opposite the abasic site. Control experiments measuring the excision of dAMP when paired opposite T reveal that excision of dAMP is significantly slower since the $k_{exo}$ value is 0.8±0.1 s$^{-1}$. This value is consistent with the published value of 2 s$^{-1}$.

Comparing the rate constants of excision summarized in Table 4 provides interesting insights into the dynamics of exonuclease proofreading. First, the rate constant for dAMP excision opposite the abasic site is ~40-fold faster than that measured when the natural nucleotide is paired opposite T. The faster rate constant undoubtedly reflects the nature of the mispair. Not surprisingly, the rate constant for excising 5-NIMP from an abasic site is 3-fold slower than that for dAMP excision from the same lesion. We argue that this difference reflects the increased base-stacking capabilities of 5-NIMP compared to dAMP such that the increased stability of the 5-NIMP:abasic site makes it more difficult to partition the primer into the exonuclease active site for degradation. This argument is consistent with biochemical and structural data indicating that at least three base pairs have to be melted for the primer to partition to the exonuclease active site of the bacteriophage polymerase.

This model may also explain the similarity in rate constants for excising 5-NIMP from T versus an abasic site. This result was surprising since it was predicted that the 5-NIMP:T mispair would be hydrolyzed much faster than the 5-NIMP: SP mispair. This prediction is based upon the generally accepted kinetic model for fidelity in which the rates of dNMP excision ($k_{exo}$) are inversely correlated with the rates of dNTP incorporation ($k_{pol}$). The basis for this model is intuitively obvious: the more difficult it is to form a mispair, the easier it should be to degrade it and vice versa. We have demonstrated that this correlation exists during translesion DNA synthesis with natural nucleotides since it is kinetically unfavorable to incorporate dATP opposite an abasic site ($k_{pol}$≈0.15 s$^{-1}$) while it is kinetically favorable to excise dAMP ($k_{exo}$≈28 s$^{-1}$). Although the majority of data with natural mispairs support this argument, the dynamics of exonuclease proofreading may be different when nonnatural nucleotides are placed in the primer. For example, we previously demonstrated that the incorporation of 5-NITP opposite an abasic site ($k_{pol}$±126 s$^{-1}$) is kinetically favored by 140-fold compared to the insertion of 5-NITP opposite T ($k_{pol}$±0.9 s$^{-1}$) (28). The kinetic difference arguably reflects the enhanced stability of the 5-nitro-indole opposite the template rather than when paired opposite T in the template. Since the 5-NIMP:T mispair appears less favorable, it stands to reason that it should be rapidly degraded. However, the $k_{exo}$ value of ~10 s$^{-1}$ for excision from opposite T is essentially identical to that measured for excision from the "favored" mispair of 5-NIMP:SP. It is tempting to speculate that the identity in kinetics for excision of 5-NIMP from different mispairs reflects the universal base-stacking properties of the nonnatural nucleobase.

Idle Turnover Measurements

Idle turnover is a process in which the DNA polymerase incorporates a dNTP and then excises the inserted dNMP in the absence of the next required nucleotide triphosphate (FIG. 11). This activity provides a more accurate representation of in vivo conditions in which the polymerase should be bound and stalled at the sight of DNA damage. Idle turnover was quantified using a modified gel electrophoresis protocol that monitors the amount of extension (13-mer to 14-mer) and subsequent excision (14-mer to 13-mer) of the DNA as a function of time. All experiments were performed using single turnover reaction conditions to ensure that all DNA was bound with polymerase during the course of the reaction. Under these conditions, the rates in product formation reflect the kinetics of insertion and excision rather than enzyme dissociation from the mispair. In each experiment, the concentration of nonnatural nucleotide was varied from 20 to 200 μM. In addition, a low concentration of 30 μM dATP was used to allow for correct dNMP insertion at position 13-mer, which prevents complete degradation of DNA substrate.

FIG. 16A shows representative denaturing gel electrophoresis data for the idle turnover of 5-NITP opposite the abasic site at 20 and 200 μM 5-NITP, respectively. FIG. 16B provides the time courses monitoring the production of 14-mer under these conditions and reveals that the accumulation of 14-mer is both concentration- and time-dependent. At either concentration, there is rapid primer elongation to form 14-mer since the catalytic efficiency for 5-NITP incorporation opposite the lesion is high ($k_{pol}/K_D$=7.0×10$^6$ M$^{-1}$ s$^{-1}$). The steady-state accumulation of 14-mer product reflects the latency in degradation that defines the process of idle turnover. It is clear, however, that there is an attenuation in the time course for 14-mer degradation as the concentration of 5-NITP is increased from 20 to 200 μM. This dose dependency can easily be explained by the law of mass action since the concentration of nucleotide substrate diminishes during this steady-state phase due to repetitive cycling of insertion and excision. Under these conditions, the concentration of 5-NITP decreases until it is below the $K_D$ value. At this point, the polymerase is unable to continue incorporation opposite the lesion, and this leads to complete degradation of the 14-mer.

To validate this model, computer simulations of the data were performed using the mechanism provided in FIG. 11. Since single turnover reaction conditions were employed, kinetic steps reflecting enzyme dissociation and rebinding to product DNA are assumed to be negligible. Thus, the rate and amount of 14-mer produced are dependent upon four interrelated parameters. These include the kinetic dissociation constant ($K_D$) for dXTP opposite the lesion (DNA$_n$) (step 2), the rate constant for DNA extension ($k_{pol}$) (step 3), the rate constant of exonuclease degradation ($k_{exo}$) (step 5), and the kinetic dissociation constant ($K_D$') for dXTP opposite the next templating position (DNA$_{n+1}$) (step 6). Although $k_{pol}$ is a complex function of kinetic rate constants, this value was simplified to combine the kinetic steps encompassing the conformational change prior to phosphoryl transfer, phosphoryl transfer, and the conformational change after phosphoryl transfer. Furthermore, translocation of the enzyme and pyrophosphate release (step 4) are assumed to be rapid.

Initial computer simulations were performed using the published $K_D$ value of 18 μM and the $k_{pol}$ value of 126 s$^{-1}$ for 5-NITP incorporation opposite an abasic site. The experimentally measured value of 10 s$^{-1}$ was used for k$_{exo}$ (vide supra). At a fixed concentration of 5-NITP (20 μM), the time course in the production and subsequent degradation of 14-mer could only be adequately fit if a parameter that represented the kinetic equilibrium dissociation constant (K$_D$') for 5-NITP opposite the next templating position (DNA$_{n+1}$) was included in the simulations. Computer simulations were also performed for the time courses generated at several different fixed concentrations of 5-NITP (20, 50, 100, and 200 μM). In all cases, time courses were best fit using the following parameters: K$_D$ value of 20 μM, a k$_{pol}$ value of 100 s$_{-1}$, a k$_{exo}$ value of 10 s$^{-1}$, and a K$_D$' value of 10 mM.

Identical analyses were performed to measure the idle turnover of 5-PhITP as the nucleotide substrate. The data provided in FIG. 17 compares the time courses generated for the incorporation of 100 μM 5-PhITP versus 100 μM 5-NITP opposite the abasic site. It is clear that the phenylindole derivative is more stably incorporated opposite the abasic site compared to the nitro indole analogue. This result is somewhat surprising since the overall catalytic efficiency for 5-PhITP incorporation opposite the lesion (k$_{pol}$/K$_D$=3.6×10$^6$ M$^{-1}$ s$^{-1}$) is 2-fold lower than that measured for 5-NITP (k$_{pol}$/K$_D$=7.0×10$^6$ M$^{-1}$ s$^{-1}$). Regardless, the enhanced stability of 5-PhIMP opposite the lesion is indicative of a decrease in idle turnover. This reduction could be caused at two mutually exclusive mechanisms that would be reflected in perturbations in two different kinetic steps along the reaction pathway. The first step would be a reduced rate constant in degradation (k$_{exo}$), while the alternative is a reduction in the K$_D$' value for the next templating position. Computer simulation was again used to generate values corresponding to K$_D$, k$_{pol}$, k$_{exo}$, and K$_D$' (Table 5). The parameter most sensitive to variation is the k$_{exo}$ value. In fact, this value is 10-fold slower than that measured for the excision of 5-NIMP from opposite the abasic site. This result indicates that it is more difficult to excise the large phenyl-indole derivative than the smaller 5-nitro analogue. It is tempting to speculate that the reduced rate constant in exonuclease degradation reflects the enhanced base-stacking capabilities of the 5-phenyl-indole derivative.

Potential Toxicity and Therapeutic Indices of the Non-Natural Nucleotides

These results collectively indicate that nonnatural nucleotides 5-NITP and 5-PhITP can effectively inhibit replication beyond an abasic site under in vitro conditions. To place constraints on the potential in vivo utility of these analogues to inhibit promutagenic versus normal DNA replication, we defined the potential toxicity and therapeutic indices of 5-NITP and 5-PhITP. It should be noted that we define potential toxicity as the inhibition of replication beyond an abasic site. While the term "toxic" is used as a descriptor, this activity is considered to be beneficial since it would potential prevent promutagenic DNA synthesis. Briefly, the potential effectiveness of each analogue to inhibit replication beyond an abasic site was evaluated by measuring the catalytic efficiency, k$_{pol}$/K$_D$, for both analogues and then calculating the discrimination for insertion as the ratio of catalytic efficiencies for the nucleotide analogue versus the correct dNTP. Among the four natural nucleotides, dATP has the highest k$_{pol}$/K$_D$ value for incorporation opposite an abasic site and is therefore considered to be the correct dNTP for replication opposite this lesion. In the case of incorporation opposite an abasic site, discrimination (D) is defined as (k$_{pol}$/K$_D$)dATP/(k$_{pol}$/K$_D$)$_{dXTP}$. Using 5-NITP as the nonnatural nucleotide, we can calculate the discrimination factor as 7×10$^6$ M$^{-1}$ s$^{-1}$/4300 M$^{-1}$ s$^{-1}$ yielding a value for D of 6.1×10$^{-4}$ (Table 6). Similar analyses were used to calculate a D value of 11.4×10$^{-5}$ for 5-PhITP (Table 6). Both values are extremely low and provide a clear indication that the nonnatural nucleotides should be exclusively incorporated opposite an abasic site. We note that this conclusion is true only if the concentrations of dATP and dXTP are equal. It is obvious that these discrimination values will approach unity if the concentration of dATP increases in relationship to that of the nonnatural nucleotide, a condition that may occur within an in vivo context due to potential differences in absorption and metabolism.

TABLE 5

Summary of Kinetic Rate and Equilibrium Constants Measured for the Idle Turnover of 5-Nitro-indolyl-2'-deoxyriboside Triphosphate (5-NITP) and 5-Phenyl-indolyl-2'-deoxyriboside Triphosphate (5-PhITP) Opposite an Abasic Site

| dXTP | K$_D$ (μM) | k$_{pol}$(S$^{-1}$) | k$_{exo}$(S$^{-1}$) | K$_D$' (μM) |
|---|---|---|---|---|
| 5-NITP | 20 ± 5 | 100 ± 10 | 10 ± 2 | 10 000 ± 1000 |
| 5-PhITP | 20 ± 5 | 50 ± 10 | 1.0 ± 0.1 | 10 000 ± 1000 |

Regardless, these favorable discrimination values predict that 5-NITP and 5-PhITP have the potential to be chemopreventive agents. As previously noted, however, the associated exonuclease activity of the DNA polymerase could effectively remove them to render these analogues therapeutically useless. As such, the combined contributions of incorporation and excision must be considered when evaluating the potential therapeutic utility of any nucleotide analogue. This can be evaluated by calculating the toxicity index, which is defined as (k$_{pol\ dNTP}$/k$_{exo\ dXTP}$)(dXTP/dNTP)/(4D) where k$_{pol\ dNTP}$ represents the maximal rate of polymerization of the natural dNTP, k$_{exo\ dXTP}$ represents the maximal rate of excision of the nonnatural nucleotide, (dXTP/dNTP) is the ratio of nonnucleotide and natural nucleotide concentrations, and D is the aforementioned calculated discrimination factor. This value defines the relative increase in time that would be required to extend beyond an abasic site based upon the rate constants for incorporation and excision of the nonnatural nucleotide. In the case of 5-NITP, this value is ~6, while that for 5-PhITP is ~33 (Table 6). The difference in values reflects the slower excision of 5-PhIMP compared to 5-NIMP and suggests that 5-PhITP would be more effective toward inhibiting replication opposite an abasic site.

TABLE 6

Summary of Calculated Discrimination Values, Toxicity Index, and Therapeutic Index for 5-Nitro-indolyl-2'-deoxyriboside Triphosphate (5-NITP) and 5-Phenyl-indolyl-2'-deoxyriboside Triphosphate (5-PhITP)

| parameter | 5-NITP | 5-PhITP |
|---|---|---|
| discrimination (abasic DNA)[a] | 6.1 × 10$^{-4}$ | 11.4 × 10$^{-4}$ |
| discrimination (unmodified DNA)[a] | 53 | 460-2500 |
| toxicity index (abasic DNA)[b] | 6 | 33 |
| toxicity index (unmodified DNA)[b] | 0.047 | 0.01-0.05 |
| therapeutic index[c] | 128 | 660-3300 |

[a]Discrimination (D) is defined as (k$_{pol}$/K$_D$)$_{dXTP}$/(k$_{pol}$/K$_D$)$_{dATP}$.
[b]The toxicity index for each analogue was calculated as (k$_{pol\ dNTP}$/k$_{exo\ dXTP}$)(dXTP/dNTP)/(4D) where k$_{pol\ dNTP}$ represents the maximal rate of polymerization of the natural dNTP, k$_{exo\ dXTP}$ represents the maximal rate of excision of the nonnatural nucleotide, (dXTP/dNTP) is the ratio of nonnucleotide and natural nucleotide concentrations, and D is the discrimination factor.
[c]The therapeutic index of each nonnatural nucleotide was calculated using the toxicity index for abasic containing DNA divided by the toxicity index using normal DNA.

We next evaluated the potential of 5-NITP and 5-PhITP to provide what we consider to be a true toxic response by inhibiting normal DNA synthesis, i.e., stable incorporation opposite unmodified DNA. As outlined above, discrimination can be calculated by the ratio of $(k_{pol}/K_D)_{dXTP}/(k_{pol}/K_D)_{dNTP}$ for incorporation opposite templating nucleobase. In the case of unmodified DNA, we find that the D value for 5-NITP is ~53, while that for 5-PhITP is 460-2500.[6] These extremely high values indicate that nonnatural nucleotide, especially 5-PhITP, should be rarely incorporated opposite any of the four natural nucleobases. Furthermore, these values can be used to calculate the toxicity index of 0.047 for 5-NITP and 0.01-0.05 for 5-PhITP (Table 6). The importance of these low values is that neither analogue should give a toxic response by inhibiting normal DNA synthesis since they are not stably incorporated opposite unmodified DNA.

Finally, the therapeutic index of each nonnatural nucleotide was calculated using the toxicity indices for the inhibition of normal DNA synthesis and replication beyond an abasic site. The therapeutic index (TI) of a drug defines how selective it may be toward producing a desired effect rather than an adverse one and is classically defined as the ratio of the toxic dose (TD) in relation to its effective dose (ED). In computing this value, we designate that the toxic dose reflects inhibition of replication on unmodified DNA, while the effective dose reflects inhibition of replication beyond an abasic site, or the toxicity index for abasic containing DNA/the toxicity index using normal DNA. Calculating the TI for 5-NITP, we find that this value is ~128. The calculated value for 5-PhITP is 660-3300 and is more favorable than that calculated for 5-NITP. The importance of these values is that the difference suggests that 5-PhITP would be "safer" than 5-NITP as a chemopreventive agent. However, this conclusion needs to be validated through careful in vivo analyses.

Conclusions

This report outlines the development of a series of novel nonnatural nucleotide analogues that act as selective inhibitors of replication opposite an abasic site. We demonstrate that two analogues containing substituent groups with extended conjugated systems (5-NITP and 5-PhITP) are preferentially incorporated opposite an abasic site. Furthermore, the potency and efficacy of these analogues is reflected in their high affinity for incorporation opposite the lesion ($K_{Dx}$ 10 µM) and their ability to terminate DNA synthesis with low $IC_{50}$ values of ~10 µM. Finally, these molecules were more resistant to enzymatic excision when placed opposite an abasic site compared to natural nucleotides such as dATP.

These results have several important ramifications toward the development and implementation of these analogues as innovative chemotherapeutic agents. Since these nonnatural nucleotides are selectively inserted opposite abasic sites, they may potentiate the cytotoxic effects of DNA damaging agents such as temozolomide and cyclophosphamide that can increase the formation of abasic sites by enhancing the spontaneous rate of depurination or through DNA repair mechanisms. Our nucleotide analogues could potentiate the cytotoxic effects of these chemotherapeutic agents since they may inhibit the repair of lesions caused by various DNA damaging compounds. The benefit of potentiation is that lower doses of DNA damaging agents could be administered to reduce the potential for common side effects including immunosuppression, nausea, and allopecia that are associated with these agents.

An additional advantage of these nonnatural nucleotides lies in their chemopreventive potential when used in combination with DNA damaging chemotherapeutic agents. This aspect is important since a significant concern of chemotherapy is the generation of mutational errors caused by the inappropriate replication of unrepaired DNA lesions caused by DNA damaging agents. Indeed, it is now recognized that the development of secondary cancers can arise from inadvertent mutagenesis caused by chemotherapeutic drugs that induce DNA damage. One prevalent example is treatment-related acute myeloid leukemia (tAML), which can develop after exposure to DNA alkylating agents such as chlorambucil and cyclophosphamide. These nonnatural nucleotides could be instrumental in the prevention of secondary cancers since they would inhibit the propagation of genomic errors caused by DNA damaging agents. We note that the calculated toxicity and therapeutic indices are lower than what would be expected for a truly effective and potent chain terminator. However, these low values arise from the rigorous exonuclease proofreading associated with the bacteriophage T4 polymerase. We hypothesize that these values will be higher depending upon the DNA polymerase. For example, error prone DNA polymerase such as pol η and pol κ are devoid of or have significantly reduced exonuclease activity. A reduction or omission in exonuclease activity coupled with high discrimination in insertion would significantly increase the toxicity index of these nonnatural nucleotides. Since error-prone DNA polymerases are proposed to be responsible for replicating beyond most DNA lesions, including abasic sites, we speculate that the toxicity index for nonnatural nucleotides such as 5-PhITP will be considerably higher than that reported here once tested for in vivo efficacy.

Example 3

Defining the Dynamics of Nucleotide Incorporation Opposite an Abasic Site: A Structure-Activity Relationship of Modified Purine Triphosphate Analogs The replication of damaged DNA is considered to be a pro-mutagenic event1 that can culminate in the development of various diseases, the most notably of which is cancer. A commonly occurring form of DNA damage is an abasic site that can be produced both non-enzymatically and enzymatically through the action of various DNA repair enzymes. Although an abasic site is devoid Watson-Crick hydrogen bonding potential, most replicative DNA polymerases preferentially incorporate dATP opposite this lesion. This kinetic phenomenon is commonly referred to as the "A rule" of translesion DNA synthesis. Indeed, kinetic studies using gp43, the bacteriophage T4 DNA polymerase, demonstrate that dATP is incorporated opposite an abasic site with a ~35-fold greater overall catalytic efficiency compared to dGTP. This difference is caused through enhanced binding affinity for dATP ($K_D$ values of 35 µM versus 130 µM for dATP and dGTP, respectively) as well as through an increase in the rate constant for polymerization for dATP (kpol values of 0.15 s$^{-1}$ and 0.023 s$^{-1}$ for dATP and dGTP, respectively).

We previously identified a series of non-natural nucleotides that are incorporated opposite an abasic site with nearly 1.000-fold higher catalytic efficiency than dATP. Unique amongst these modified indolyl analogs are 5-NITP and 5-PhITP which display extremely fast $k_{pol}$ values of 126 and 53 sec$^{-1}$, respectively. In addition, both analogs bind with higher affinity than dATP, having $K_D$ values of 18 µM for 5-NITP and 6 µM for 5-PhITP. Despite being significantly different with respect to shape and size (FIG. 18A), both non-natural nucleotides are relatively hydrophobic and rich in π-electron density compared to natural dNTPs. We argued that these two biophysical features provide greater base-stacking capabilities and account for their enhanced incorporation opposite an abasic site.

In this manuscript, we have further probed this proposed mechanism by monitoring the kinetics of nucleotide incorporation opposite an abasic site using a library of purine analogs (FIG. 18A). The first advantage to this approach is with respect to the greater diversity of biophysical features associated with the modified purines compared to the non-natural indolyl triphosphates. The second advantage lies in our ability to quantify the effects of atomic substitutions and/or permutations of the functional groups present on either analog on the kinetics of their incorporation and subsequent elongation. Through this approach, the influence on binding affinity ($K_D$ effect), polymerization rate ($k_{pol}$ effect), or a combination of the two can be related to the associated differences in shape/size, hydrophobicity, solvation energy, dipole moment, and base-stacking capacity of each modified purine. The resulting structure-activity relationship provides a consistent theme in which $k_{pol}$ is influenced by hydrophobic features and aromatic properties associated with the incoming nucleotide. A more complex situation exists with respect to binding affinity as this kinetic step appears to be influenced by several interrelated features of the nucleotide. A comparison of the data obtained with these modified purines versus indolyl triphosphates reveals significant differences in $K_D$ and $k_{pol}$ values. Despite these differences, however, comparison of the kinetic data for either class of nucleotide analog provides evidence for a comprehensive model that accounts for the influence of hydrophobicity and π-electron density on ground state nucleotide binding and conformational change steps that occur during translesion DNA replication.

Materials and Methods

Materials

[γ-$^{32}$P] ATP was purchased from MP Biomedical (Irvine, Calif.). Unlabelled dNTPs (ultrapure) were obtained from Pharmacia. $MgCl_2$ and Trizma base were from Sigma. Urea, acrylamide, and bis-acrylamide were from Aldrich. Oligonucleotides, including those containing a tetrahydrofuran moiety mimicking an abasic site, were synthesized by Operon Technologies (Alameda, Calif.). 2-APTP, 2,6 DAPTP, dIPTP, 8-oxo-dATP, 6-C1PTP, 6-C1-2-APTP, 7-deaza dATP, $N^2$-methyl dGTP, $O^6$-methyl dGTP, $N^6$-methyl dATP was obtained from TriLink BioTechnologies (San Diego, Calif.), 7-deaza dGTP was obtained from Sigma in greater than 99% purity. All other materials were obtained from commercial sources and were of the highest available quality. The exonuclease-deficient mutant of gp43 (Asp-219 to Ala mutation) was purified and quantified as previously described.

General Methods

5'-ends of the primer and template stands were labeled using [γ-$^{32}$P]-ATP and T4 polynucleotide kinase (Gibco-BRL). Single-stranded and duplex DNA were purified and quantified as previously described. The assay buffer used in all kinetic studies consisted of 25 mM Tris-OAc (pH 7.5), 150 mM KOAc, and 10 mM 2-mercaptoethanol. All assays were performed at 25° C. Polymerization reactions were monitored by analysis of the products on 20% sequencing gels as described by Mizrahi et al. Gel images were obtained with a Packard PhosphorImager using the OptiQuant software supplied by the manufacturer. Product formation was quantified by measuring the ratio of $^{32}$P-labelled extended and non-extended primer. The ratios of product formation are corrected for substrate in the absence of polymerase (zero point). Corrected ratios are then multiplied by the concentration of primer/template used in each assay to yield total product. All concentrations are listed as final solution concentrations.

Determination of the Kinetic Rate and Dissociation Constants for dXTP Incorporation The kinetic parameters $k_{pol}$ and $K_D$ for each dXTP during DNA synthesis were obtained by monitoring the rate of product formation using a fixed amount of gp43 exo$^-$ (1 μM) and DNA substrate (250 nM) at varying concentrations of nucleotide triphosphate (0.01-0.5 mM). Aliquots of the reaction were quenched into 200 mM EDTA, pH 7.4 at times ranging from 5-240 seconds. In some instances, time courses were generated using a rapid quench instrument as previously described. These experiments were likewise performed using single turnover conditions in which 1 μM gp43exo$^-$ and 250 nM 13/20SP-mer were mixed against various concentrations of dNTP (10-500 μM) at time intervals ranging from 0.005 to 10 seconds. The reactions were quenched through the addition of 350 mM EDTA. Quenched samples were diluted 1:1 with sequencing gel load buffer and products were analyzed for product formation by denaturing gel electrophoresis. Data obtained for single turnover rates in DNA polymerization were fit to the equation:

$$y = Ae - k_{obs}*t + C$$

where A is burst amplitude, $k_{obs}$ is the first order rate constant, t is time, and C is a defined constant. Data for the dependency of $k_{obs}$ versus dXTP concentration were fit to the Michaelis-Menten equation:

$$k_{obs} = k_{pol}[dXTP]/K_D + [dXTP]$$

where $k_{obs}$ is the apparent first order rate constant, $k_{pol}$ is the maximal polymerization rate constant, $K_D$ is the kinetic dissociation constant for dXTP, and dXTP is the concentration of nucleotide substrate.

Extension Beyond an Abasic Site

Single turnover conditions were used to measure the rates of extension beyond a dXMP:abasic site base pair. Gp43 exo$^-$ (1 μM) was incubated with 250 nM DNA (13/20SP-mer) in assay buffer containing EDTA (100 μM) and mixed with 100 μM dXTP and 10 mM MgAcetate. After ~60 seconds, 900 μM dGTP (the next correct dNTP for the next three positions) was added. Aliquots of the reactions were quenched with 500 mM EDTA at variable times (5-900 sec) and analyzed as described above.

Results and Discussion

This report outlines our efforts to delineate the molecular mechanism accounting for the unexpected discrimination in purine incorporation opposite an abasic site, a nontemplating DNA lesion (FIG. 18B). We employed an approach to quantify the effects of various atomic substitutions and permutations of functional groups present on either dATP or dGTP toward the kinetics of incorporation and elongation. FIG. 18A illustrates the diversity of nucleotide analogs used in this study. As highlighted in Table 7, these analogs differ with respect to numerous biophysical parameters including (but not limited to) surface area, solvation energy, dipole moment, and π-electron density. The kinetic parameters $K_D$ and $k_{pol}$ for the incorporation of these dXTPs opposite an abasic site were measured using gp43exo$^-$ as the model DNA polymerase. All reactions were performed using single turnover reaction conditions to measure the kinetic steps outlined in FIG. 5 that reflect initial ground state binding of dXTP (Step 2), the conformation change prior to chemistry (Step 3)

TABLE 7

Summary of kinetic parameters for the incorporation of non-natural nucleotides opposite an abasic site[a]

| Analog | $K_D$ [μM] | $k_{pol}$ (s$^{-1}$) | Surface Area (Å$^2$)[b] | Dipole momentary (Debye)[c] | Solvation Energy (kcal/mol) | Aromatic Nature |
|---|---|---|---|---|---|---|
| dATP[d] | 35 ± 5 | 0.15 ± 0.01 | 143.0 | 2.38 | −19.258 | dATP |
| dGTP[d] | 130 ± 5 | 0.023 ± 0.005 | 152.5 | 7.18 | −26.009 | dGTP |
| 5-NITP[e] | 18 ± 3 | 126 ± 7 | 171.4 | 7.81 | −7.381 | NA[G] |
| 5-PhITP[f] | 14 ± 3 | 5 ± 4 | 223.2 | 3.31 | −5.532 | NA |
| 7-Deaza dATP | 197 ± 40 | 1.4 ± 0.1 | 148.7 | 3.64 | −17.846 | dATP |
| 7-Deaza dGTP | 215 ± 91 | 0.11 ± 0.02 | 158.2 | 4.95 | −24.247 | dGTP |
| N$^6$-methyl dATP | 190 ± 45 | 5.6 ± 0.6 | 165.0 | 2.16 | −16.322 | dATP |
| O$^6$-methyl dGTP | 181 ± 35 | 0.98 ± 0.08 | 174.5 | 2.94 | −19.998 | dATP |
| N$^2$-methyl dGTP | 245 ± 68 | 0.12 ± 0.02 | 173.1 | 7.54 | −22.306 | dGTP |
| 2-APTP | 180 ± 23 | 0.23 ± 0.02 | 143.2 | 3.10 | −19.142 | dATP |
| 6-Cl-dATP | 83 ± 16 | 0.28 ± 0.02 | 145.2 | 4.99 | −16.449 | dATP |
| dITP | 103 ± 14 | 0.044 ± 0.003 | 139.0 | 5.63 | −21.790 | dGTP |
| 6-Cl-2APTP | 71 ± 20 | 0.12 ± 0.01 | 158.7 | 4.83 | −19.063 | dATP |
| 8-Oxo dATP | ND | ND | 152.4 | 3.74 | −21.750 | dATP |
| 2,6-DAPTP | 900 ± 70 | 2.4 ± 0.3 | 156.4 | 0.82 | −22.335 | dATP |

[a]Assays were performed using 1 μM gp43 exo-, 250 nM 13-20SP-mer, and variable concentrations of non-natural nucleotide in the presence of 10 mM Mg2+.
[b]Surface areas (used as an indicator of the relative size of the nucleobase), dipole moments (debye), and solvation energies for each nucleobase were calculated using Spartan '02 software.
[c]Aromatic nature refers to whether the purine analog has the same tautomeric form as dATP or dGTP.
[G]NA = not applicable that reflect initial ground state binding of dXTP (step 2), the conformational change prior to chemistry (step 3), and/or the chemistry step itself (step 4).

Representative data provided in FIG. 19A illustrates the dependency on the rate constant in primer elongation as a function of N$^6$-methyl dATP concentration. Each time course in primer elongation was fit to the equation defining a single exponential process eqn 1) to obtain kobs values. The plot of $k_{obs}$ versus N$^6$-methyl dATP concentration is hyperbolic (FIG. 19B) and was fit to the Michaelis-Menten equation to obtain a $K_D$ of 190+/−45 μM and a $k_{pol}$ of 5.6+/−0.6 sec$^1$.

Identical analyses were performed for each nucleotide analog used in this study. $K_D$ and $k_{pol}$ values for each analog are summarized in Table 7. These data provide a structure activity relationship (SAR) highlighting the importance of various biophysical parameters toward the efficiency of nucleotide incorporation. To facilitate discussion, we have sub divided our analyses to discuss the effects of atomic substitutions and permutations on binding affinity ($K_D$ effect), the rate constant for polymerization ($k_{pol}$ effect), and the rate constant for elongation ($k_{ext}$ effect).

Biophysical Parameters Affecting Binding Affinity (KD Effect)

Our analyses begins by first comparing the binding affinity for modified purine analogs versus two representative indolyl analogs, 5-NITP and 5-PhITP. As summarized in Table 7, both 5-NITP and 5-PhITP have significantly lower $K_D$ values compared to dATP, dGTP, and any modified analog of these purines. We originally proposed that the low $K_D$ values of 10 μM 5-NITP and 5-PhITP reflected their favorable solvation energies and extended π-electron surface areas. Thus, it was predicted that lowering the solvation energy and/or increasing the π-electron surface area of any purine by modifying various functional groups would enhance their binding affinity and be reflected in low $K_D$ values as well. Surprisingly, the kinetic data provided in Table 7 provided evidence to the contrary as any atomic substitution and/or permutation of functional groups present on dATP or dGTP does not enhance binding affinity as predicted.

One example that illustrates this phenomenon is apparent by examining the influence of removing the potential hydrogen groups at the N−7 position of each purine. This modification increases the hydrophobic nature of each purine by ~1.5 kcal/mol. Rather than enhance binding affinity, removal of N−7 group actually reduces it for both dATP and dGTP. Specifically, the $K_D$ of 200 μM for 7-deaza-dATP is nearly identical to that of 215 μM for 7-deaza-dGTP. It is striking that removing this functional group has a more pronounced on the $K_D$ value for dATP (6-fold decrease) than dGTP (2-fold decrease). In this respect, it is surprising that this modification allows both purine analogs to bind with nearly identical affinities. These data first argue that solely decreasing the solvation energy of a nucleotide does not increase its binding affinity. Secondly, the reduction in binding affinity suggests that altering the hydrogen bonding potential has an adverse effect on binding affinity.

The influence of other potential hydrogen groups on binding affinity was next evaluated by examining purines containing modifications to the 6- or 2-position of either dATP or dGTP. With the exception of 6-Cl-2APTP, any modification to the functional groups of dGTP adversely affects binding affinity (Table 7). For example, the $K_D$ for O$^6$-methyl dGTP is 180 μM while the $K_D$ for N$^2$-methyl-dGTP is 245 μM. In both cases, alkylation of a hydrogen bonding group reduces affinity by ~2-fold. Likewise, alkylation at the O6-position of dATP also has a negative effect on nucleotide binding as manifest in a high $K_D$ value of 190 μM. Again, it is quite striking that the $K_D$ of 190 μM for N$^6$-methyl dATP is essentially identical to that of 180 μM for O$^6$-methyl-dGTP. At face value, these data suggest that perturbing the hydrogen bonding potential of the incoming nucleotide decreases binding affinity. However, this simple explanation is incomplete since 2-APTP, an isosteric analog of dATP, also has a relatively high $K_D$ value of 180 μM. It is remarkable that dATP and 2-APTP display such large differences in binding affinities since both are similar with respect to composition, size, solvation energy, and dipole moment (Table 7). The most obvious difference between dATP and 2-APTP is with respect to positioning of the exocyclic amino group.

A sub-set of analogs including 6-C1-dATP, 6-C1-2APTP, and ITP show minimal perturbations in binding affinity (~3-fold). Attempts to derive a correlation between binding affinity and a singular biophysical parameter were unfortunately unsuccessful. All three analogs differ with respect to shape, hydrophobicity/solvation energies, and dipole moment. However, all three possess a functional group at the C6-position that may be inefficiently substitute for the amino group. In these instances, the data clearly indicate that replacing the amino group at the C6-position of dATP negatively influences binding affinity.

Collectively, the data obtained with all modified purine analogs highlight the importance of functional groups at the C6 and N7 positions enhance binding affinity during translesion DNA synthesis. In general, a strong correlation between binding affinity with the size and/or shape of the incoming dNTP is not observed. The lack of correlation argues against a model invoking steric constraints/shape complementarity as a model to explain binding affinity. Likewise, a model invoking base-stacking interactions also appears incomplete since a distinct correlation between binding affinity and hydrophobicity and/or π-electron density is not observed. One model that may explain the data is that of negative selection originally proposed by Chiaramonte et al. using the Klenow fragment of DNA polymerase from *Escherichia coli*. In this model, the polymerase is capable of interacting with each of the four natural dNTPs equally well. However, only the dNTP that adopts the lowest energy conformation when paired opposite an abasic site can allow the polymerase to catalyze phosphodiester bond formation. With respect to gp43, one possibility is the polymerase "recognizes" the C6 position and the N7 group as determinants to adopt the lowest energy conformation to thereby enhance binding affinity during translesion DNA synthesis. We acknowledge that further analysis with other modified purines is needed to validate this model. Regardless, it is clear that there are significant difference in the binding affinities for non-natural indolyl triphosphates compared with modified purines. As discussed later, these differences likely reflect subtle nuances in the mechanism of nucleotide recognition and selection during translesion DNA synthesis.

Biophysical Parameters Affecting the Polymerization Rate Constant (kpol Effect)

Although the molecular forces influencing dXTP binding remain ambiguous, it is clear that the $k_{pol}$ step is influenced by the hydrophobic and aromatic nature of the incoming dXTP. The effect of hydrophobicity on the $k_{pol}$ step is perhaps best exemplified by the 7-deaza-purine triphosphates (Table 7). The $k_{pol}$ of 1.4 $sec^{-1}$ for 7-deaza dATP is ~10-fold higher than that for dATP. A similar effect is observed with 7-deaza dGTP as the $k_{pol}$ of 0.11 $sec^{-1}$ is ~5-fold higher than that for dGTP. Indeed, direct comparison of $k_{pol}$ values for the incorporation of dATP versus 7-deaza dATP reveals an overall decrease in $\Delta\Delta G^0$ of ~1.4 kcal/mol. This value compares favorably with the 1.5 kcal/mol difference in solvation energies between dATP and 7-deaza dATP. Similar analyses performed for dGTP and 7-deaza dGTP yield comparable interpretations. It is also noteworthy that altering the solvation energies of either nucleotide does not change the preference for adenine versus guanine insertion opposite the abasic site. In fact, the catalytic efficiency for 7-deaza dATP is still >10-fold higher than that for 7-deaza dGTP.

The importance of hydrophobicity is also manifest in the $k_{pol}$ values for several alkylated purines such as $N^6$-methyl dATP and $O^6$-methyl dGTP (Table 8). The $k_{pol}$ value of 5.3 $sec^{-1}$ for $N^6$-methyl dATP is 40-fold faster compared to dATP. Likewise, the $k_{pol}$ value of 0.98 $sec^{-1}$ for $O^6$-methyl dGTP is ~40-fold faster than that of 0.023 $sec^{-1}$ measured with dGTP. In each case, the 40-fold difference in $k_{pol}$ values coincides well with the associated differences in solvation energies between each set of alkylated and unmodified purine triphosphate.

Alkylation at the N2 position of dGTP also has a beneficial effect on $k_{pol}$ since the value of 0.12 $sec^{-1}$ is ~5 fold faster than that for dGTP. As before, the faster $k_{pol}$ value coincides with an increase in nucleobase hydrophobicity. We note, however, that the $k_{pol}$ value for $N^2$-methyl-dGTP is ~10-fold slower than that for $O^6$-methyl-dGTP. This difference could reflect the 2.3 kcal/mol difference in solvation energy between the two analogs (Table 8). However, we argue that the 10-fold difference in $k_{pol}$ values between $N^2$-methyl-dGTP and $O^6$-methyl-dGTP reflects variations in their aromatic nature which ultimately influences their base-stacking capabilities. It is generally accepted that the aromatic nature of a molecule is associated with the degree of its cyclic π-electron systems. Inspection of the structures of dATP and dGTP provided in FIG. 18A reveal that the preferred tautomeric form of dATP is more aromatic than dGTP due to the cyclic electron system. In this study, the total HOMA index value for adenine is 0.917 while that for guanine is 0.745. The higher value confirms that adenine is more aromatic than guanine. An identical conclusion was reached when the analysis was performed comparing NICS aromatic indices for either purine.

Additional evidence for the influence of aromaticity on the polymerization rate constant comes from evaluating $k_{pol}$ values for dITP. The $k_{pol}$ value of 0.044 $sec^{-1}$ for dITP is 3.5-fold lower than that of dATP. At face value, the slower $k_{pol}$ value could reflect perturbations in the hydrophobicity of the nucleotide since the solvation energy of −21.790 kcal/mol for dITP is significantly higher than that of −19.258 kcal/mol for dATP. However, dITP also has a different tautomeric form than dATP. Indeed, it is striking that dITP and dGTP have identical tautomeric forms (and presumably similar aromatic indices) that coincide with the nearly identical $k_{pol}$ values of ~0.03 $sec^{-1}$.

The kinetic data for 6-C1-dATP and 2-APTP are also consistent with this model. The $k_{pol}$ value of 0.23 $sec^{-1}$ for 2-APTP and 0.12 $sec^{-1}$ measured for 6-C1-2-APTP are very similar to that measured with dATP (0.15 $sec^{-1}$). Both modified analogs have the same tautomeric form as dATP, a feature that again coincides with the similarities in polymerization rate constants. We note, however, that the $k_{pol}$ value for 6-C1-dATP is 2-fold higher than dATP. This increase may reflect the 2.809 kcal/mol lower salvation energy for 6-C1-dATP compared to dATP. This last example re-emphasizes the fact that the enzymatic conformational change step, as measured by $k_{pol}$ values, is influenced both by the hydrophobic and aromatic nature of the incoming nucleotide.

Nucleotide Analogs Displaying Exceptional Kinetic Behavior

Close inspection of Table 7 reveals two unique results that are worthy of discussion. The first is 8-Oxo-dATP which is similar in overall shape and size to dATP buts is more hydrophilic by 2.5 kcal/mol. Even at the highest concentration of 8-Oxo-dATP tested (350 µM), no incorporation was observed (data not shown). At face value, the lack of insertion appears to validate our conclusions regarding the importance of hydrophobicity during incorporation opposite an abasic site. However, an alternative possibility is that this modification changes in the syn versus anti conformation of the nucleotide and adversely influences it insertion. Indeed, this appears to be the most likely explanation since the incorporation of 8-Oxo-dATP opposite T is 14-fold slower than that for dATP incorporation Other evidence including misincorporation data opposite G and molecular modeling predictions suggest that the syn conformation of 8-oxo-dATP is preferentially incorporated opposite templating DNA. By inference, this conformation would most likely be preferentially incorporation opposite an abasic site.

The other surprising result is the fast $k_{pol}$ value of 2.4 s$^{-1}$ and the high $K_D$ of 900 µM measured for 2,6-DAPTP incorporation opposite an abasic site. The 16-fold increase in $k_{pol}$ compared to that of dATP contradicts the hypothesis that the hydrophobicity of the incoming nucleobase places constraints on the rate constant for polymerization. Likewise, the high $K_D$ value 900 µM for 2,6-DAPTP is puzzling since it was predicted that placing an amino group at the 6-position would increase binding affinity, not hinder it. There is evidence that 2,6-DAPTP displays peculiar behavior when paired opposite templating DNA that might explain the unique results described here. For example, the presence of 2,6-DAPTP significantly stabilizes duplex DNA and abolishes DNA curvature in A-tract DNA when substituted for adenine. These features arguably reflect the ability of 2,6-DAPTP to disrupt the normal spine of hydration of DNA to alter the groove width of DNA. Thus, 2,6-DAPTP may display unusual kinetic behavior during translesion DNA synthesis due to influence potential alterations in hydrogenbonding and/or base-stacking interactions of this nucleotide.

Extension Beyond dXTP:Abasic Site Mispairs

We previously demonstrated that gp43exo$^-$ can extend beyond an abasic site only when dAMP or dGMP are placed opposite the lesion. The kinetics of elongation are proposed to reflect the positioning of these nucleobases in an interhelical position and arguably reflects the enhanced base-stacking capabilities compared to pyrimidines. If correct, then analogs with enhanced base stacking capabilities (increased hydrophobicity and π-electron density) should be easily elongated. This hypothesis was tested using the experimental protocol outlined in FIG. 20A to measure the ability of gp43exo$^-$ to extend beyond the various mispairs. As shown in FIG. 20B, nearly all modified nucleotides that have the same tautomeric form as dATP are more easily elongated whereas those resembling dGTP are not. The data in Table 8 provides a quantitative assessment of the influence of tautomeric form and hydrophobicity toward the rate constants for extension ($k_{ext}$). For example, N$^6$-methyl-dATP and 7-deazadATP have faster $k_{ext}$ values compared to dATP. While both analogs have the same tautomeric form as dATP, we argue that the faster kext also values reflects their increased hydrophobicity which enhances their base-stacking capabilities and interhelical conformation required for elongation.

The influence of aromaticity is also evident when comparing the $k_{ext}$ values of O$^6$-methyl-dGTP with dGTP. In this instance, the ~20-fold increase in $k_{ext}$ for O$^6$-methyldGTP coincides well with the change in aromatic nature (and tautomeric form) that must occur from alkylation at the O6 position. This increase does not arise due to simple increases in hydrophobicity since alkylation at the N2 position of dGTP does not enhance the rate constant for elongation. Furthermore, the slow kinetics of extension beyond dGTP as well as the lack of extension beyond dITP and N$^7$-Deaza dGTP arguably reflects their weaker base-stacking capabilities that reflects a reduction in their aromatic nature.

TABLE 8

Summary of kinetic rate constants for extension beyond an abasic site catalyzed by gp43exo–$^a$.

| dXTP | $k_{ext}$ (s$^{-1}$) | Solvation Energy (kcal/mo) | Tautomeric Form |
|---|---|---|---|
| dATP | 0.25 ± 0.01 | −19.258 | A |
| 7-Deaza dATP | 0.32 ± 0.03 | −17.846 | A |
| N$^6$-Methyl dATP | 0.71 ± 0.04 | −16.322 | A |
| O$^6$-Methyl dGTP | 0.092 ± 0.009 | −22.306 | A |
| 2-APTP | ND | −19.142 | A |
| 6-Cl-2-APTP | 0.033 ± 0.004 | −19.063 | A |
| 2,6-DAPTP | 0.016 ± 0.003 | −22.335 | A |
| 6-Cl-dATP | 0.031 ± 0.003 | −16.449 | A |
| 8-Oxo-dATP | ND | −21.750 | A |
| dGTP | 0.005 ± 0.001 | −26.009 | G |
| N$^2$-Methyl dGTP | ND | −19.998 | G |
| dITP | ND | −21.790 | G |
| 7-Deaza dGTP | ND | −24.247 | G |

$^a$Insertion and extension beyond an abasic site lesion was measured by preincubating gp43exo– (1 µM) with 5'-labeled 13/20SP-mer (500 nM) and then mixing with 50 µM of dXTP to initiate the reaction. After 2 minutes, an aliquot of the reaction was quenched with 200 mM EDTA (denoted as Inc) to measure insertion opposite the lesion. 900 µM dGTP was then added and aliquots of the reaction were quenched with 200 mM EDTA at time intervals raging from 5 to 300 seconds. The generated time courses were fit to equation 1 to define kext, the rate constant for extension beyond the formed mispair.

There are again clear exceptions to this proposed mechanism. For example, 2-APTP cannot be extended despite being similar in tautomeric form and hydrophobicity to dATP. Although the molecular reason for the lack of elongation is currently unknown, it appears that removal of a functional group at the C6 position may also hinder the kinetics elongation. Indeed, it is clear that analogs such as 2-Cl-dATP and 6-Cl-2-APTP are elongated ~10-fold slower compared to dXTPs with minimal perturbations to the exocyclic amino group (dATP, N$^7$-deaza dATP, and N$^6$-methyl dATP). One potential mechanism invokes the contributions of various heterocyclic functional groups during the polymerization cycle. These functional groups provide contacts with the minor groove of DNA and the DNA polymerase that are necessary for polymerase translocation. Another possibility is that the some mispairs distort the primer-template junction more extensive than other mispairs to hinder polymerase translocation to the next correct templating position. Regardless, the data indicate a clear connection between $k_{pol}$ and $k_{ext}$ values that reflect the influence of base-stacking properties of the modified purine.

CONCLUSIONS

Two distinct kinetic steps are proposed to play significant roles for discriminating against nucleotide incorporation opposite the damaged DNA. These include the dXTP binding step (FIG. 5, step 2) which hinders the polymerase from initially forming the nascent mispair and the conformational change step (FIG. 5, step 3) than prevents the subsequent formation of the mispair. A key question remains as to which kinetic step is most sensitive to variations in diverse biophysical features of the incoming nucleotide. This question was addressed by monitoring the incorporation and elongation of modified purines opposite an abasic site. The resulting SAR reveals that the maximal rate constant in polymerization during incorporation opposite an abasic site is predominantly influenced by the hydrophobicity and π-electron surface area of the incoming nucleotide. We argue that this $k_{pol}$ step (FIG. 5, step 3) represents the enzymatic conformational change required to place the incoming nucleotide into an interhelical conformation that then allows for proper alignment of the primer-template necessary for the phosphoryl transfer step ($k_{chem}$) (FIG. 5, step 4). The data provided here indicate that rate constant for this kinetic step during translesion synthesis can be significantly accelerated if the incoming nucleotide possesses enhanced base-stacking properties such as low solvation energies coupled with a high degree of aromaticity. This reinforces the interpretations from our previous studies using non-natural indolyldeoxyribose triphosphates such as 5-NITP and 5-PhITP. Both analogs are rapidly incorporated opposite an abasic site with $k_{pol}$ values of 126 sec$^{-1}$ and 53 sec$^{-1}$ for 5-NITP and 5-PhITP respectively. As illustrated in FIG. 18, both nucleotides have a more extended π-electron surface area compared to the modified purines. Likewise, the solvation energies for 5-nitroindole and 5-phenylindole are −7.38 and −5.53 kcal/mol, respectively, and are much lower than those for any modified purine analogs. The results collectively indicate that the rate of the conformational change is linked with the presence of π-electron density and solvation energies.

The molecular forces dictating nucleotide binding opposite the DNA lesion appear to be more complex than originally proposed. We previously demonstrated that 5-PhITP, 5-CE-ITP, and 5-CH-ITP have low the $K_D$ values of ~10 μM for incorporation opposite an abasic site. Since these analogs are similar in size and hydrophobicity, their identity in $K_D$ values suggested that binding affinity opposite the DNA lesion was influenced by shape/size constraints coupled with favorable desolvation energies. The data obtained using modified purine analogs indicate that this potential mechanism is either incorrect or incomplete. In this regard, all modified dATP and dGTP analogs tested in this study, bind significantly worse than the aforementioned indolyl analogs irrespective of shape/size and hydrophobicity. This dichotomy suggests that there is not a "universal" mechanism with respect to ground state nucleotide binding by the bacteriophage T4 DNA polymerase. The data obtained with modified purines is consistent with the negative selection model in which the polymerase discriminates against those analogs having alterations to the C6 and the N7 functional group. In contrast, data obtained with the indolyl analogs suggests a hybrid model of steric constraints and base-stacking contributions in which the size and hydrophobicity of the incoming nucleotide play the pre-eminent role toward enhancing binding affinity opposite an abasic site.

Having described the invention, the following is claimed:

1. A method of monitoring DNA damage, comprising:
   treating cells of a patient with: 5 phenyl-indolyl-2'deoxyriboside, a phosphate thereof, or a pharmaceutically acceptable salt thereof; and
   determining the amount of the agent incorporated into the DNA of the cells.

2. The method of claim 1, wherein the patient is treated with a DNA damaging agent that generates abasic sites in the DNA of the cells.

3. The method of claim 2, wherein the DNA damaging agent comprises at least one of a chemotherapeutic agent, an antimetabolite, an antitumorgenic agent, an antimitotic agent, an antiviral agent, an antineoplastic agent, an immunotherapeutic agent, or a radiotherapeutic agent.

4. The method of claim 1, wherein the amount of the agent incorporated into the DNA of the cells is indicative of the amount of DNA damage.

* * * * *

SEQUENCE LISTING

<160> NUMBER OF SEQ ID NOS: 4

<210> SEQ ID NO 1
<211> LENGTH: 13
<212> TYPE: DNA
<213> ORGANISM: Artificial Sequence
<220> FEATURE:
<223> OTHER INFORMATION: DNA substrates

<400> SEQUENCE: 1
tcgcagccgt cca                                                          13

<210> SEQ ID NO 2
<211> LENGTH: 20
<212> TYPE: DNA
<213> ORGANISM: Artificial Sequence
<220> FEATURE:
<223> OTHER INFORMATION: DNA Substrate
<220> FEATURE:
<221> NAME/KEY: misc_feature
<222> LOCATION: (14)..(14)
<223> OTHER INFORMATION: n is a, c, g, or t

<400> SEQUENCE: 2
agcgtcggca ggtncccaaa                                                   20

<210> SEQ ID NO 3
<211> LENGTH: 20
<212> TYPE: DNA
<213> ORGANISM: Artificial Sequence
<220> FEATURE:
<223> OTHER INFORMATION: DNA Substrate
<220> FEATURE:
<221> NAME/KEY: misc_feature
<222> LOCATION: (14)..(14)
<223> OTHER INFORMATION: n is a, c, g, or t

<400> SEQUENCE: 3
tcgcagccgt ccangggttt                                                   20

<210> SEQ ID NO 4
<211> LENGTH: 14

```
<212> TYPE: DNA
<213> ORGANISM: Artificial Sequence
<220> FEATURE:
<223> OTHER INFORMATION: DNA Substrate
<220> FEATURE:
<221> NAME/KEY: misc_feature
<222> LOCATION: (14)..(14)
<223> OTHER INFORMATION: n is a, c, g, or t

<400> SEQUENCE: 4
tcgcagccgt ccan                                                          14
```